(12) United States Patent
McCormack et al.

(10) Patent No.: US 11,065,039 B2
(45) Date of Patent: Jul. 20, 2021

(54) SPINAL IMPLANT AND METHODS OF USING THE SAME

(71) Applicant: PROVIDENCE MEDICAL TECHNOLOGY, INC., Pleasanton, CA (US)

(72) Inventors: Bruce M. McCormack, San Francisco, CA (US); Edward Liou, Pleasanton, CA (US); Shigeru Tanaka, Half Moon Bay, CA (US); Jeffrey D. Smith, Clayton, CA (US); Scott Schneider, San Jose, CA (US); Christopher U. Phan, Dublin, CA (US); Wesley Wang, Daly City, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 0 days.

(21) Appl. No.: 16/314,331

(22) PCT Filed: Jun. 27, 2017

(86) PCT No.: PCT/US2017/039582
§ 371 (c)(1),
(2) Date: Dec. 28, 2018

(87) PCT Pub. No.: WO2018/005548
PCT Pub. Date: Jan. 4, 2018

(65) Prior Publication Data
US 2019/0239932 A1 Aug. 8, 2019

Related U.S. Application Data

(60) Provisional application No. 62/357,809, filed on Jul. 1, 2016, provisional application No. 62/357,781, filed
(Continued)

(51) Int. Cl.
*A61B 17/70* (2006.01)
*A61F 2/44* (2006.01)
(Continued)

(52) U.S. Cl.
CPC ............ *A61B 17/7064* (2013.01); *A61F 2/28* (2013.01); *A61F 2/4405* (2013.01); *A61F 2/447* (2013.01);
(Continued)

(58) Field of Classification Search
CPC ............ A61B 17/7064; A61B 17/1671; A61B 2017/0256; A61F 2/28; A61F 2/4405;
(Continued)

(56) References Cited

U.S. PATENT DOCUMENTS 1,934,962 A 11/1933 Barry
2,708,376 A 5/1955 Booth
(Continued)

FOREIGN PATENT DOCUMENTS

DE G9304368.6 U1 5/2003
FR 2722980 A1 2/1996
(Continued)

OTHER PUBLICATIONS

US 7,063,700 B2, 06/2006, Michelson (withdrawn)
(Continued)

*Primary Examiner* — Eduardo C Robert
*Assistant Examiner* — David C Comstock
(74) *Attorney, Agent, or Firm* — Dorsey & Whitney LLP

(57) ABSTRACT

A spinal implant for implantation within a spinal facet joint is provided. The spinal implant may include a main body including opposing top and bottom surfaces, opposing front or distal and rear or proximal surfaces, and opposing side surfaces. At least one retaining feature may be associated with at least one surface of the main body to frictionally
(Continued)

engage the implant within the spinal facet joint. At least one securement feature may be associated with at least one surface of the main body to selectively secure the implant within the spinal facet joint.

16 Claims, 49 Drawing Sheets

Related U.S. Application Data on Jul. 1, 2016, provisional application No. 62/355,618, filed on Jun. 28, 2016.

(51) Int. Cl.
| | | |
|---|---|---|
| *A61F 2/46* | (2006.01) | |
| *A61F 2/28* | (2006.01) | |
| A61B 17/16 | (2006.01) | |
| A61B 17/02 | (2006.01) | |
| A61F 2/30 | (2006.01) | |

(52) U.S. Cl.
CPC .......... *A61F 2/4455* (2013.01); *A61F 2/4611* (2013.01); *A61B 17/1671* (2013.01); *A61B 2017/0256* (2013.01); *A61F 2/4603* (2013.01); *A61F 2002/2835* (2013.01); *A61F 2002/30014* (2013.01); *A61F 2002/30176* (2013.01); *A61F 2002/30593* (2013.01); *A61F 2002/30733* (2013.01); *A61F 2002/30782* (2013.01); *A61F 2002/30828* (2013.01); *A61F 2002/30843* (2013.01); *A61F 2002/30892* (2013.01); *A61F 2002/30904* (2013.01); *A61F 2002/4627* (2013.01); *A61F 2002/4629* (2013.01)

(58) Field of Classification Search
CPC ...... A61F 2/4455; A61F 2/447; A61F 2/4611; A61F 2002/30014; A61F 2002/30018; A61F 2002/30176; A61F 2002/30593; A61F 2002/30733; A61F 2002/30782; A61F 2002/30828; A61F 2002/30843; A61F 2002/30892; A61F 2002/30904; A61F 2002/4475; A61F 2002/4623; A61F 2002/4627; A61F 2002/4629
USPC ............ 606/246, 247, 249; 623/17.11, 17.16
See application file for complete search history.

(56) References Cited

U.S. PATENT DOCUMENTS

| | | |
|---|---|---|
| 2,984,241 A | 5/1961 | Carlson |
| 3,486,505 A | 12/1969 | Morrison |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,192,327 A | 3/1993 | Brantigan |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,200,322 B1 | 3/2001 | Branch et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,530,955 B2 | 3/2003 | Boyle et al. |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |

(56) References Cited

U.S. PATENT DOCUMENTS

| | | |
|---|---|---|
| 6,582,432 B1 | 6/2003 | Michelson |
| 6,582,467 B1 | 6/2003 | Teitelbaum et al. |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,682,393 B2 | 3/2010 | Trieu et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |

(56) References Cited

U.S. PATENT DOCUMENTS

| | | | |
|---|---|---|---|
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| 8,382,767 B2 | 2/2013 | Wassinger et al. |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,512,347 B2 | 8/2013 | McCormack et al. |
| 8,523,908 B2 | 9/2013 | Malone |
| 8,529,609 B2 | 9/2013 | Helgerson et al. |
| 8,623,054 B2 | 1/2014 | McCormack et al. |
| 8,668,722 B2 | 3/2014 | Pavlov et al. |
| 8,753,345 B2 | 6/2014 | Mccormack et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | Mccormack et al. |
| 9,011,492 B2 | 4/2015 | McCormack et al. |
| D732,667 S | 6/2015 | McCormack et al. |
| 9,186,193 B2* | 11/2015 | Kleiner ............... A61B 17/8822 |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,358,127 B2* | 6/2016 | Duffield ............... A61F 2/442 |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | Mccormack et al. |
| 9,622,873 B2 | 4/2017 | Mccormack et al. |
| 9,622,874 B2 | 4/2017 | Mccormack et al. |
| 9,629,665 B2 | 4/2017 | Mccormack et al. |
| 9,717,403 B2 | 8/2017 | Kleiner et al. |
| 10,039,649 B2 | 8/2018 | Mccormack et al. |
| 10,149,673 B2 | 12/2018 | Mccormack et al. |
| 10,172,721 B2 | 1/2019 | Mccormack et al. |
| D841,165 S | 2/2019 | Mccormack et al. |
| 10,201,375 B2 | 2/2019 | Mccormack et al. |
| 10,206,787 B2 | 2/2019 | Voellmicke |
| 10,219,910 B2 | 3/2019 | Mccormack |
| 10,226,285 B2 | 3/2019 | Mccormack et al. |
| 10,238,501 B2 | 3/2019 | Mccormack et al. |
| 10,456,175 B2 | 10/2019 | McCormack et al. |
| 10,568,666 B2 | 2/2020 | McCormack et al. |
| 10,588,672 B2 | 3/2020 | McCormack et al. |
| D884,895 S | 5/2020 | McCormack et al. |
| D887,552 S | 6/2020 | Tanaka et al. |
| 10,682,243 B2 | 6/2020 | Phan et al. |
| 2001/0004710 A1 | 6/2001 | Felt et al. |
| 2001/0047208 A1 | 11/2001 | Michelson |
| 2001/0053914 A1 | 12/2001 | Landry et al. |
| 2002/0026195 A1 | 2/2002 | Layne et al. |
| 2002/0068941 A1 | 6/2002 | Hanson et al. |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2002/0177866 A1 | 11/2002 | Weikel et al. |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0149438 A1 | 8/2003 | Nichols et al. |
| 2003/0158553 A1 | 8/2003 | Michelson |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015097 A1 | 1/2005 | Mujwid et al. |
| 2005/0015149 A1 | 1/2005 | Michelson |
| 2005/0027358 A1 | 2/2005 | Suddaby |
| 2005/0033432 A1 | 2/2005 | Gordon et al. |
| 2005/0038511 A1 | 2/2005 | Martz et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0149192 A1* | 7/2005 | Zucherman ........ A61B 17/1671 623/17.11 |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149289 A1 | 7/2006 | Winslow et al. |

(56) References Cited

U.S. PATENT DOCUMENTS

| | | |
|---|---|---|
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235391 A1 | 10/2006 | Sutterlin, III |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1* | 3/2007 | Khosrowshahi .... A61F 2/30771 623/17.11 |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1* | 6/2008 | Voellmicke ............. A61F 2/447 623/17.16 |
| 2008/0161810 A1 | 7/2008 | Melkent |
| 2008/0167657 A1 | 7/2008 | Greenhaigh |
| 2008/0177311 A1 | 7/2008 | Winslow et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177215 A1 | 7/2009 | Stack et al. |
| 2009/0177237 A1 | 7/2009 | Zucherman et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2010/0069912 A1 | 3/2010 | McCormack et al. |
| 2010/0082065 A1 | 4/2010 | Butler et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114105 A1 | 5/2010 | Butters et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1* | 1/2011 | Assell .................. A61F 2/4405 606/247 |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0179259 A1* | 7/2012 | McDonough ......... A61F 2/4455 623/17.16 |
| 2012/0215259 A1 | 8/2012 | Cannestra |
| 2012/0265250 A1 | 10/2012 | Ali |
| 2012/0283776 A1 | 11/2012 | Mishra |
| 2012/0323242 A1 | 12/2012 | Tsuang et al. |
| 2013/0013070 A1 | 1/2013 | McCormack et al. |
| 2013/0023889 A1 | 1/2013 | Blain et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0144389 A1 | 6/2013 | Bonutti |
| 2013/0226239 A1 | 8/2013 | Altarac et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0025113 A1 | 1/2014 | McCormack et al. |
| 2014/0100657 A1 | 4/2014 | McCormack et al. |
| 2014/0135930 A1 | 5/2014 | Georges |
| 2014/0172103 A1 | 6/2014 | O'neil et al. |
| 2014/0228959 A1* | 8/2014 | Niemiec ............... A61F 2/4455 623/17.16 |
| 2014/0296916 A1 | 10/2014 | Mccormack et al. |
| 2015/0025635 A1 | 1/2015 | Laubert |
| 2015/0100129 A1 | 4/2015 | Waugh et al. |
| 2015/0201977 A1 | 7/2015 | Mccormack et al. |
| 2015/0297357 A1 | 10/2015 | McCormack et al. |
| 2015/0328005 A1* | 11/2015 | Padovani ............ A61F 2/30744 623/17.13 |

(56) References Cited

U.S. PATENT DOCUMENTS

| | | | |
|---|---|---|---|
| 2015/0328010 A1* | 11/2015 | Martynova | A61F 2/442 623/17.16 |
| 2015/0342648 A1 | 12/2015 | Mccormack et al. | |
| 2015/0342649 A1 | 12/2015 | Mccormack et al. | |
| 2016/0008040 A1 | 1/2016 | Mccormack et al. | |
| 2016/0242754 A1 | 8/2016 | Mccormack et al. | |
| 2016/0250035 A1 | 9/2016 | De Villiers et al. | |
| 2017/0027713 A1 | 2/2017 | Kleiner | |
| 2017/0135733 A1 | 5/2017 | Donner et al. | |
| 2017/0189199 A1 | 7/2017 | Maier et al. | |
| 2017/0281360 A1 | 10/2017 | Seifert | |
| 2017/0348027 A1 | 12/2017 | Mccormack et al. | |
| 2017/0354444 A1 | 12/2017 | Mccormack et al. | |
| 2017/0360571 A1* | 12/2017 | Mesiwala | A61F 2/4611 |
| 2018/0161077 A1 | 6/2018 | Mccormack et al. | |
| 2018/0303631 A1 | 10/2018 | Phan et al. | |
| 2019/0209151 A1 | 7/2019 | Mccormack et al. | |
| 2019/0240041 A1 | 8/2019 | McCormack et al. | |
| 2019/0247099 A1 | 8/2019 | McCormack et al. | |
| 2019/0307571 A1 | 10/2019 | McCormack et al. | |
| 2019/0307572 A1 | 10/2019 | McCormack et al. | |
| 2019/0350626 A1 | 11/2019 | McCormack et al. | |
| 2020/0085475 A1 | 3/2020 | McCormack et al. | |
| 2020/0155205 A1 | 5/2020 | Tanaka et al. | |
| 2020/0289285 A1 | 9/2020 | Siemionow et al. | |
| 2020/0375633 A1 | 12/2020 | McCormack et al. | |
| 2021/0022881 A1 | 1/2021 | McCormack et al. | |

FOREIGN PATENT DOCUMENTS

| | | |
|---|---|---|
| JP | 2014516268 A | 7/2014 |
| WO | 9641582 A1 | 12/1996 |
| WO | 99/49818 A1 | 10/1999 |
| WO | 00/035388 | 6/2000 |
| WO | 00/53126 A1 | 9/2000 |
| WO | 01/01895 A1 | 1/2001 |
| WO | 02/34120 A2 | 5/2002 |
| WO | 2002/038062 | 5/2002 |
| WO | 02076335 | 10/2002 |
| WO | 2006-058221 | 6/2006 |
| WO | 2006058221 | 6/2006 |
| WO | 2006130791 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 | 7/2009 |
| WO | 2009148619 | 12/2009 |
| WO | 2010030994 | 3/2010 |
| WO | 2010074714 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 | 4/2016 |

OTHER PUBLICATIONS

Atul Goel, Facetal distraction as treatment for single- and multilevel cervical spondylotic radiculopathy and myelopathy: a preliminary report, J Neurosurg Spine, Jun. 2011, pp. 689-696.

International Search Report and Written Opinion of the International Searching Authority for International Patent Application No. PCT/US2017/039582, dated Sep. 11, 2017 (11 pages).

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

Stein, et al., "Percutaneous Facet Joint Fusion: Preliminary Experience," Journal of Vascular and Interventional Radiology, Jan.-Feb. 1993, pp. 69-74, vol. 4, No. 1.

* cited by examiner

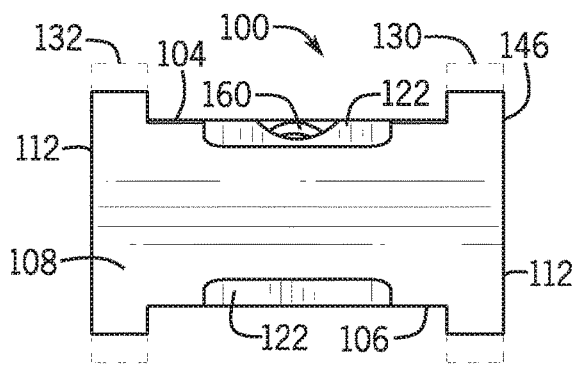
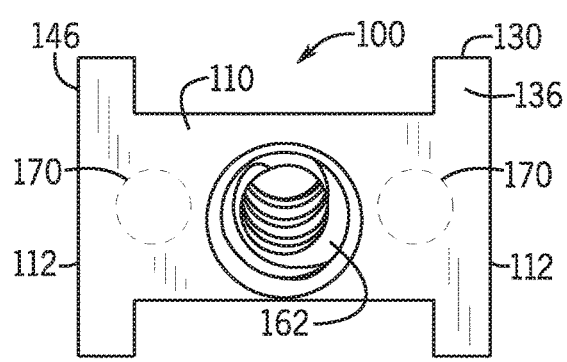
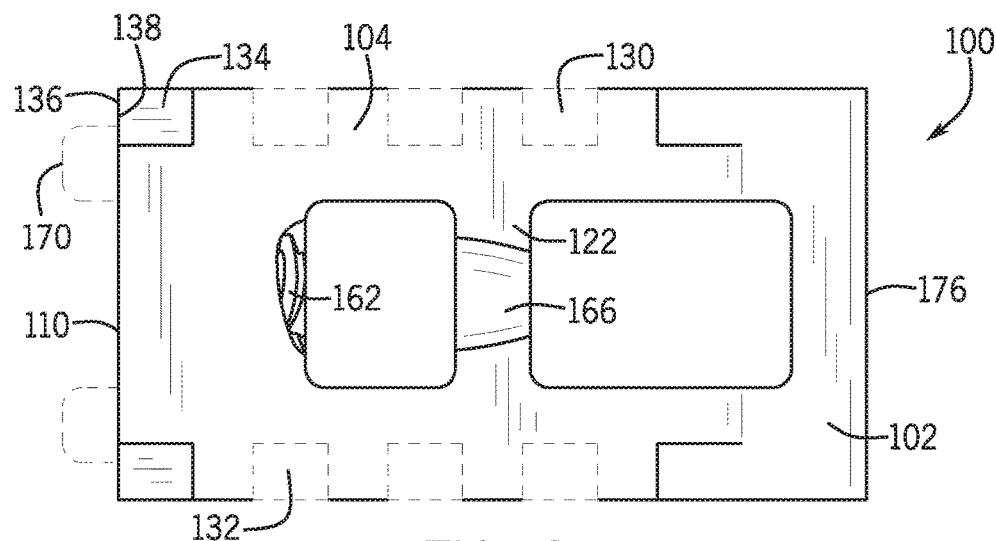
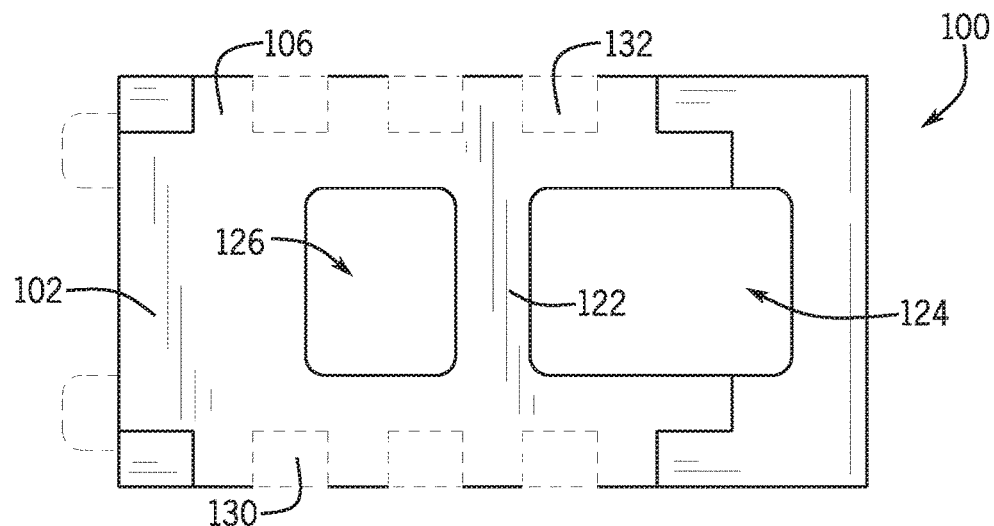

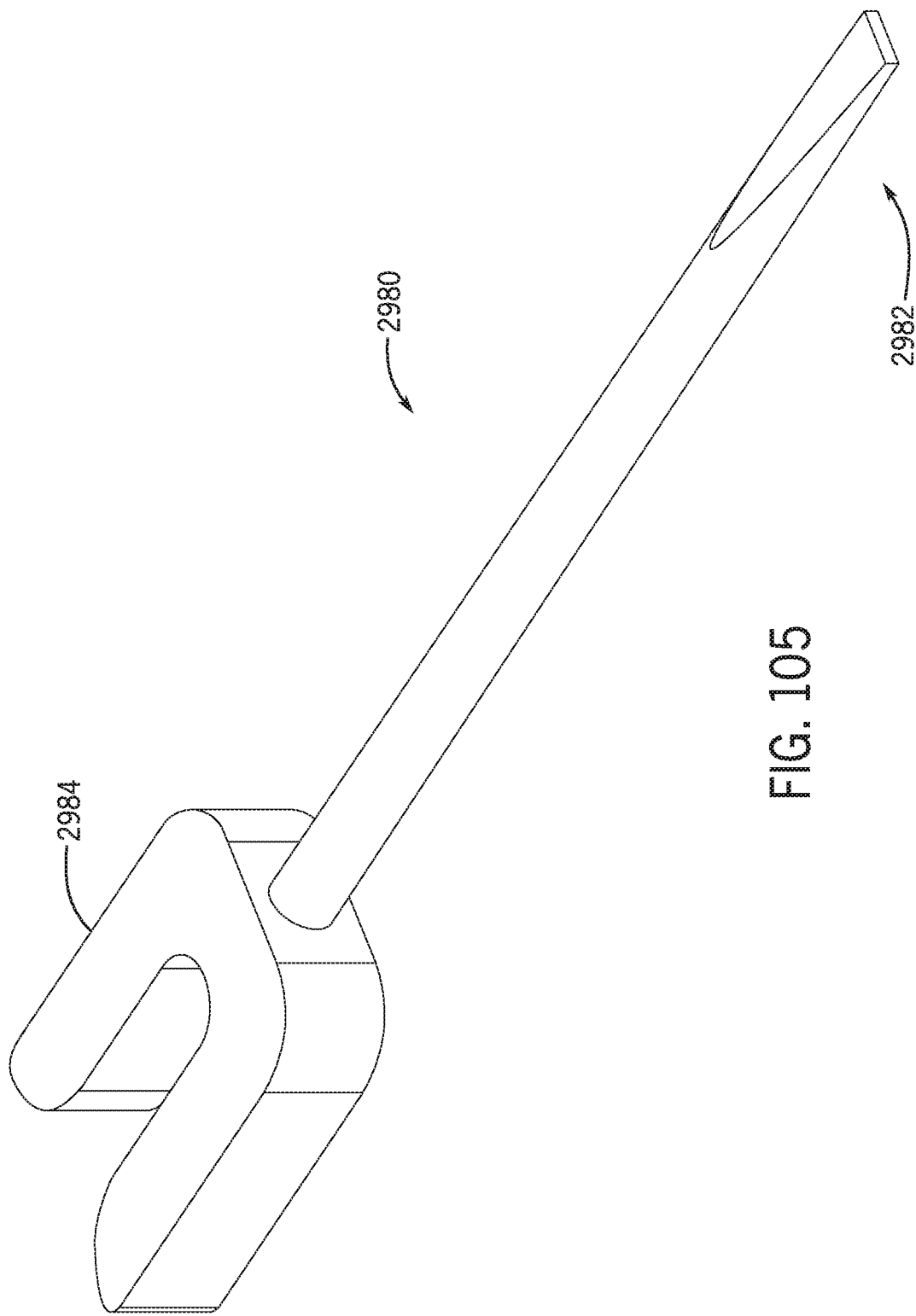

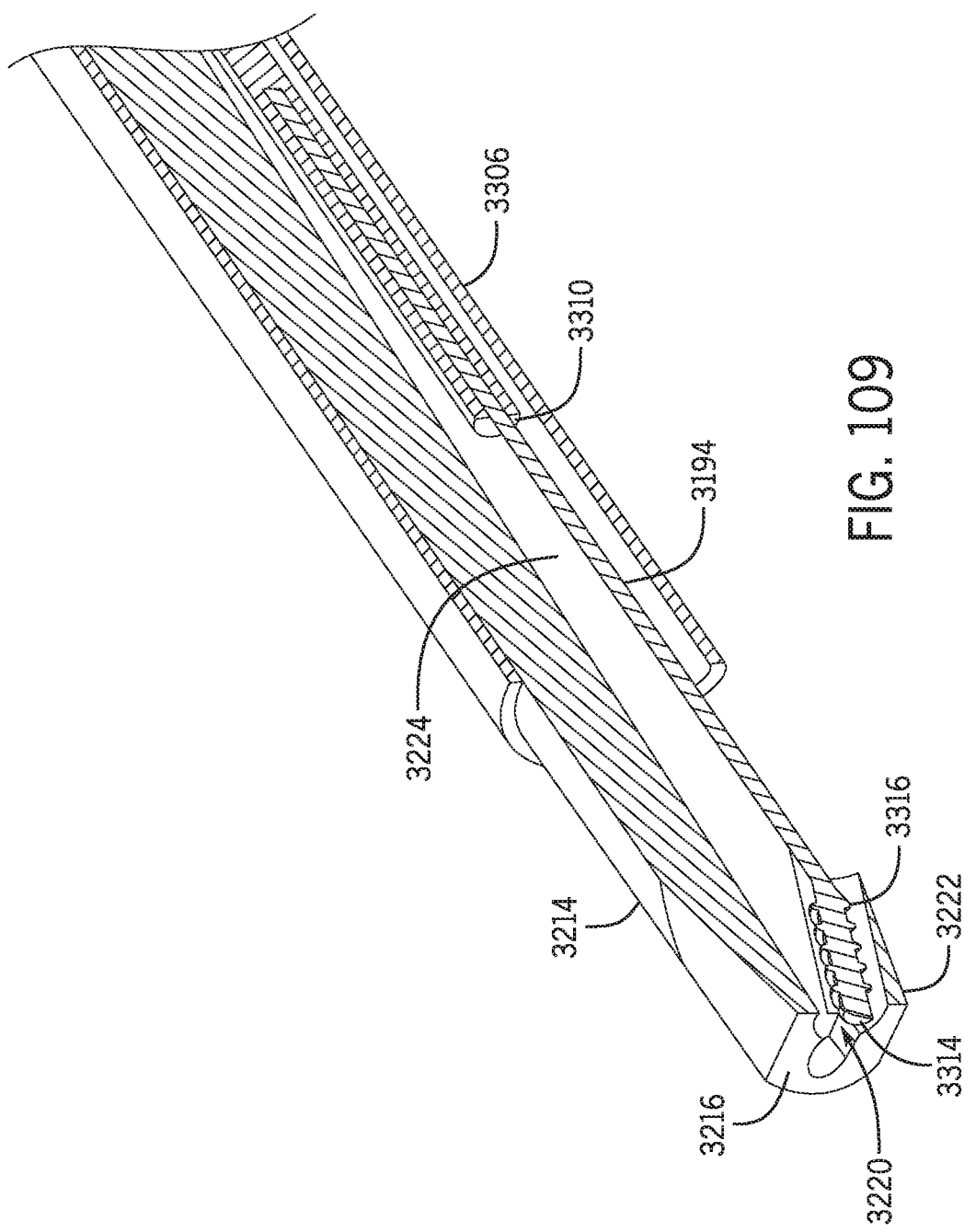

SPINAL IMPLANT AND METHODS OF USING THE SAME

CROSS REFERENCE TO RELATED APPLICATIONS

This application claims priority under 35 U.S.C. 371 to International Patent Application No. PCT/US2017/039582, filed Jun. 27, 2017, which claims priority to and benefit of the following: U.S. Patent Application No. 62/355,618, filed Jun. 28, 2016 and entitled: Spinal Implant Device and Method of Using; U.S. Patent Application No. 62/357,781, filed Jul. 1, 2016 and entitled Spinal Implant; and U.S. Patent Application No. 62/357,809, filed Jul. 1, 2016 and entitled Spinal Implant, all of which are hereby incorporated by reference.

FIELD

This present disclosure relates generally to spinal distraction, and more specifically to devices and methods related to use of a spinal implant to distract a spinal facet joint.

BACKGROUND

Chronic neck and back problems cause pain and disability for a large segment of today's population. Adverse spinal conditions may be characteristic of age. Spinal fusion, in which two adjacent vertebrae are fused together using plates, screws and other implants is often performed in an attempt to increase space between the two adjacent vertebrae being operated on ("spinal distraction") and to thus prevent impingement of the spinal cord or nerve roots branching from the spinal cord and passing through openings in the vertebral column. Unfortunately, most techniques and devices used for performing spinal fusion are relatively invasive and involve a number of risks and difficult recovery and rehabilitation.

One of the reasons that spinal fusion surgery is often very invasive is that, due to the position of the spinal cord in back of (posterior to) the central vertebral bodies of spine, many of the procedures require entering the patient through the front of the body (an "anterior approach") and dissecting through various tissues to gain access to the spine. Fusion procedures are often performed on the cervical spine, which requires dissecting through the neck, or the lumbar spine, which requires dissecting through the abdomen. In either case, cutting through the anterior tissues of the patient to reach the spine is not without risk.

Therefore, it is desirable to have improved devices, systems, and methods for treating spinal stenosis. Ideally, such devices, systems, and methods would allow for minimally invasive or less invasive access and fixation, as well as helping ensure proper placement of the fixation devices. At least some of these objects will be met by the embodiments described herein

BRIEF SUMMARY

The various embodiments described herein provide a spinal implant for implantation in a spinal facet joint. In one implementation, the spinal implant is implanted between two adjacent vertebrae in the facet joint space via a posterior approach. The embodiments described below generally include a spinal implant device that engage, frictionally engage, or engage by a friction fit, for example, adjacent vertebrae. Once frictionally engaged in position within the spinal facet joint, the spinal implant device can be anchored to at least one of the adjacent vertebrae via a fastener, such as a bone screw. The facet joint space may be in the cervical spine.

In one aspect, a spinal implant for implantation within a spinal facet joint is provided. The spinal implant may include a main body having opposing top and bottom surfaces, opposing front and rear surfaces, and opposing side surfaces. At least one retaining feature may be associated with at least one surface of the main body to frictionally engage the implant within the spinal facet joint. At least one securement feature may be associated with at least one surface of the main body to selectively secure the implant within the spinal facet joint.

In some embodiments, the at least one securement feature may include a securement aperture operable to receive a fastener therein. The securement aperture may be angled such that a fastener received therein extends through one of the top or bottom surfaces and rear surface of the main body.

In some embodiments, one or more windows may be defined in at least one surface of the main body. The at least one securement feature may include a bone screw extending at least partially within at least one window of the implant. At least a portion of the bone screw may extend between one of the top or bottom surface and the rear surface of the implant. An interior wall may be position within the main body to define a portion of at least two windows. Two windows may be defined in each of the top, bottom, and opposing side surfaces of the main body. The interior wall may define a portion of each of the two windows defined in the top, bottom, and opposing side surfaces. The at least one securement feature may include a bone screw. The interior wall may be notched to receive a portion of the bone screw therein.

In some embodiments, the at least one retaining feature may include a plurality of protrusions extending away from at least one of the opposing top and bottom surfaces of the main body. Each of the plurality of protrusions may extend from adjacent an edge defined between the opposing top and bottom surfaces and the opposing side surfaces. Each of the plurality of protrusions may include a leading face, a trailing face, and a tip formed at an intersection between the leading and trailing faces. The trailing face may include a slope that is greater than a slope of the leading face. The trailing face may extend substantially perpendicular to the at least one of the opposing top and bottom surfaces of the main body. Each of the protrusions may include a pyramidal shape including a plurality of lateral faces extending from the main body and terminating at the tip. The lateral faces of the pyramidal-shaped protrusions may be congruent. Each protrusion may define a right-angled pyramid. The tip may define a ridge extending the width of each protrusion. The protrusions positioned nearer the front surface of the main body may include a height that is smaller than a height of the protrusions positioned away from the front surface.

In some embodiments, the at least one retaining feature may be associated with at least one of the top and bottom surfaces of the implant. The at least one securement feature may be associated with at least the rear surface of the implant.

In some embodiments, the front surface may be arcuately shaped to define a leading edge that facilitates insertion of the spinal implant within a spinal facet joint.

In some embodiments, one or more posts may extend from the rear surface of the spinal implant. The one or more posts may include two posts extending from the rear surface of the spinal implant in a laterally spaced relationship. The at least one securement feature may include a securement aperture defined within the rear surface between the two posts.

In another aspect, a method of fusing a spinal facet joint is provided. The method may include implanting a spinal implant within a spinal facet joint, providing at least one retaining feature on the spinal implant to frictionally engage the spinal implant within the spinal facet joint, and providing at least one securement feature on the spinal implant to selectively secure the spinal implant within the spinal facet joint.

In some embodiments, providing at least one retaining feature may include extending a plurality of protrusions from opposing top and bottom surface of the spinal implant, the plurality of protrusions operable to frictionally engage adjacent vertebrae of the spinal facet joint.

In some embodiments, the method may include securing the spinal implant within the spinal facet joint by driving a bone screw within an adjacent vertebra, the bone screw received at least partially within a securement aperture defined within the spinal implant. The method may include extending a portion of the bone screw between a rear surface of the spinal implant to one of a top or bottom surface of the spinal implant.

In one aspect, a spinal implant for implantation within a spinal facet joint is disclosed. The implant may include a main body having opposing top and bottom surfaces; opposing distal and proximal surfaces, the distal surface having an arcuate surface defining a leading edge; opposing side surfaces; and at least one lateral edge defined at an intersection between one of the opposing top and bottom surfaces and one of the opposing side surfaces. The implant further includes at least two retaining features positioned on at least one of the top or bottom surfaces of the main body to position the implant within the spinal facet joint, each of the retaining features including a leading face, a trailing face, opposing lateral faces and a tip formed at an intersection between the faces. The leading face of at least one of the at least two retaining features is coextensive with at least a portion of the distal surface. The at least one of the opposing lateral faces extends from the top or bottom surface at a location away from the at least one lateral edge.

With respect to the retaining features, in some aspects, the trailing face may include a slope that is greater than a slope of the leading face. In some aspects, the trailing face of at least one of the retaining features extends substantially perpendicular to the at least one of the opposing top and bottom surfaces of the main body. In some aspects, the trailing face of at least one of the retaining features extends substantially coextensively with the proximal surface of the main body. In some aspects, the tip defines a ridge extending the width of each retaining feature. In some aspects, at least one of retaining features positioned nearer the distal surface of the main body has a height that is smaller than a height of the retaining features positioned away from the distal surface.

In some aspects, the implant further includes one or more windows defined in at least one surface of the main body. In some aspects, the implant further includes at least one securement feature, said securement feature including a bone screw extending at least partially within at least one window of the implant. The at least a portion of the bone screw may extend between the top or bottom surface and the proximal or rear surfaces of the implant.

In some aspects, the implant includes an interior wall positioned within the main body to define a portion of at least two windows. The two windows may be defined in each of the top, bottom, and opposing side surfaces of the main body; and the interior wall defines a portion of each of the two windows defined in the top, bottom, and opposing side surfaces. The implant may further include at least one securement feature, wherein: the at least one securement feature includes a bone screw; and the interior wall is notched to receive a portion of the bone screw therein.

In some aspects, the at least one retaining feature is associated with at least one of the top and bottom surfaces of the implant; and the at least one securement feature is associated with at least the proximal or rear surface of the implant.

In some aspects, the implant further includes one or more posts extending from the proximal surface of the spinal implant. In some aspects, the one or more posts includes two posts extending from the proximal surface of the spinal implant in a laterally spaced relationship; and the at least one securement feature includes a securement aperture defined within the proximal surface between the two posts.

A method of fusing a spinal facet joint is disclosed. In some aspects, the method includes implanting a spinal implant within a spinal facet joint, the spinal implant includes: a main body including opposing top and bottom surfaces; opposing distal and proximal surfaces, the distal surface having an arcuate surface defining a leading edge; opposing side surfaces; and at least one lateral edge defined at an intersection between one of the opposing top and bottom surfaces and one of the opposing side surfaces. The implant further includes at least two retaining features positioned on at least one of the top or bottom surfaces of the main body to position the implant within the spinal facet joint, each of the retaining features including a leading face, a trailing face, opposing lateral faces and a tip formed at an intersection between the faces. The leading face of at least one of the at least two retaining features is coextensive with or adjacent to at least a portion of the distal surface, and at least one of the opposing lateral faces extending from the top or bottom surface at a location away from the at least one lateral edge. The method further includes securing the implant in the spinal facet joint to promote fusion.

In some aspects, securing the spinal implant within the spinal facet joint comprises driving a bone screw within an adjacent vertebra, the bone screw received at least partially within a securement aperture defined within the spinal implant. In some aspects, securing the spinal implant within the spinal facet joint comprises allowing the retaining features to engage the adjacent vertebra by a friction fit.

In some aspects, the method further includes extending a portion of the bone screw between a proximal surface of the spinal implant to one of a top or bottom surface of the spinal implant. In some aspects, the method further includes providing bone growth material inside of the implant to promote fusion.

Disclosed herein is an improved implant for spinal joint fusion procedures. The improved implant provides an allograft (bone graft) core and a shell having fixation members, such as teeth. The shell can be visualized with X-ray or other imaging thereby allowing a practitioner to ensure proper placement and confirm that the implant has not moved after placement. Preventing implant motion immediately post-implantation is helpful in promoting fusion. In addition, the allograft core promotes new bone growth and fusion.

In some aspects, the spinal implant device includes an implant shell having at least one fixation member and a graft core received in the implant shell to form a spinal implant. The implant shell and the graft core are made of different materials. In one aspect the implant shell is a resilient and/or semi-rigid material. In another aspect, the implant shell is a biocompatible metal or is a plastic having a selective radiopacity. The graft core may be an allograft core. The graft core may be coupled to the implant shell by friction or by a complementary engagement feature matingly received by the shell.

In some aspects, the implant shell further includes a proximal end and a distal end and has at least one opening at the proximal end to receive the graft core.

The implant shell may also include at least two vertebra engagement surfaces, each of the engagement surfaces having at least one aperture or opening defined therein. In some aspects, each of the engagement surfaces comprises at least one of the fixation members. In one aspect, at least two engagement surfaces are angularly offset with respect to one another.

In some aspects, the implant shell further includes a connecting member coupled to each of the at least two engagement surfaces. The connecting member may be a resilient and/or flexible material.

In some embodiments, the graft core further includes a complementary engagement feature matingly received by the at least one aperture of the engagement surface. The complementary engagement feature of the graft core may protrude from a surface of the graft member to couple with the implant shell.

In some aspects, the implant shell further includes at least one retention tab matingly received in a complementary recess of the graft core. Further, the graft core may include at least two channels defined in opposite lateral surfaces of the graft core for engaging a graft core insertion tool. In some aspects, the spinal implant is a facet joint implant. The facet joint may be located in the cervical spine.

A spinal fixation method is also disclosed. In some aspects, the method includes introducing a spinal implant into a facet joint. The implant includes an implant shell having at least one fixation member and a graft core received in the implant shell to form a spinal implant. The implant shell and the graft core are different materials. The method further includes securing the spinal implant in the facet joint via the at least one fixation member. The facet joint may be located in the cervical spine.

A system for delivering a spinal implant into a spinal facet joint space via a posterior approach is disclosed. In some aspects, the system includes a spinal implant including an implant shell having at least one fixation member, and a graft core received in the implant shell to form a spinal implant. The implant shell and the graft core are different materials. The system may further include a delivery tool comprising a proximal end and a distal end, the spinal implant received at the distal end. The system may further include a guide tool defining a longitudinally extending lumen, wherein the delivery tool is received in the lumen of the guide tool to deliver the implant into the spinal facet joint space. The spinal facet joint space is in the cervical spine. The system may further include a decorticator to roughen a bone surface of the spinal facet joint prior to delivery of the spinal implant. The system may further include a place holding chisel.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and drawings, which form part of the disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The accompanying drawings, which are incorporated into and constitute a part of the specification, illustrate embodiments of the disclosure and, together with the general description above and the detailed description below, serve to explain the principles of these embodiments.

FIG. 4 is a front elevation view of the spinal implant device of FIG. 1 in accordance with an embodiment of the present disclosure.

FIG. 5 is a rear elevation view of the spinal implant device of FIG. 1 in accordance with an embodiment of the present disclosure.

FIG. 6 is a top plan view of the spinal implant device of FIG. 1 in accordance with an embodiment of the present disclosure.

FIG. 7 is a bottom plan view of the spinal implant device of FIG. 1 in accordance with an embodiment of the present disclosure.

FIG. 105 is a perspective view of an example malleting tool.

FIGS. 108-109 is an example delivery device, a detailed view of a distal end of the delivery device and a cross section view.

DETAILED DESCRIPTION

Figure 1:
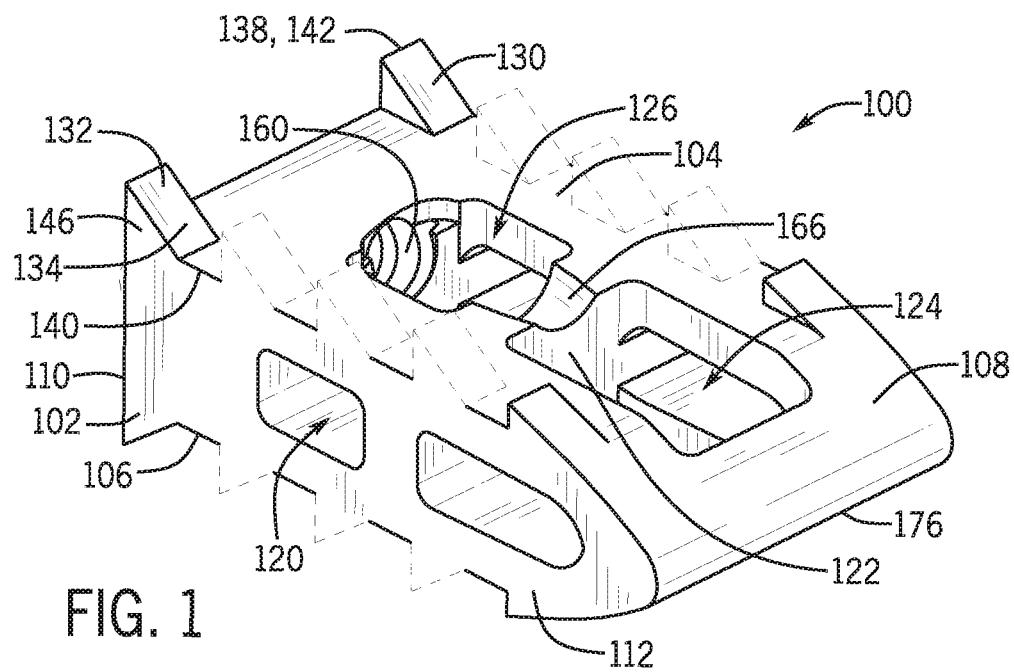
FIG. 1 is a front perspective view of a spinal implant device in accordance with an embodiment of the present disclosure.

Aspects of the present disclosure generally involve devices and methods for treating spinal stenosis, or the narrowing of one or more areas of the intervertebral joint space between two adjacent vertebrae. This narrowing can put pressure on the spinal cord or the nerves that branch out from the narrowed area, thus causing pain, tingling, numbness and/or weakness. As such, in one aspect, a spinal implant device is provided to remedy this condition by, for example, distracting and maintaining the distracted position of the affected spinal facet joint. For instance, the implant may be inserted and secured within the spinal facet joint to forcibly separate adjacent vertebrae. This approach may allow for maintaining the distraction of the joint, thereby relieving symptoms associated with spinal stenosis.

Some embodiments described herein are related to an implant device and system for use in spinal joint fusion procedures. Generally, the implant is used in spinal fusions performed by minimally invasive posterior access into a facet joint of the cervical spine. In some examples, the spinal implant may be formed by a thin implant shell having attachment or fixation or engagement members, such as teeth or serration features. The implant shell may also include openings or apertures or holes which promote bone growth and, ultimately, fusion. The spinal implant further includes a graft or allograft core which is received, or matingly received, in the implant shell to form the spinal implant. The graft core may be formed or sized to fit within the implant shell and is retained therein by a friction fit and/or a spring force provided by the shell or by interference. Other potential methods for attaching the graft core to the implant shell include using an implantable (e.g., biocompatible) adhesive, high-friction surface on an inner surface of the implant shell, e.g. titanium plasma spray or the like.

In one aspect, the improved implant provides an allograft (bone graft) core and a shell having fixation members, such as teeth. The shell has selective radiopacity and can be visualized with X-ray or other imaging technique thereby allowing a practitioner to ensure proper placement and confirm that the implant has not moved after placement. The fixation structures promote retention of the implant in the spinal joint and limit micromotion and implant migration. Preventing implant motion immediately post-implantation is helpful in promoting fusion. The allograft core provides structural support with biomechanical properties similar to those of the surrounding bone. In addition, the allograft core promotes new bone growth (osteoconduction) and fusion.

In some examples, the spinal implant is made up of two members which are assembled prior to implantation into the facet joint. In other examples the spinal implant may be assembled in situ during the procedure. For example, the implant shell may be inserted into the target location using an insertion tool with features, such as arms, that keep the shell in an open position. The graft core may then be inserted into an insertion tool lumen and pushed into the implant shell in situ. The insertion tool may then be removed, leaving the implant shell and graft core in place. Examples disclosed herein also include a method of using any of the spinal implants disclosed herein.

Some of the devices, systems, and methods described herein may include, be performed using, or be similar to, one or more components of the DTRAX® Spinal System, from Providence Medical Technology, Inc. (www.providencemt.com). Various components of the DTRAX® Spinal System may be modified or adjusted, according to various embodiments, for uses described herein.

Figure 56:
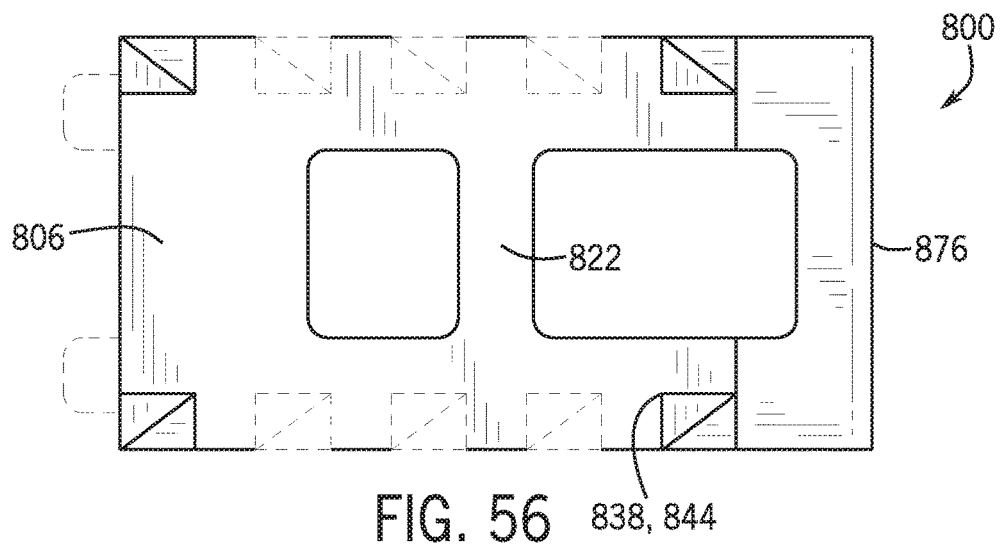
FIG. 56 is a bottom plan view of the spinal implant device of FIG. 50 in accordance with an embodiment of the present disclosure.

Turning now to the figures, FIGS. 1-56 illustrate various embodiments of a spinal implant operable to fixedly engage two adjacent vertebrae of a spinal facet joint to fuse the two adjacent vertebrae together (e.g., vertebrae of the human cervical spine, such as the C5 and C6 vertebrae). Referring to FIGS. 1-7, a spinal implant 100 according to one embodiment of the present disclosure includes a main body 102 defined by opposing top and bottom surfaces 104, 106, opposing front and rear surfaces 108, 110, and opposing side surfaces 112. In some embodiments, the majority of the surfaces (e.g., the opposing top and bottom surfaces 104, 106, the rear surface 110, and the opposing side surfaces 112) may be planar. As such, the implant 100 may be generally cuboid in shape, though other shapes are contemplated that permit the implant 100 to be inserted within a spinal facet joint and maintain a certain distance between two adjacent vertebrae. As described in more detail below, the spinal implant 100, which may be formed of a bone or bone substitute material or a biocompatible metal, ceramic, polymer, or some combination thereof, may be sized and shaped to fit snugly (e.g., through friction fit) into or otherwise engage or abut adjacent vertebrae of the spinal facet joint.

To reduce weight and offer cross-sectional areas for new bone growth and fusion, for instance, the implant 100 may include one or more windows 120 defined in at least one surface of the main body 102. For example without limitation, the implant 100 of FIGS. 1-7 includes two windows 120 defined in each of the top, bottom, and opposing side surfaces 112 of the main body 102, though any number of windows 120 is contemplated. In such embodiments, the implant 100 may include an interior wall 122 positioned within the main body 102 to define a portion of at least two windows 120. In embodiments having two windows 120 defined in each of the top, bottom, and opposing side surfaces 104, 106, 112 of the main body 102, the interior wall 122 may define a portion of each window 120. The windows 120 may be any size, shape, and orientation. For instance, in the embodiments of FIGS. 1-7, each of the windows 120 of a respective surface of the main body 102 is generally rectangular and arranged end to end along a midline of the respective surface. As shown, each of the windows 120 is adapted to place a hollow interior of the implant 100 in communication with the surrounding environment. In such embodiments, the hollow interior of the implant 100 may include one or more chambers, such as a distal chamber 124 separated from a proximal chamber 126 by the interior wall 122. To permanently fuse adjacent vertebrae together, the chambers 124, 126 may by packed (via the windows 120, for instance) with a bone or bone substitute material to cause bone ingrowth into the hollow interior of the implant 100. As shown, one of the chambers 124, 126 may be larger than the other, such as the distal chamber 124 being larger than the proximal chamber 126. In other embodiments, the chambers 124, 126 have equal dimensions or are the same size.

With continued reference to FIGS. 1-7, the implant 100 may include at least one retaining feature 130 associated with at least one surface of the main body 102 to frictionally engage the implant 100 within a spinal facet joint. For instance, the implant 100 may include a plurality of protrusions 132 extending away from at least one of the opposing top and bottom surfaces 104, 106 of the main body 102 (e.g., from both the top and bottom surfaces 104, 106). As described herein, the protrusions 132, which may be referred to as teeth, may be operable to permit the implant 100 to be inserted into a spinal facet joint but may also limit its removal therefrom. For example, the protrusions 132 may be directionally sized and shaped such that a force required to remove the implant 100 from the spinal facet joint is substantially greater than a force required to insert the implant 100 within the facet joint. In this manner, the implant 100 may be inserted into proper position within the facet joint as desired. Once inserted, the protrusions 132 may limit movement of the implant 100 within the facet joint in at least the removal direction. In some embodiments, the protrusions 132 may be operable to limit lateral movement of the implant 100 within the facet joint, as explained below.

Figure 2:
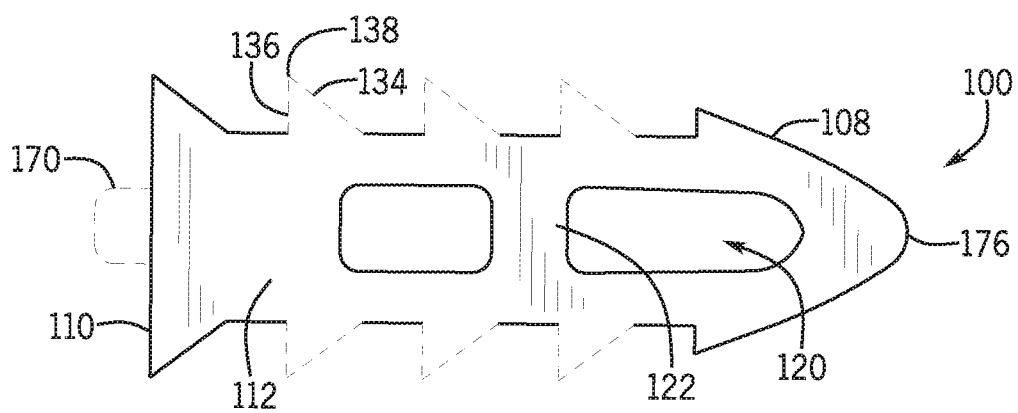
FIG. 2 is a left elevation view of the spinal implant device of FIG. 1 in accordance with an embodiment of the present disclosure.
Figure 3:
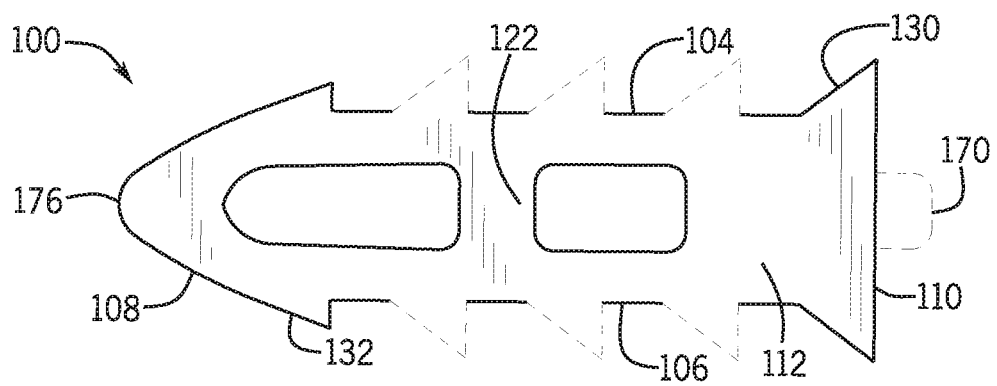
FIG. 3 is a right elevation view of the spinal implant device of FIG. 1 in accordance with an embodiment of the present disclosure.
Figure 23:
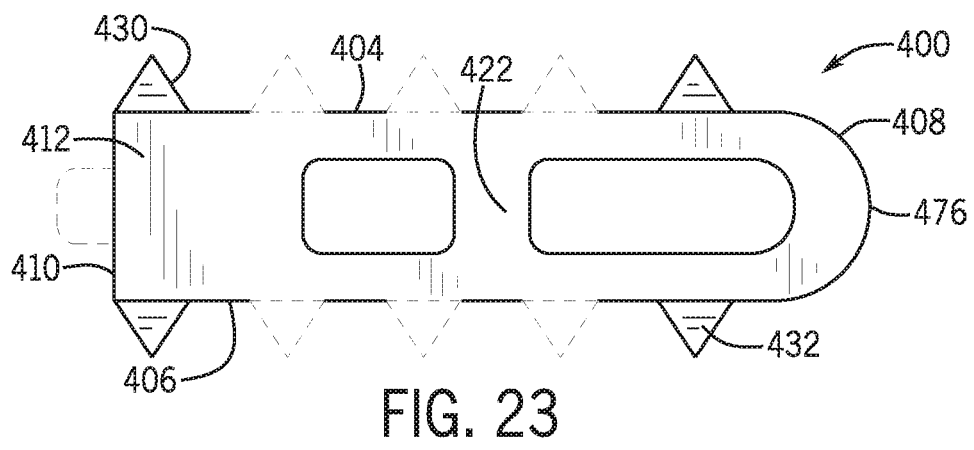
FIG. 23 is a left elevation view of the spinal implant device of FIG. 22 in accordance with an embodiment of the present disclosure.
Figure 24:
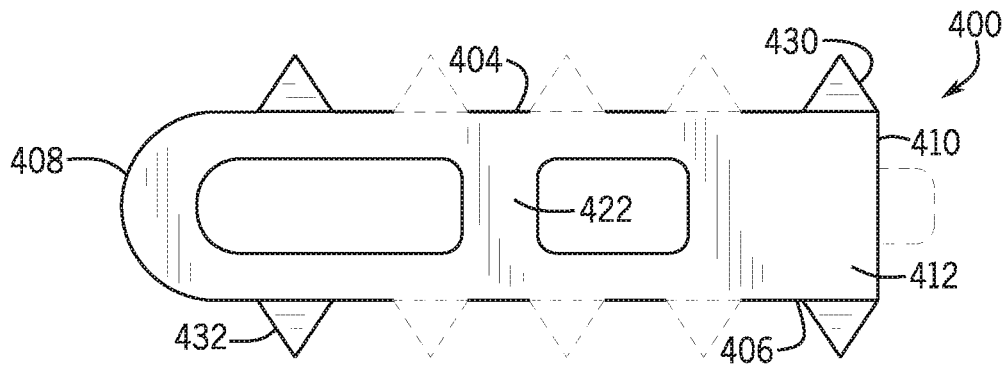
FIG. 24 is a right elevation view of the spinal implant device of FIG. 22 in accordance with an embodiment of the present disclosure.
Figure 25:
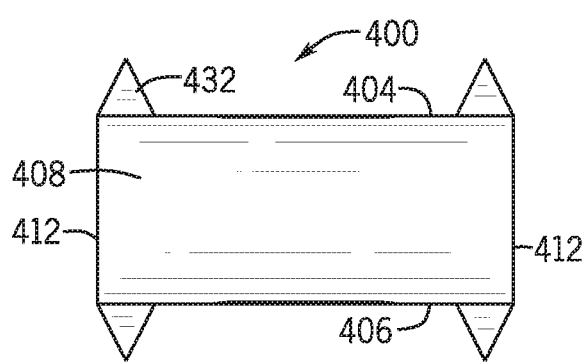
FIG. 25 is a front elevation view of the spinal implant device of FIG. 22 in accordance with an embodiment of the present disclosure.
Figure 26:
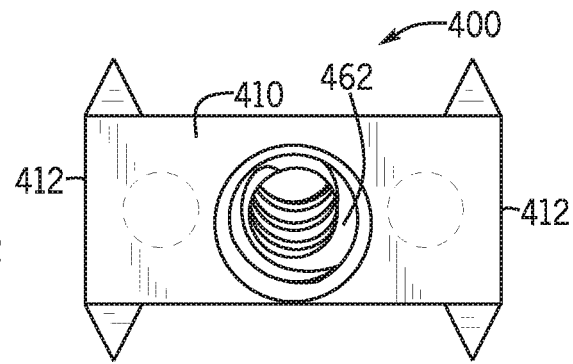
FIG. 26 is a rear elevation view of the spinal implant device of FIG. 22 in accordance with an embodiment of the present disclosure.
Figure 27:
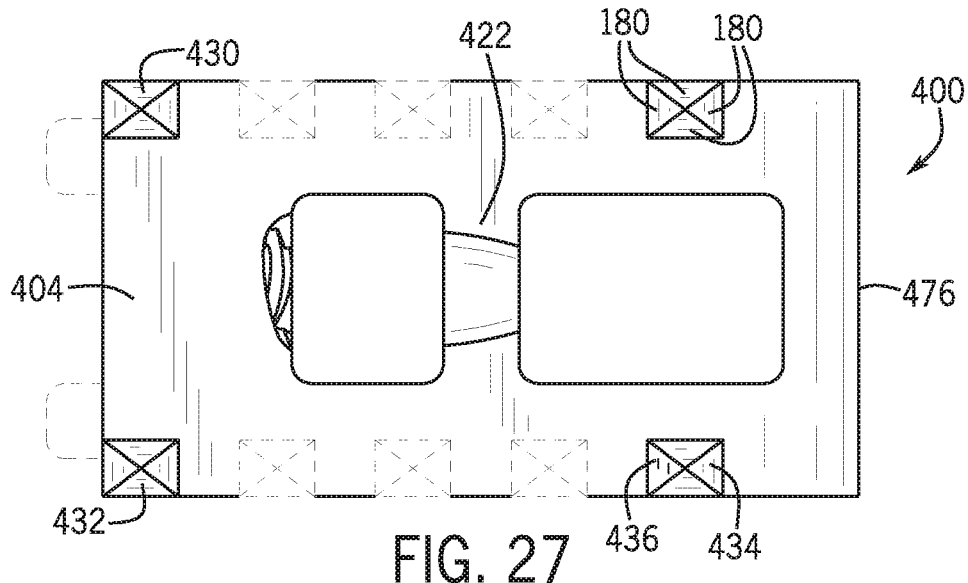
FIG. 27 is a top plan view of the spinal implant device of FIG. 22 in accordance with an embodiment of the present disclosure.
Figure 28:
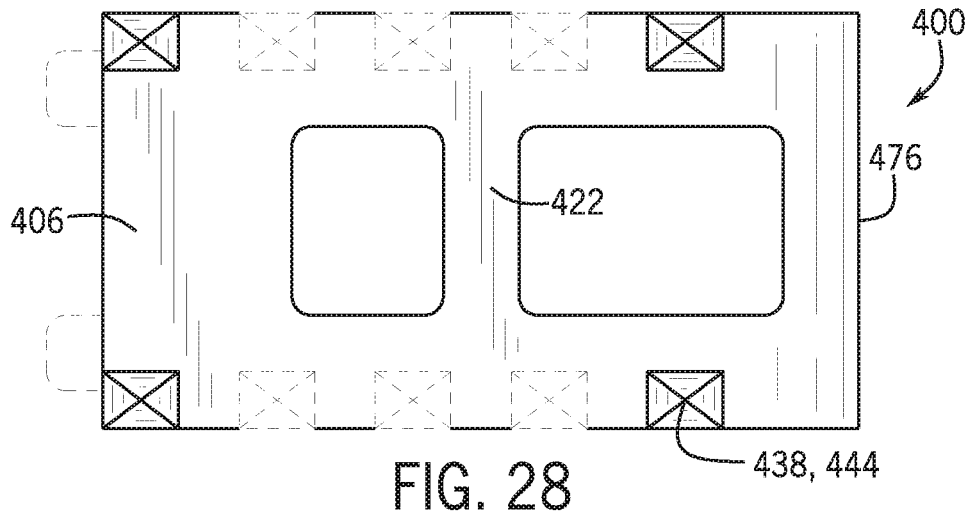
FIG. 28 is a bottom plan view of the spinal implant device of FIG. 22 in accordance with an embodiment of the present disclosure.
Figure 29:
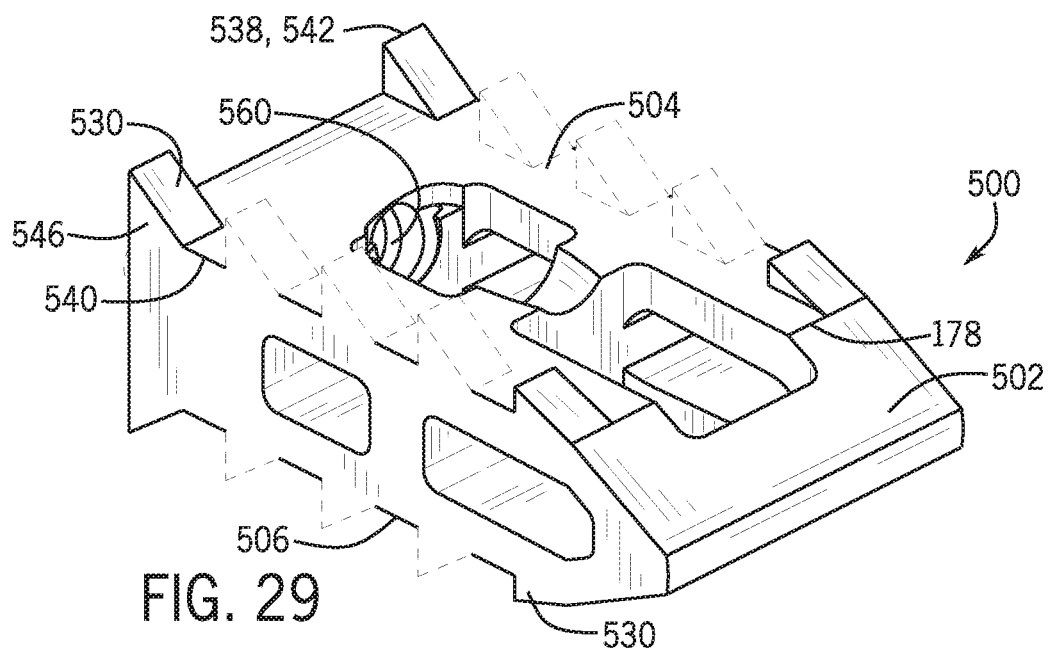
FIG. 29 is a front perspective view of an additional embodiment of a spinal implant device in accordance with an embodiment of the present disclosure.

As shown in FIGS. 1-3, each of the protrusions 132 may include a leading face 134, a trailing face 136, and a tip 138 formed at an intersection between the leading and trailing faces 134, 136. In some embodiments, the protrusions 132 may extend from adjacent (e.g., at or near) an edge 140 defined between the opposing top and bottom surfaces 104, 106 and the opposing side surfaces 112. In such embodiments, each of the top and bottom surfaces 104, 106 may include two rows of protrusions 132 extending between the front and rear surfaces 108, 110 and adjacent (e.g., along) opposing edges 140 of the respective surface, the windows 120 being positioned between the rows of protrusions 132. As shown in FIG. 2, each row of protrusions 132 may include a sawtooth profile, though other profile shapes are contemplated including triangle (see FIG. 23), square, and sinusoidal, among others.

Figure 8:
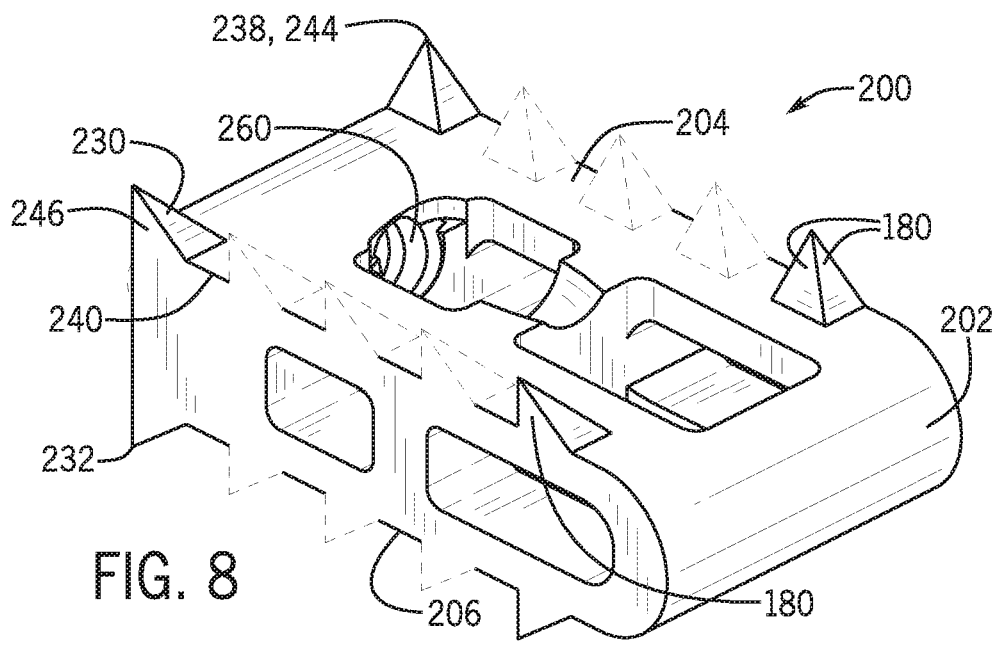
FIG. 8 is a front perspective view of an additional embodiment of a spinal implant device in accordance with an embodiment of the present disclosure.

The protrusions 132 may be variously sized and shaped depending on the particular application. For example without limitation, the trailing face 136 may include a slope that is different than a slope of the leading face 134. In one embodiment, the trailing face 136 may include a slope that is greater than a slope of the leading face 134. For instance, the slope of the trailing face 136 may be approximately 90° such that the trailing face 136 extends substantially perpendicular from the top and bottom surfaces 104, 106 of the main body 102. In the embodiments of FIGS. 1-7, the tip 138 is a ridge 142 extending a width of the protrusion, such as the entire width of the associated protrusion. Though FIGS. 1-7 show a ridge 142, as explained below, the tip 138 may take on other shapes and configurations, such as a point 244 (see FIG. 8, for instance), a truncated flat surface, or the like, depending on a desired aesthetic and/or functional characteristic. In each of the embodiments described herein, however, the shape and configuration of the protrusions 132 permit the implant 100 to be inserted within a facet joint while also resisting pullout. For example, the protrusions 132 may be configured such that the protrusions 132 engage into surrounding bone or tissue when the implant 100 is moved away from the facet joint, such as in the removal direction. In some embodiments, the protrusions 132 may be shaped such that the protrusions 132 also engage into surrounding bone or tissue when the implant 100 is moved laterally within the facet joint. In such embodiments, the protrusions 132 may include a lateral face 146 extending from the top or bottom surfaces 104 or 106, such as substantially parallel to at least one of the opposing side surfaces 112. As shown in FIGS. 1 and 5, the lateral face 146 in one embodiment may be coplanar with one of the opposing side surfaces 112 to provide the resistance necessary to limit lateral movement within the facet joint.

In addition to the description above, the protrusions 132 may be variously sized and shaped in other ways. For instance, the height of the protrusions 132 (as defined by the tips 138) may be uniform or may vary along the length of the implant 100 between the front and rear surfaces 108, 110 of the main body 102. For instance, the protrusions 132 positioned nearer the front surface 108 of the main body 102 may have a smaller height than the protrusions 132 positioned away from the front surface 108 (see FIG. 2), or vice-versa. Similarly, the distance between the protrusions 132 may be uniform or may vary along the length of the implant 100. For instance, the distance between the protrusions 132 positioned nearer the front surface 108 may be less than the distance between the protrusions 132 positioned nearer the rear surface 110, or vice-versa.

Figure 61A:
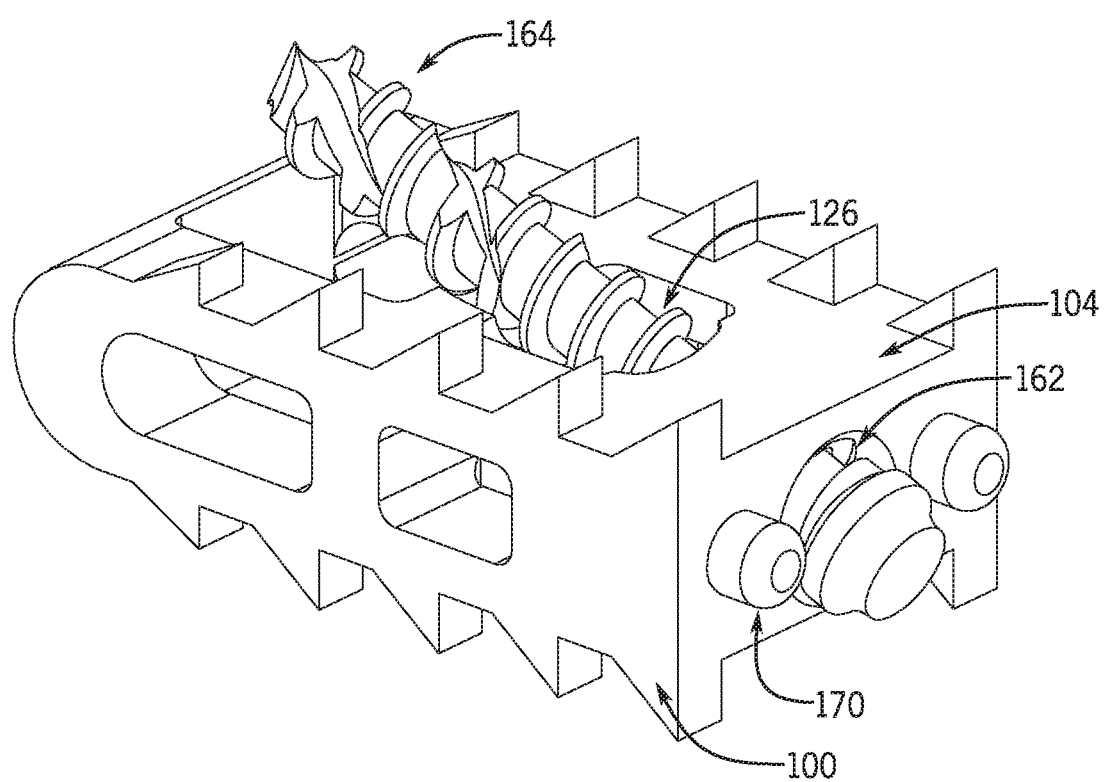
FIGS. 61A-61C depict a spinal implant device with a bone screw in accordance with an embodiment of the present disclosure.
Figure 61B:
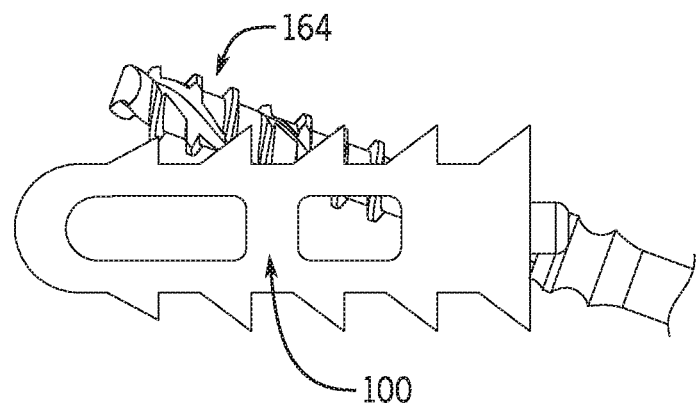
Figure 61C:
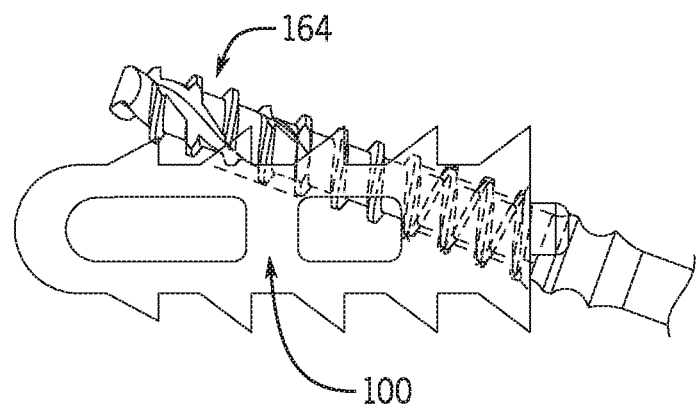

Referring now to FIGS. 1-7, the implant 100 may include at least one securement feature 160 associated with at least one surface of the main body 102 to fixedly secure the implant 100 within the spinal facet joint. For instance, a securement aperture 162 may be defined in the main body 102 (e.g., in at least the rear surface 110 of the main body 102), the securement aperture 162 operable to receive a fastener therein, such as a bone screw 164 (see FIGS. 61A-61C). As shown, the securement aperture 162 may be angled such that the bone screw 164 extends through the rear surface 110 and one of the top and bottom surfaces 104, 106 (e.g., through the top surface 104) of the main body 102 to engage an adjacent vertebra. To secure the implant 100 within the facet joint, the securement aperture 162 may be angled so the bone screw 164 inserted therein extends upwardly to engage an upper vertebra, though the opposite may be true depending on the particular application. In this manner, the implant 100 may be inserted within a patient's facet joint irrespective of the relative positions of the top and bottom surfaces 104, 106. In the embodiments described herein, the securement aperture 162 may be configured such that the bone screw 164 extends through the proximal chamber 126 and through at least one window 120 defined in the top surface 104 or the bottom surface 106 of the main body 102. As best seen in FIG. 1, depending on the size of the windows 120 as well as the angle of the securement aperture 162, the interior wall 122 may include a notch 166 to at least accommodate the bone screw 164 to be inserted within the implant 100. In other embodiments, the securement aperture 162 may be a straight, non-angled securement aperture. In other embodiments, the securement aperture 162 may be a longitudinal, non-angled securement aperture. The bone screw 164 described herein may be made of any suitable material, including biocompatible metals, ceramics, and/or polymers. In some embodiments, the bone screw 164 may be a DTRAX® Bone Screw-A from Providence Medical Technology, Inc.

Turning to FIGS. 2 and 5-7, the implant 100 may include other features for convenience. For example, the implant 100 in one embodiment may include one or more posts 170 (e.g., two posts 170) extending from the rear surface 110 of the implant 100. In such embodiments, the posts 170 may be operable to properly position the implant 100 within a facet joint, such as through engagement with other portions or members of a distraction system. For example, the posts 170 may be operable to engage a delivery device, such as the delivery devices shown in FIGS. 57-60) such that the delivery device can position the implant 100 within a patient's facet joint. For example, the posts 170 may be received within corresponding apertures defined in the delivery device to align and/or couple the implant 100 to the delivery device, as more fully explained below. As shown in FIG. 5, the posts 170 extend from the rear surface 110 of the implant 100 in a laterally spaced relationship. In such embodiments, the securement aperture 162 may be defined within the rear surface 110 between the two posts 170.

Figure 9:
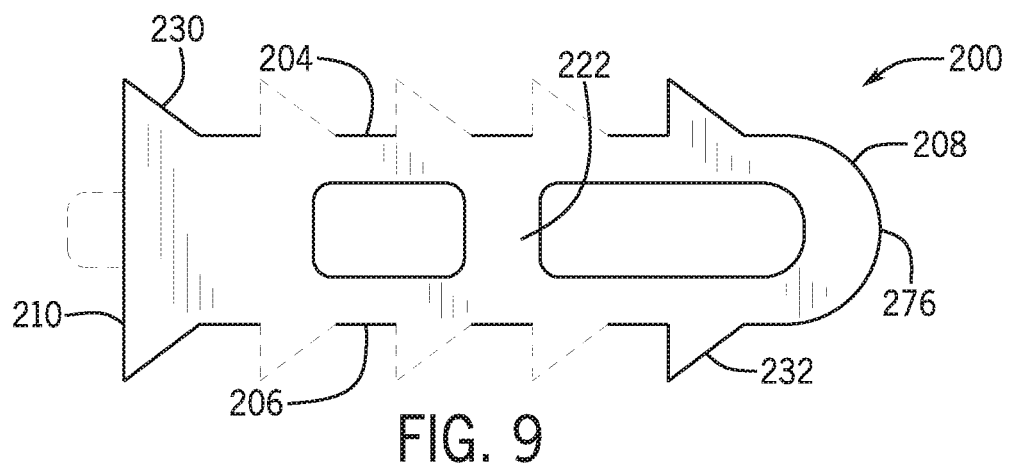
FIG. 9 is a left elevation view of the spinal implant device of FIG. 8 in accordance with an embodiment of the present disclosure.
Figure 10:
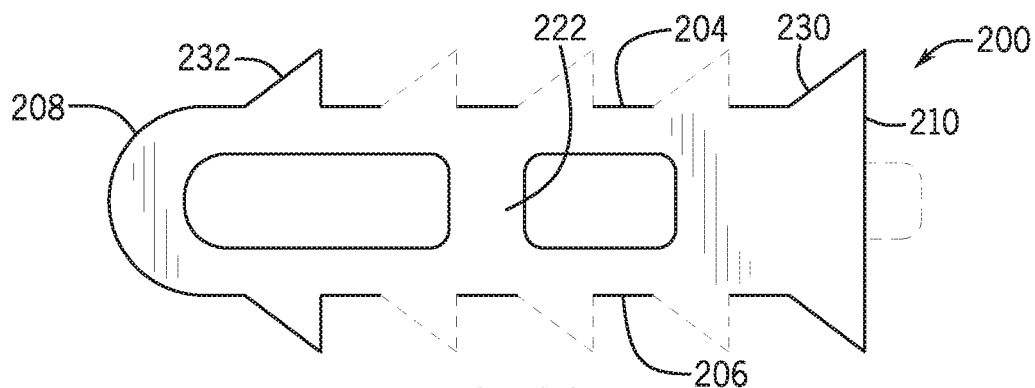
FIG. 10 is a right elevation view of the spinal implant device of FIG. 8 in accordance with an embodiment of the present disclosure.
Figure 11:
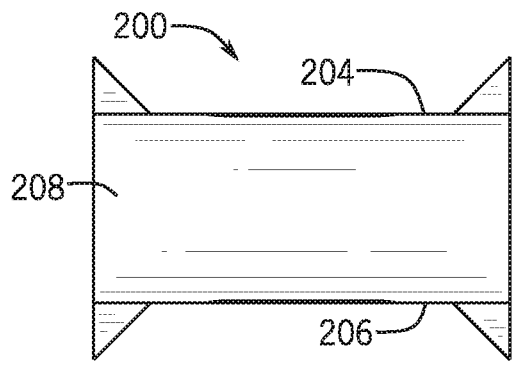
FIG. 11 is a front elevation view of the spinal implant device of FIG. 8 in accordance with an embodiment of the present disclosure.
Figure 12:
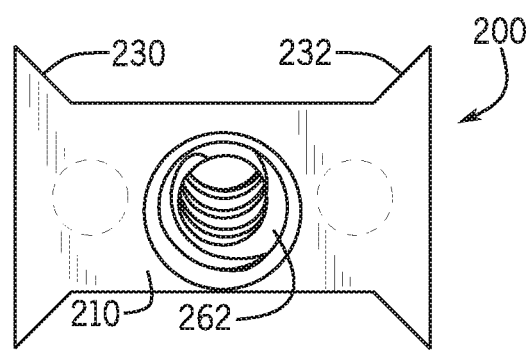
FIG. 12 is a rear elevation view of the spinal implant device of FIG. 8 in accordance with an embodiment of the present disclosure.
Figure 13:
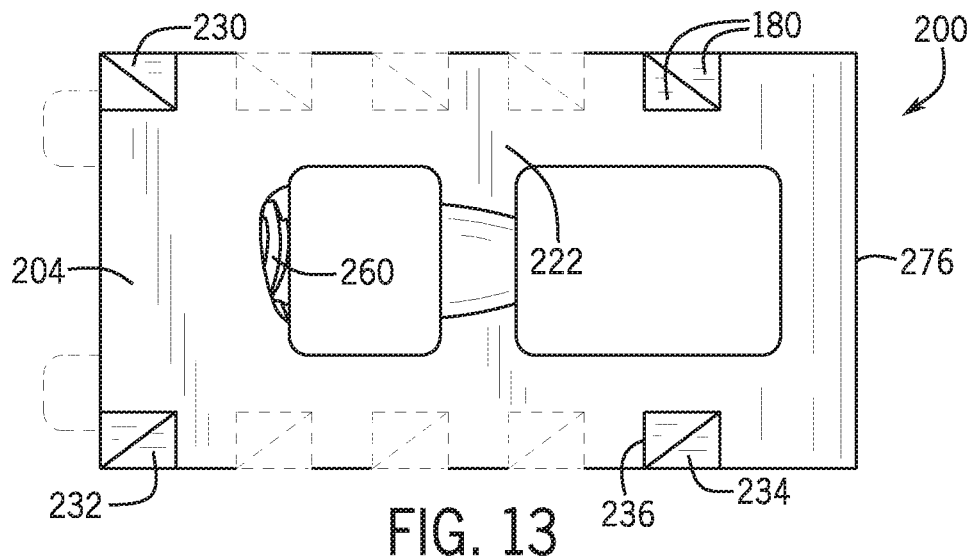
FIG. 13 is a top plan view of the spinal implant device of FIG. 8 in accordance with an embodiment of the present disclosure.
Figure 14:
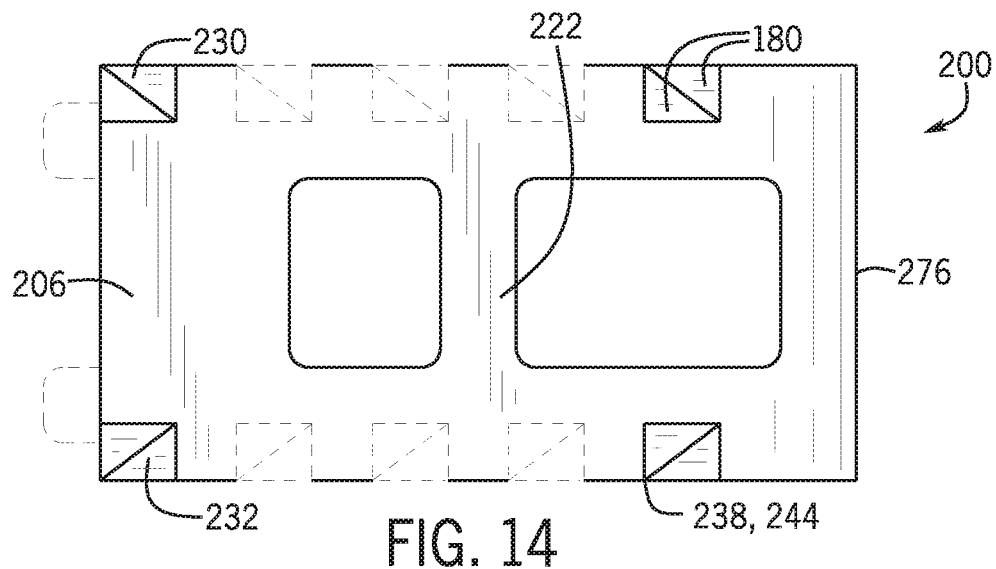
FIG. 14 is a bottom plan view of the spinal implant device of FIG. 8 in accordance with an embodiment of the present disclosure.
Figure 15:
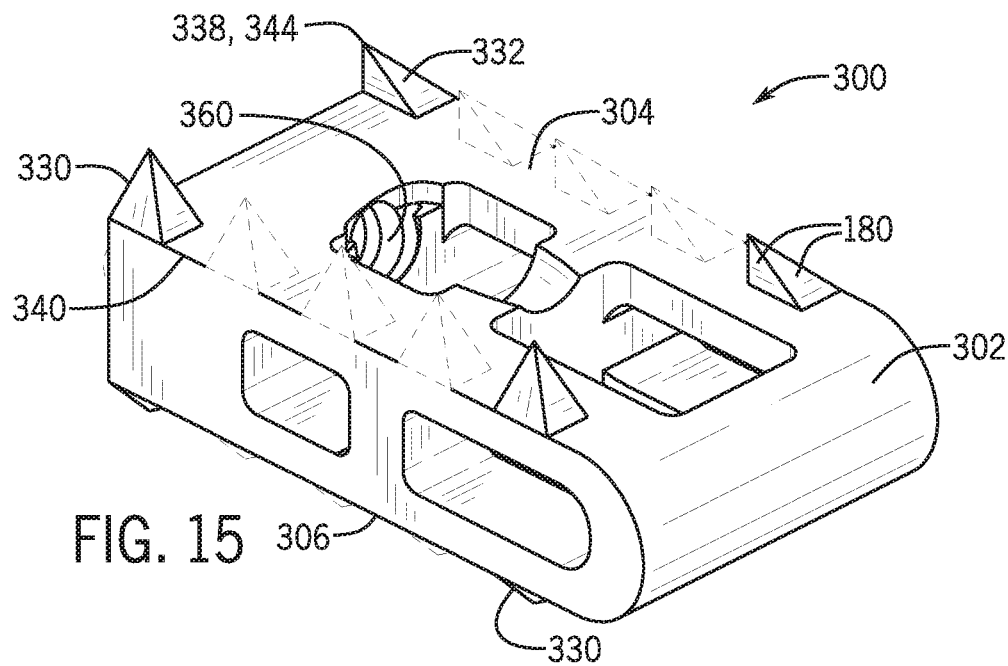
FIG. 15 is a front perspective view of an additional embodiment of a spinal implant device in accordance with an embodiment of the present disclosure.
Figure 16:
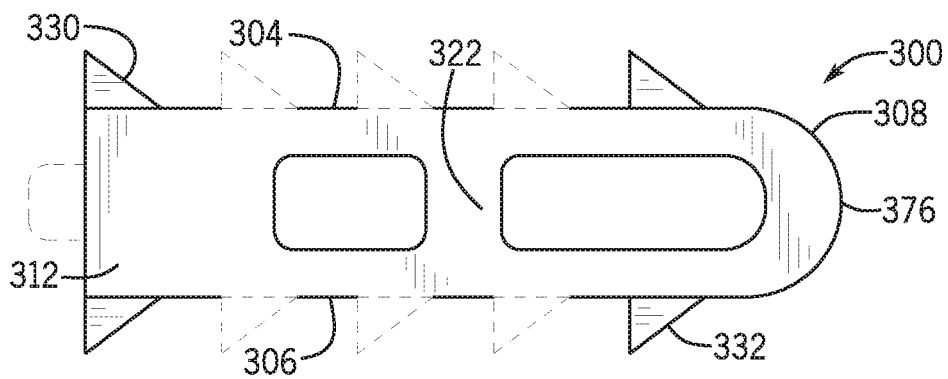
FIG. 16 is a left elevation view of the spinal implant device of FIG. 15 in accordance with an embodiment of the present disclosure.
Figure 17:
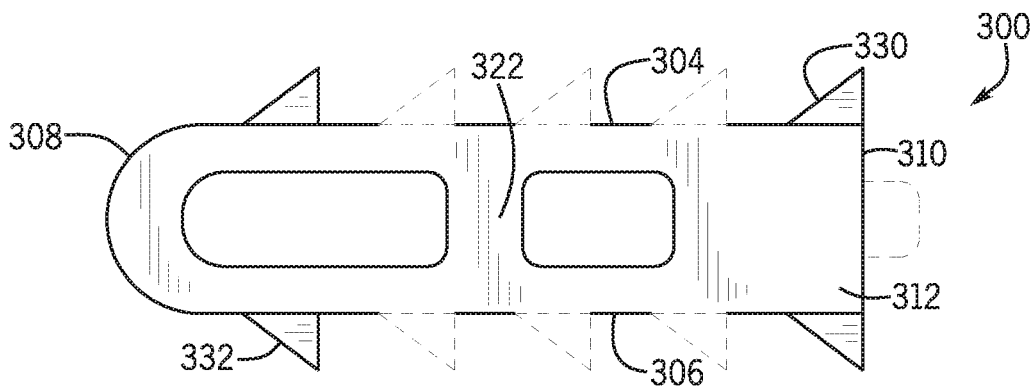
FIG. 17 is a right elevation view of the spinal implant device of FIG. 15 in accordance with an embodiment of the present disclosure.
Figure 18:
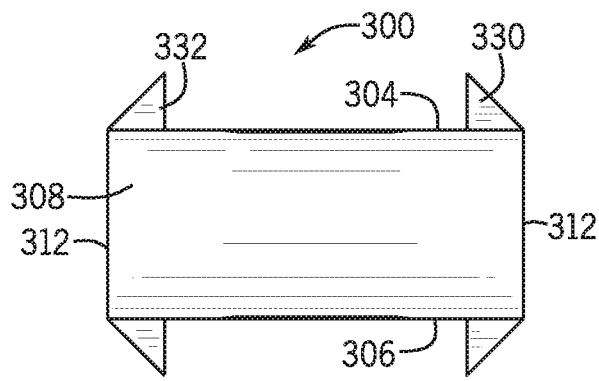
FIG. 18 is a front elevation view of the spinal implant device of FIG. 15 in accordance with an embodiment of the present disclosure.
Figure 19:
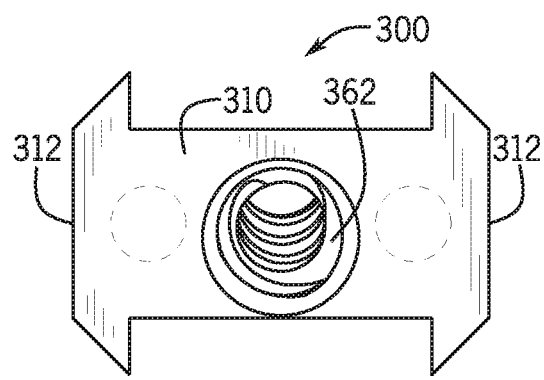
FIG. 19 is a rear elevation view of the spinal implant device of FIG. 15 in accordance with an embodiment of the present disclosure.
Figure 20:
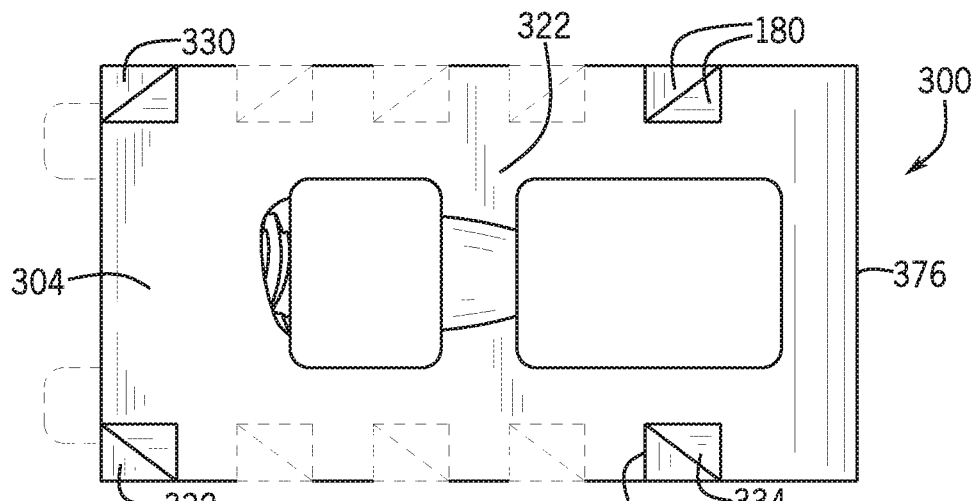
FIG. 20 is a top plan view of the spinal implant device of FIG. 15 in accordance with an embodiment of the present disclosure.
Figure 21:
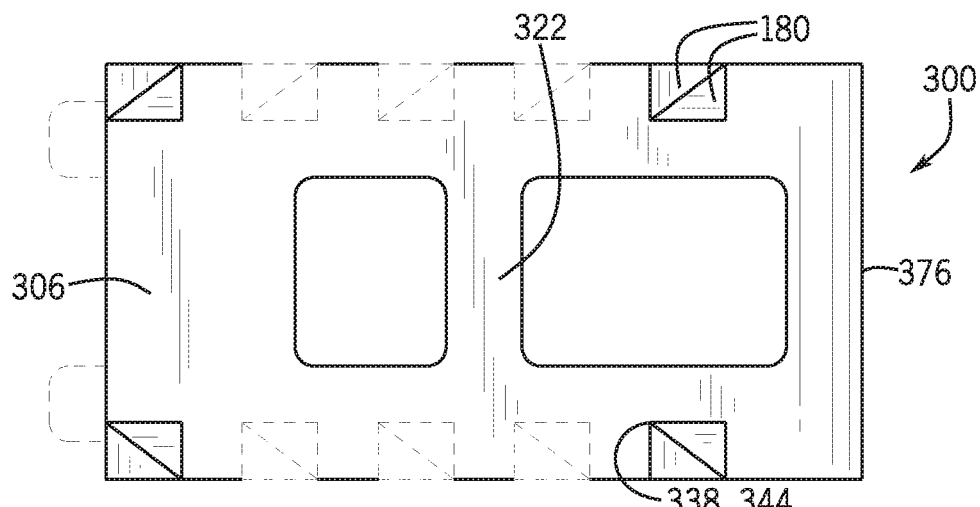
FIG. 21 is a bottom plan view of the spinal implant device of FIG. 15 in accordance with an embodiment of the present disclosure.
Figure 22:
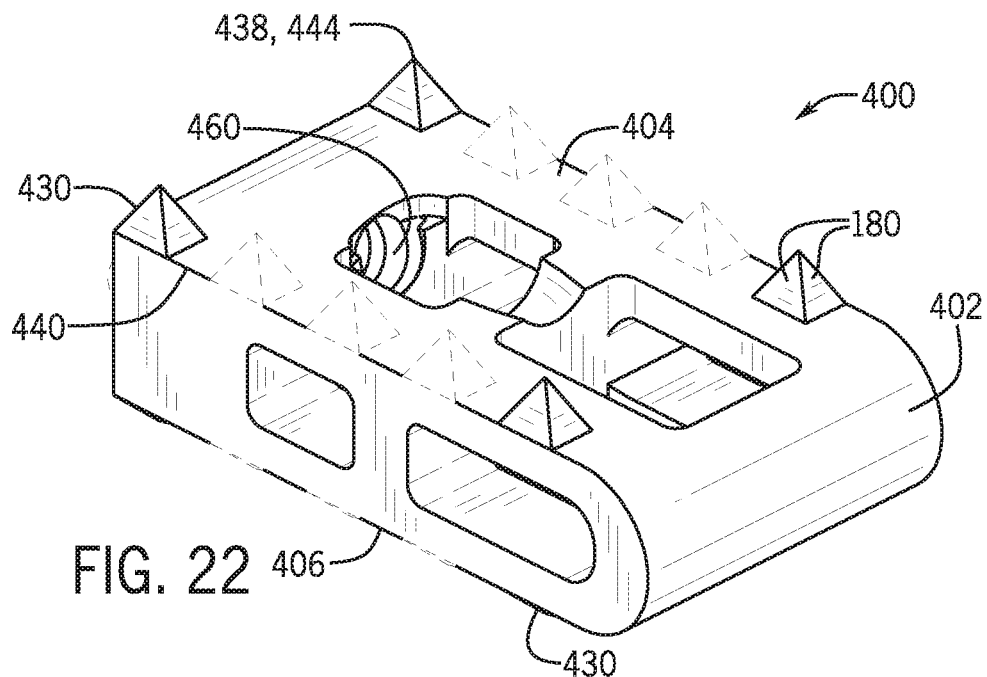
FIG. 22 is a front perspective view of an additional embodiment of a spinal implant device in accordance with an embodiment of the present disclosure.
Figure 30:
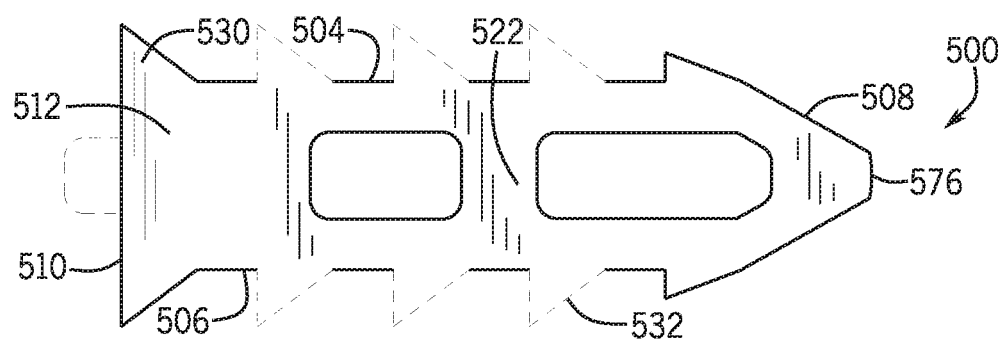
FIG. 30 is a left elevation view of the spinal implant device of FIG. 29 in accordance with an embodiment of the present disclosure.
Figure 31:
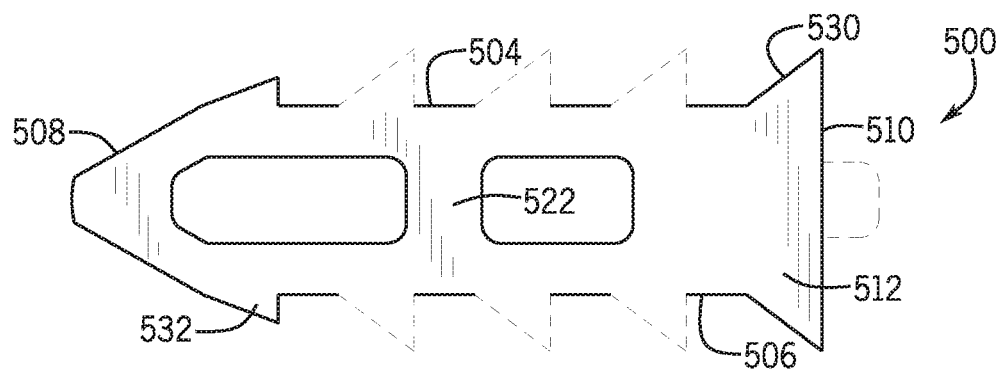
FIG. 31 is a right elevation view of the spinal implant device of FIG. 29 in accordance with an embodiment of the present disclosure.
Figure 32:
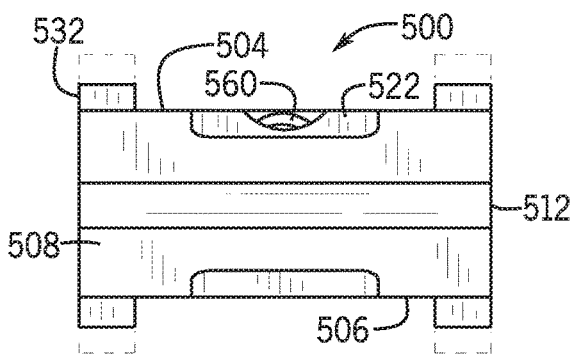
FIG. 32 is a front elevation view of the spinal implant device of FIG. 29 in accordance with an embodiment of the present disclosure.
Figure 33:
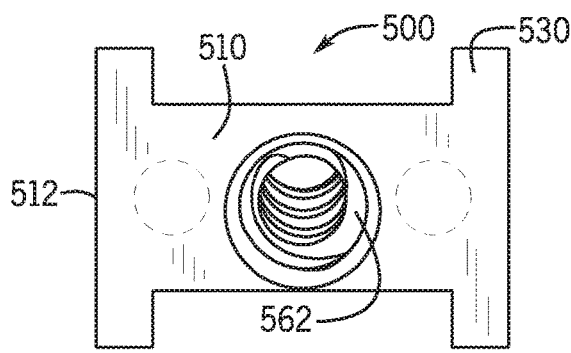
FIG. 33 is a rear elevation view of the spinal implant device of FIG. 29 in accordance with an embodiment of the present disclosure.
Figure 34:
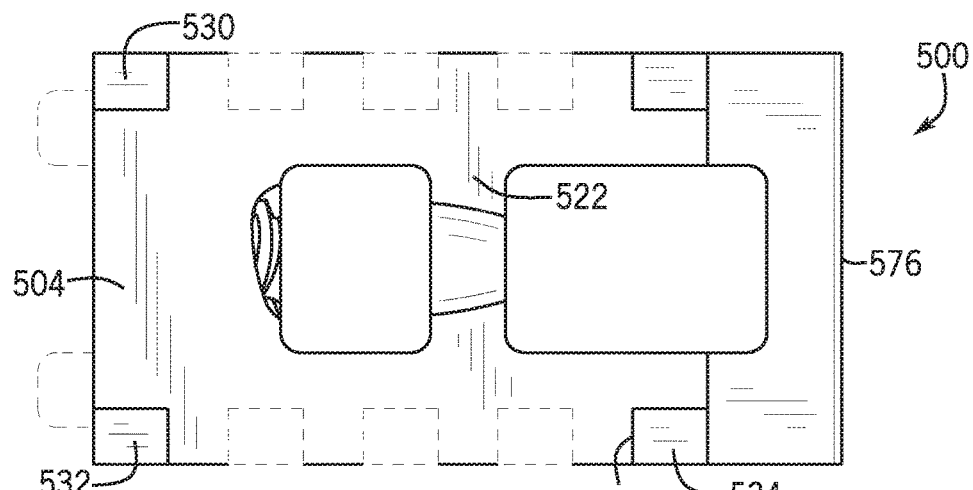
FIG. 34 is a top plan view of the spinal implant device of FIG. 29 in accordance with an embodiment of the present disclosure.
Figure 35:
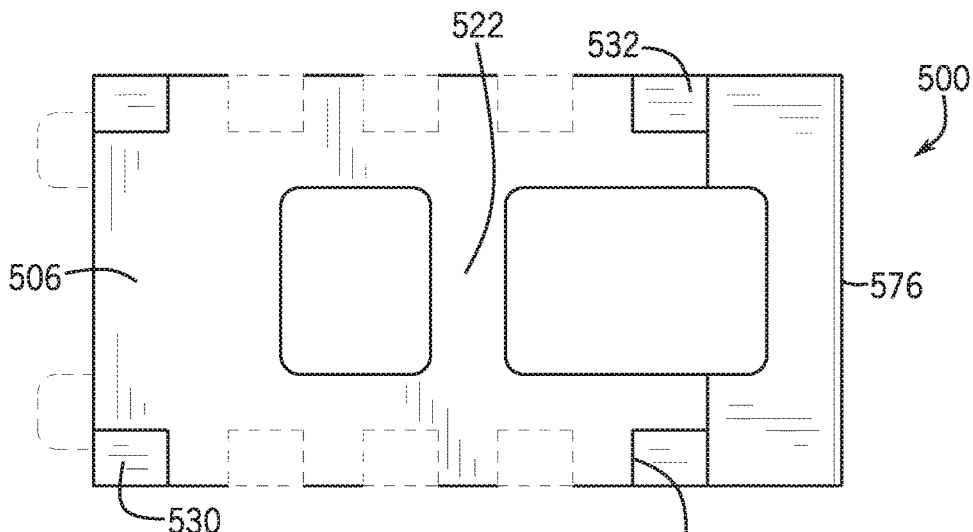
FIG. 35 is a bottom plan view of the spinal implant device of FIG. 29 in accordance with an embodiment of the present disclosure.
Figure 36:
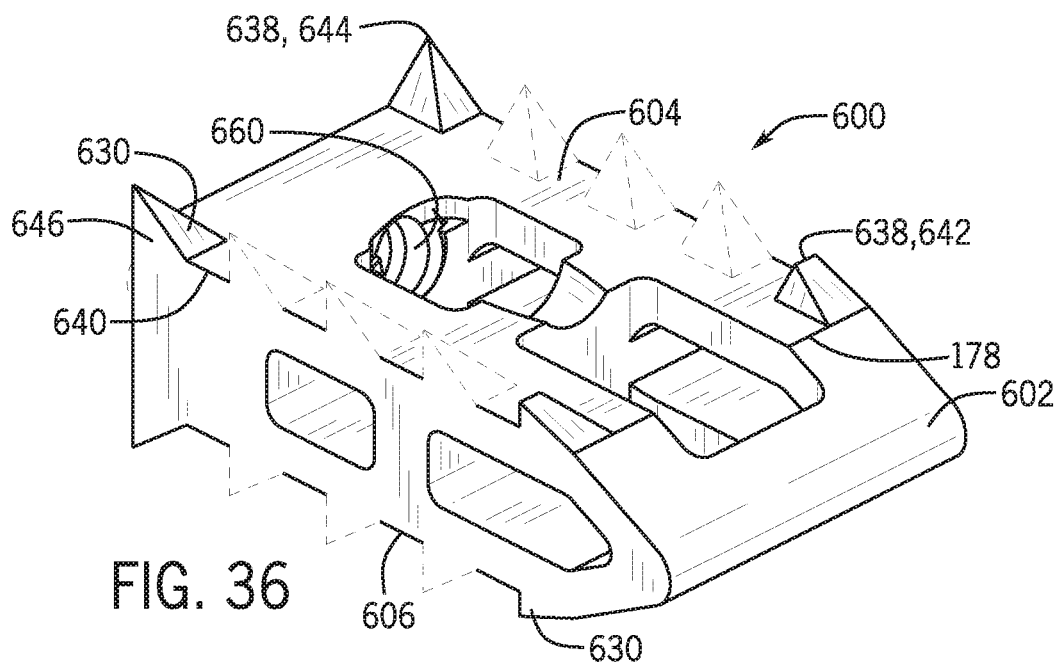
FIG. 36 is a front perspective view of an additional embodiment of a spinal implant device in accordance with an embodiment of the present disclosure.
Figure 37:
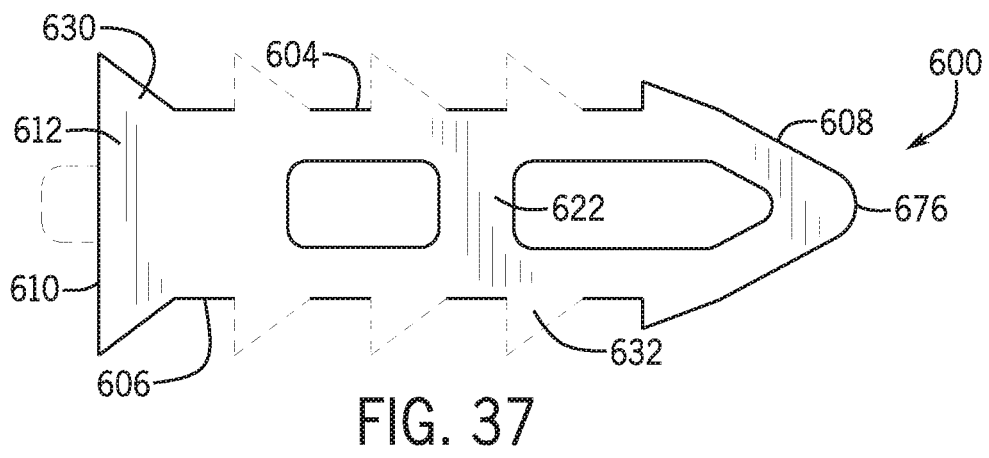
FIG. 37 is a left elevation view of the spinal implant device of FIG. 36 in accordance with an embodiment of the present disclosure.
Figure 38:
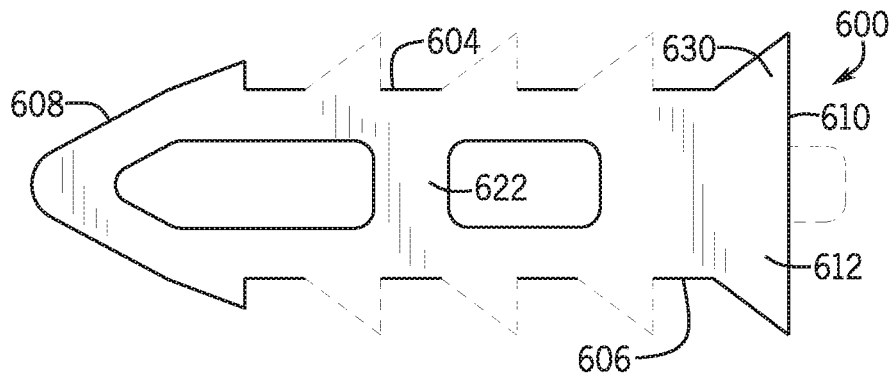
FIG. 38 is a right elevation view of the spinal implant device of FIG. 36 in accordance with an embodiment of the present disclosure.
Figure 39:
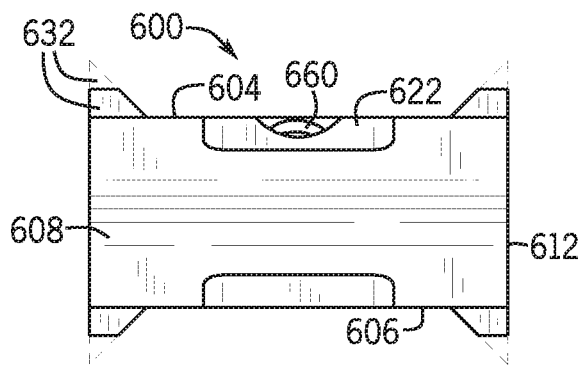
FIG. 39 is a front elevation view of the spinal implant device of FIG. 36 in accordance with an embodiment of the present disclosure.
Figure 40:
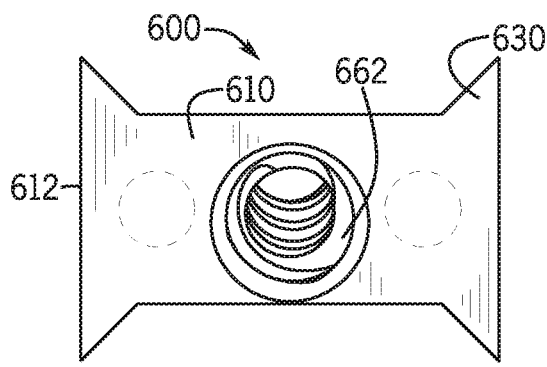
FIG. 40 is a rear elevation view of the spinal implant device of FIG. 36 in accordance with an embodiment of the present disclosure.
Figure 41:
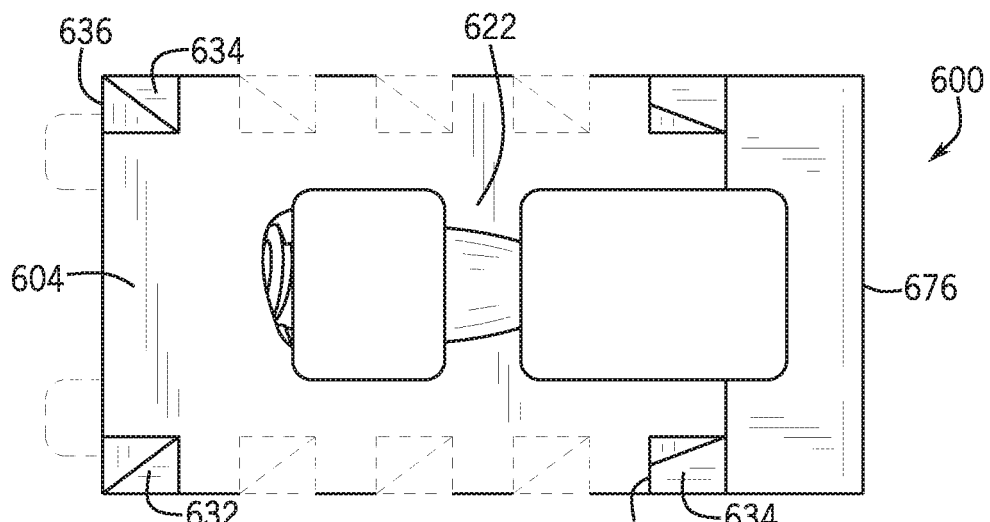
FIG. 41 is a top plan view of the spinal implant device of FIG. 36 in accordance with an embodiment of the present disclosure.
Figure 42:
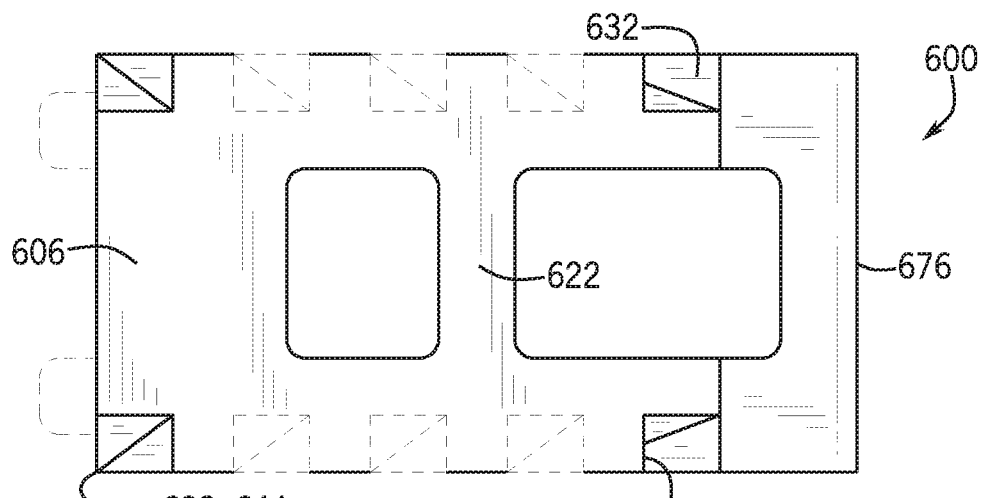
FIG. 42 is a bottom plan view of the spinal implant device of FIG. 36 in accordance with an embodiment of the present disclosure.
Figure 43:
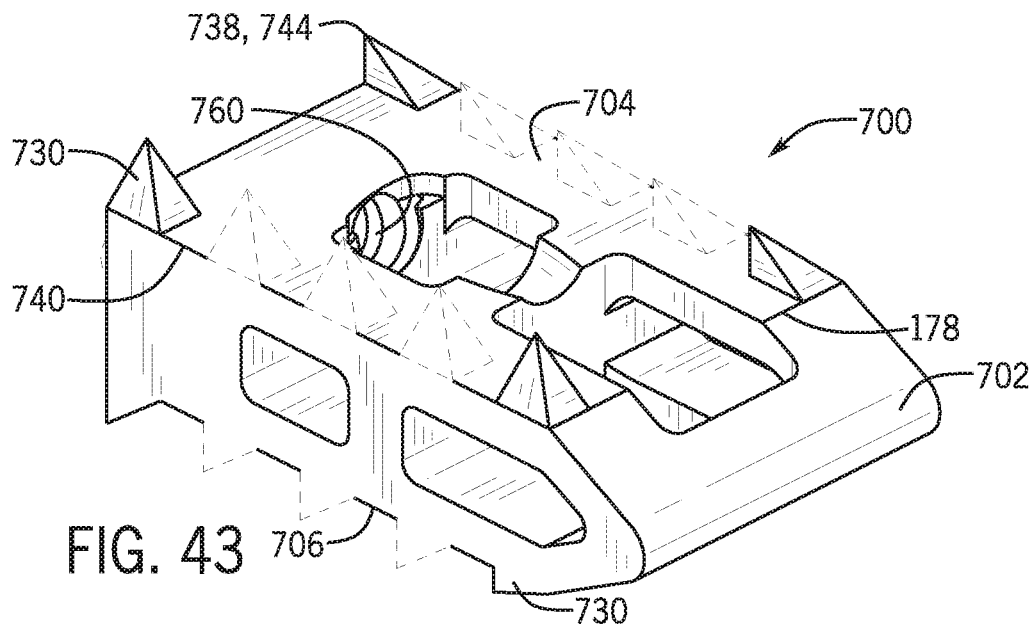
FIG. 43 is a front perspective view of an additional embodiment of a spinal implant device in accordance with an embodiment of the present disclosure.
Figure 44:
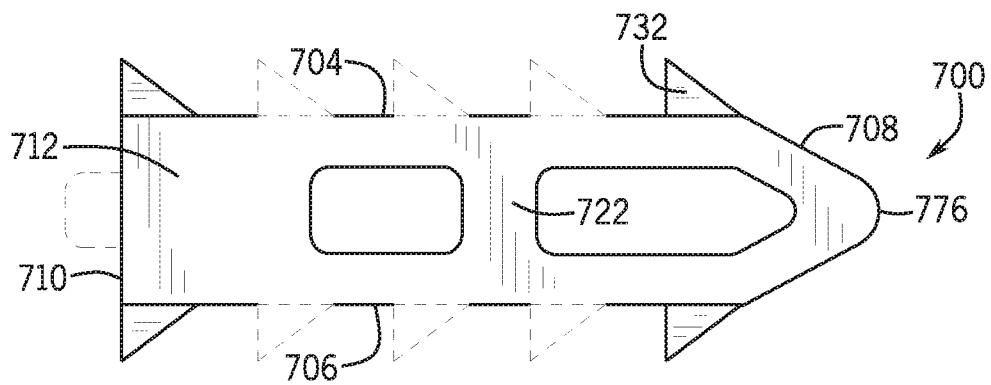
FIG. 44 is a left elevation view of the spinal implant device of FIG. 43 in accordance with an embodiment of the present disclosure.
Figure 45:
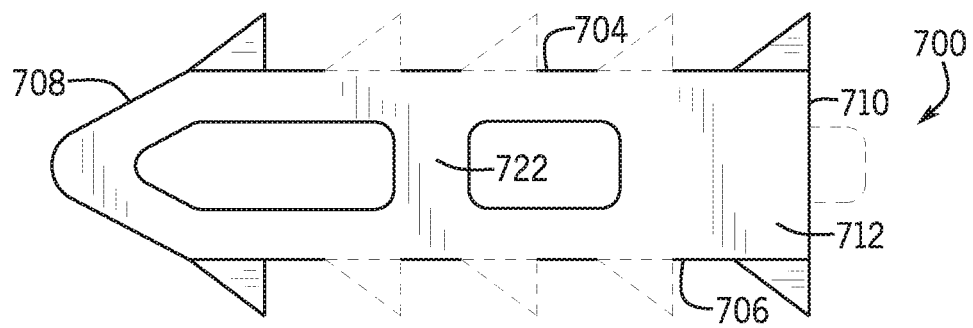
FIG. 45 is a right elevation view of the spinal implant device of FIG. 43 in accordance with an embodiment of the present disclosure.
Figure 46:
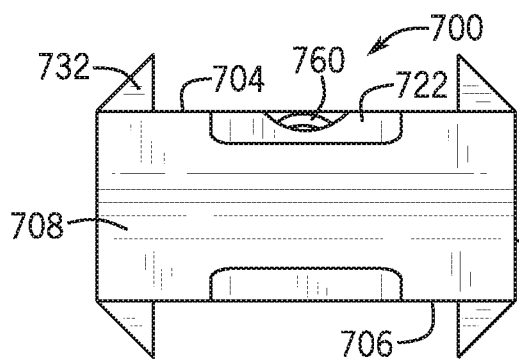
FIG. 46 is a front elevation view of the spinal implant device of FIG. 43 in accordance with an embodiment of the present disclosure.
Figure 47:
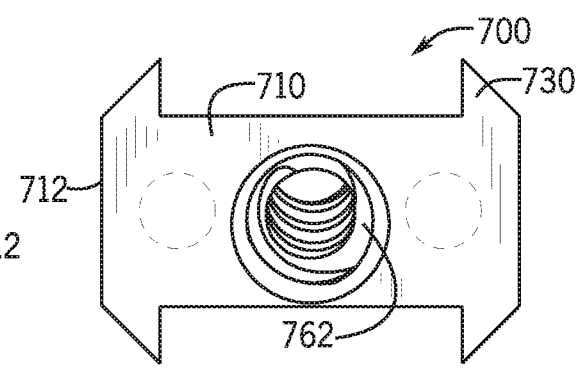
FIG. 47 is a rear elevation view of the spinal implant device of FIG. 43 in accordance with an embodiment of the present disclosure.
Figure 48:
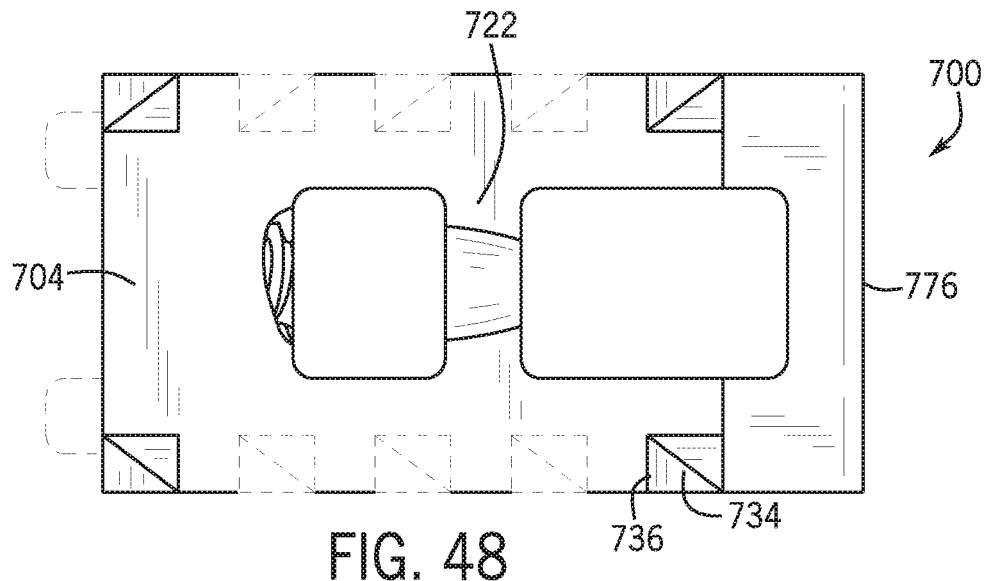
FIG. 48 is a top plan view of the spinal implant device of FIG. 43 in accordance with an embodiment of the present disclosure.
Figure 49:
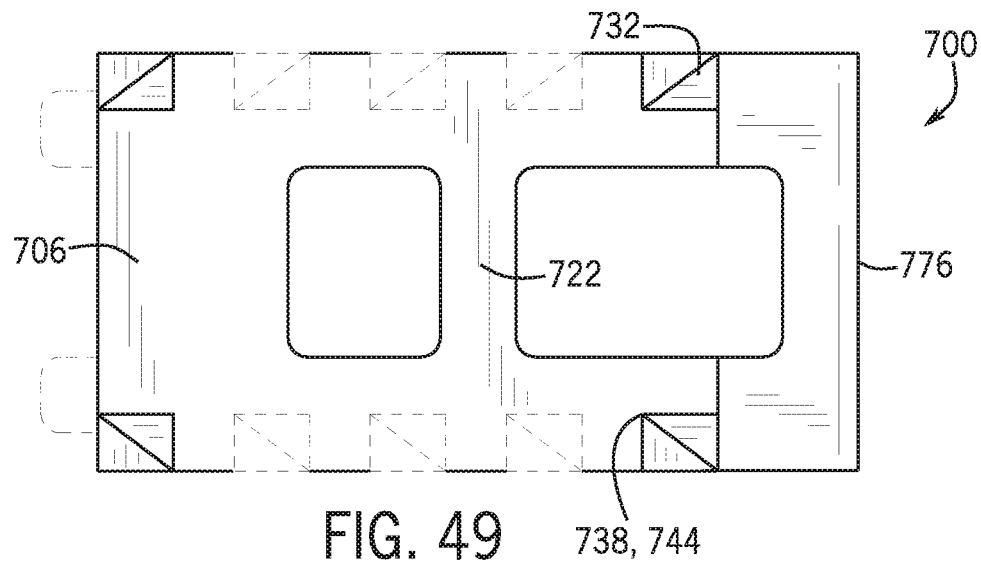
FIG. 49 is a bottom plan view of the spinal implant device of FIG. 43 in accordance with an embodiment of the present disclosure.
Figure 50:
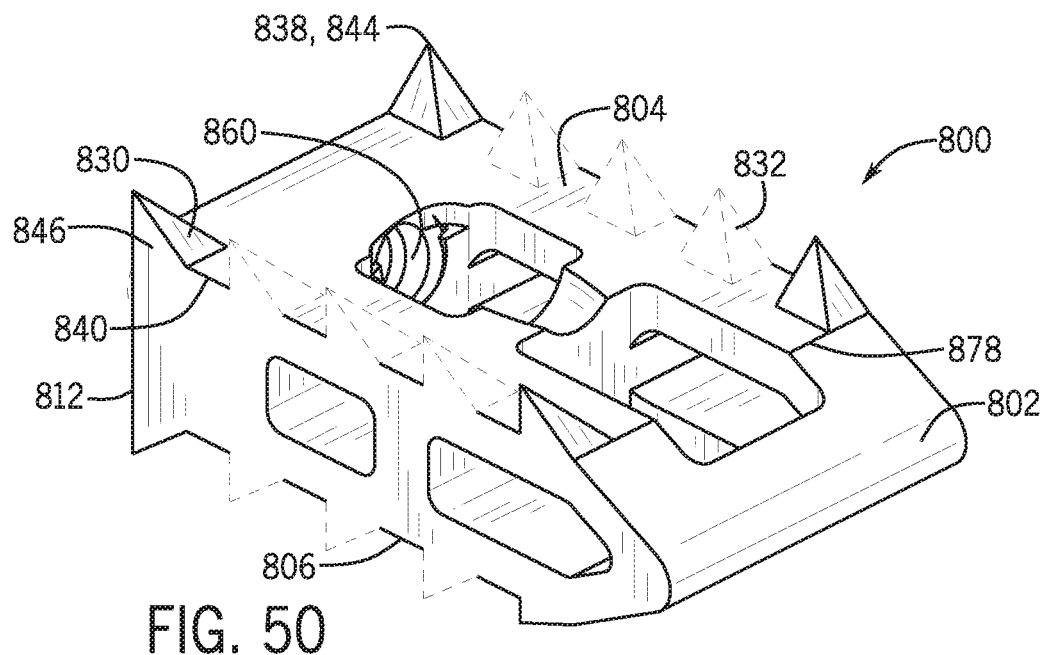
FIG. 50 is a front perspective view of an additional embodiment of a spinal implant device in accordance with an embodiment of the present disclosure.
Figure 51:
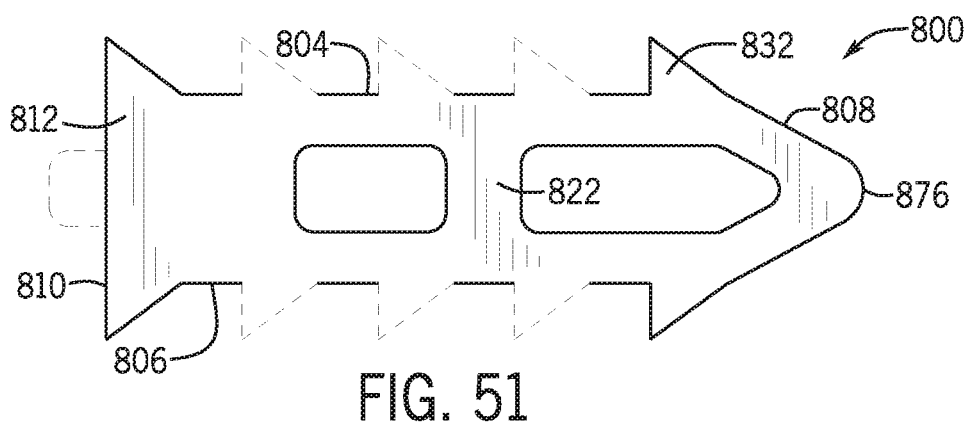
FIG. 51 is a left elevation view of the spinal implant device of FIG. 50 in accordance with an embodiment of the present disclosure.
Figure 52:
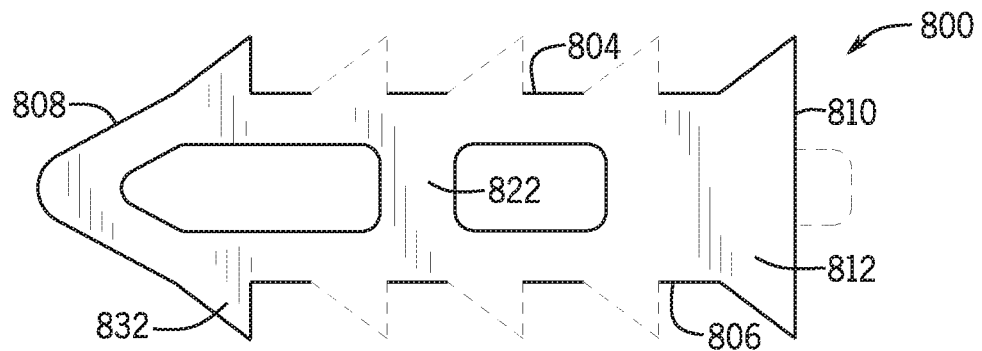
FIG. 52 is a right elevation view of the spinal implant device of FIG. 50 in accordance with an embodiment of the present disclosure.
Figure 53:
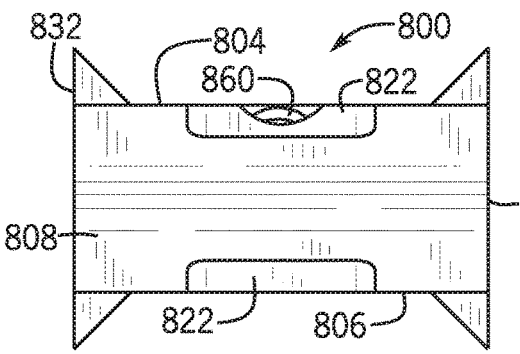
FIG. 53 is a front elevation view of the spinal implant device of FIG. 50 in accordance with an embodiment of the present disclosure.
Figure 54:
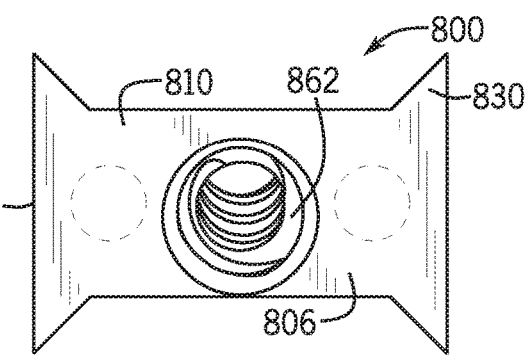
FIG. 54 is a rear elevation view of the spinal implant device of FIG. 50 in accordance with an embodiment of the present disclosure.
Figure 55:
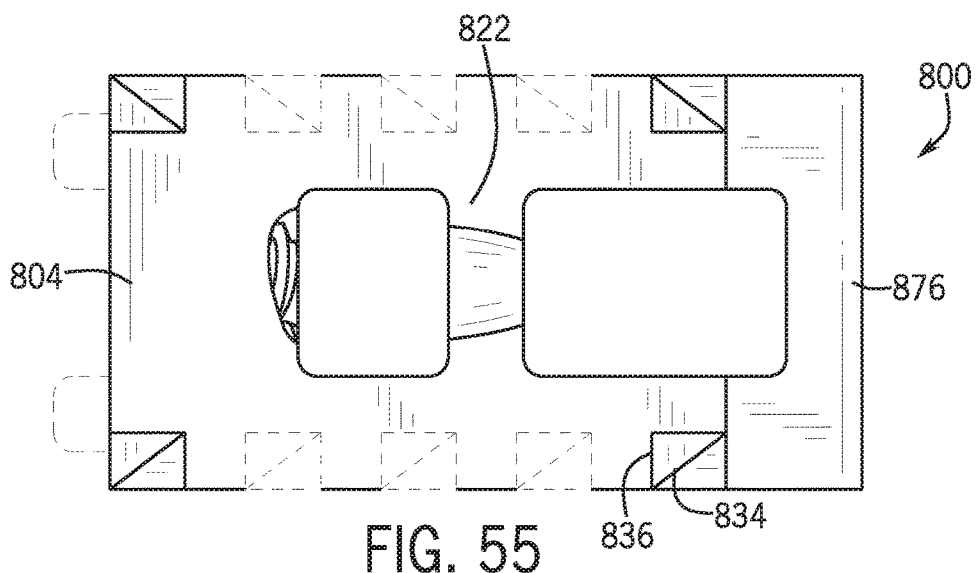
FIG. 55 is a top plan view of the spinal implant device of FIG. 50 in accordance with an embodiment of the present disclosure.

As illustrated in FIGS. 1-3, the main body 102 may be sized and shaped to facilitate insertion of the implant 100 within a spinal facet joint. For example, the front surface 108 may be shaped arcuately to define a protruding leading edge 176. In such embodiments, the leading edge 176 as well as the arcuate shape of the front surface 108 may facilitate insertion of the implant 100 within a facet joint. For instance, as the leading edge 176 is inserted within a spinal facet joint, the arcuate shape of the front surface 108 may increasingly separate adjacent vertebrae a sufficient distance to permit the implant 100 to be sufficiently inserted (e.g., fully) within the intervertebral joint space. As shown throughout, the arcuate shape of the front surface 108 may vary from substantially bullnose (see, e.g., FIG. 9) to very pointed (see, e.g., FIG. 51). Depending on the particular application, the arcuate shape of the front surface 108 may be symmetrical or asymmetrical about a vertical axis, a horizontal axis, or both of the main body 102. In some embodiments, the curvature of the front surface 108 may transition smoothly into the leading face 134 of the protrusions 132 positioned near the front surface 108 (see, e.g., FIG. 2). In other embodiments, however, the slope of the leading face 134 may be different than that of the front surface 108 such that a line of demarcation 178 is defined between the front surface 108 and the protrusions 132 positioned near the front surface 108 (see, e.g., FIG. 30).

FIGS. 8-56 illustrate additional embodiments of a spinal implant 200, 300, 400, 500, 600, 700, 800. With the exception of the description below, the spinal implants 200, 300, 400, 500, 600, 700, 800 of FIGS. 8-56 are similar to the implant 100 and its associated description above. Accordingly, in certain instances, descriptions of like features will not be discussed when they would be apparent to those with skill in the art in light of the description above and in view of FIGS. 1-60. For ease of reference, like structure is represented with appropriately incremented reference numbers.

Figure 57:
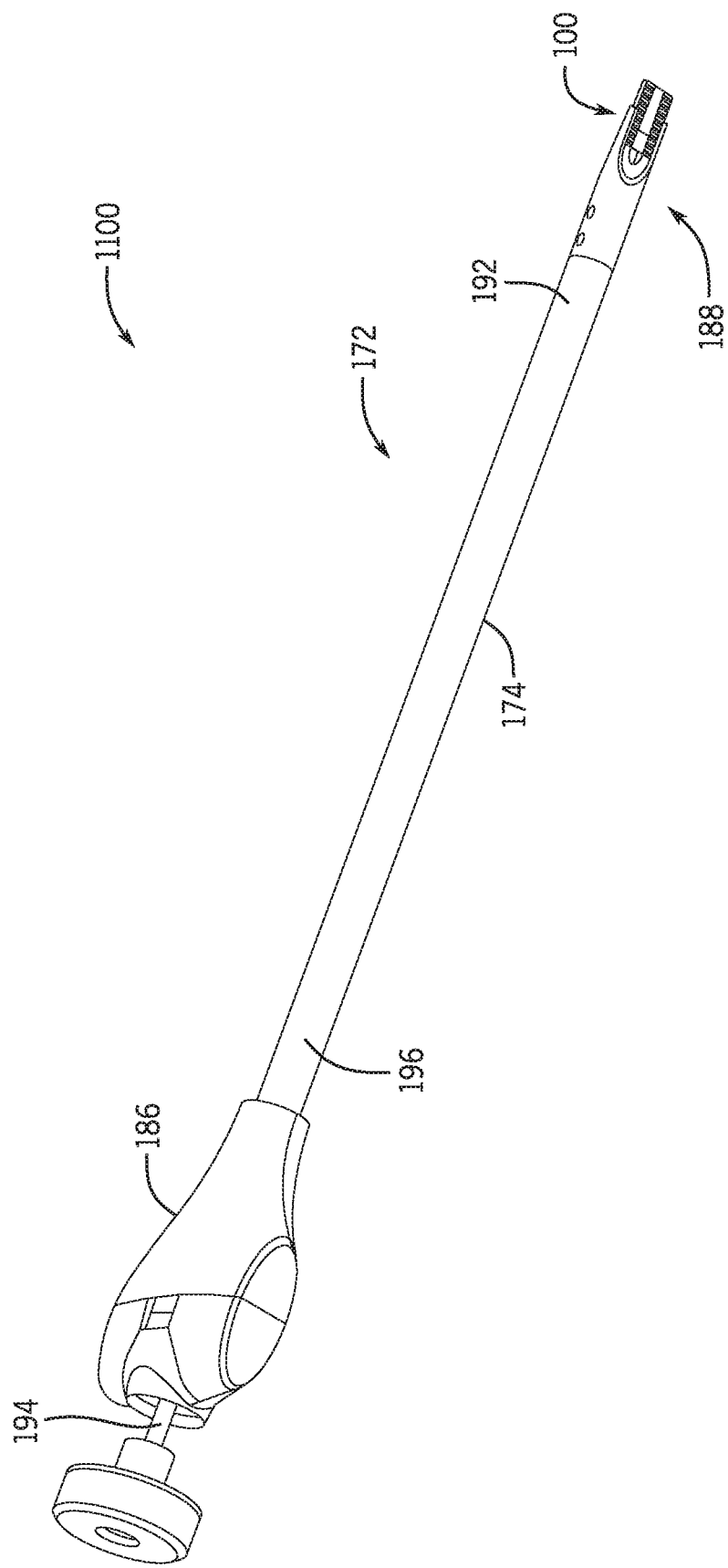
FIG. 57 is a perspective view of a distraction system in accordance with an embodiment of the present disclosure.
Figure 58:
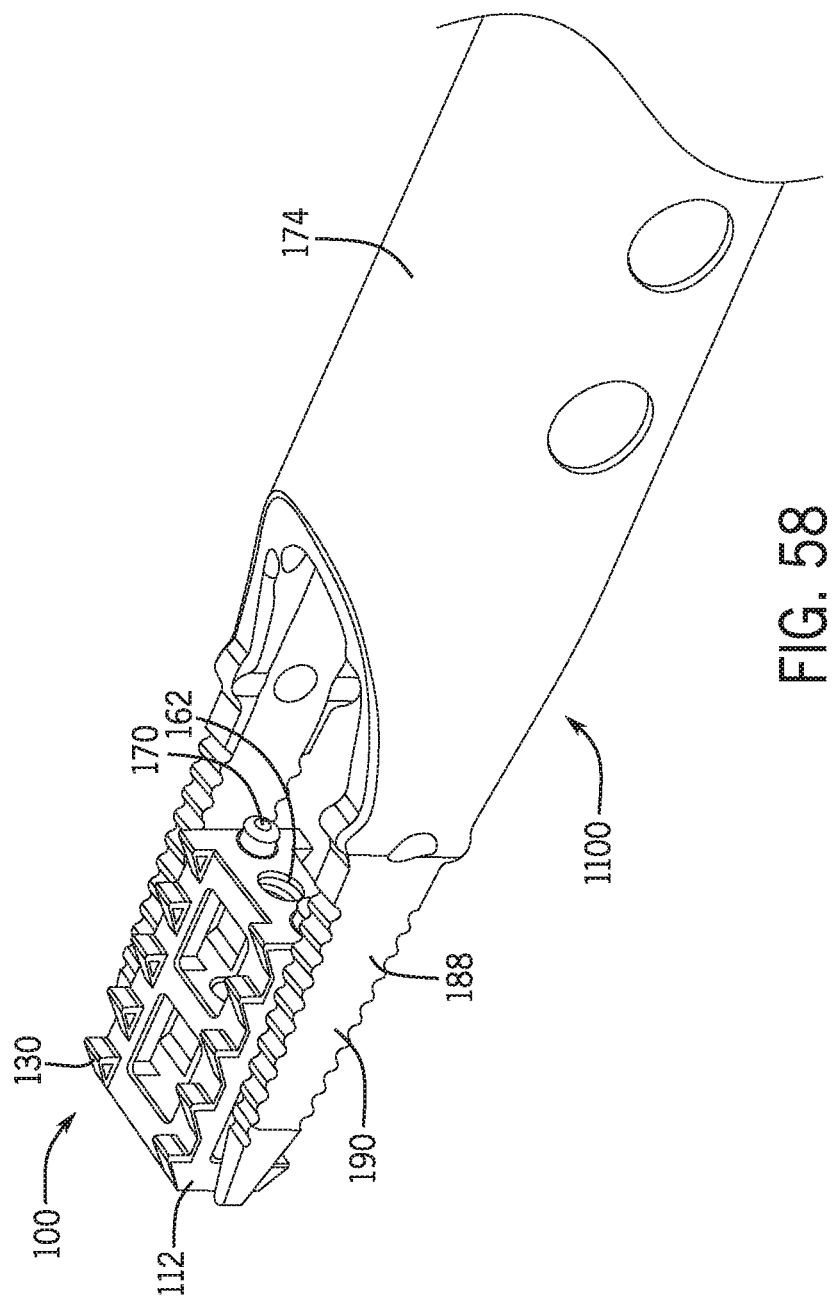
FIG. 58 is an enlarged fragmentary view of the distraction system of FIG. 57 in accordance with an embodiment of the present disclosure.
Figure 59:
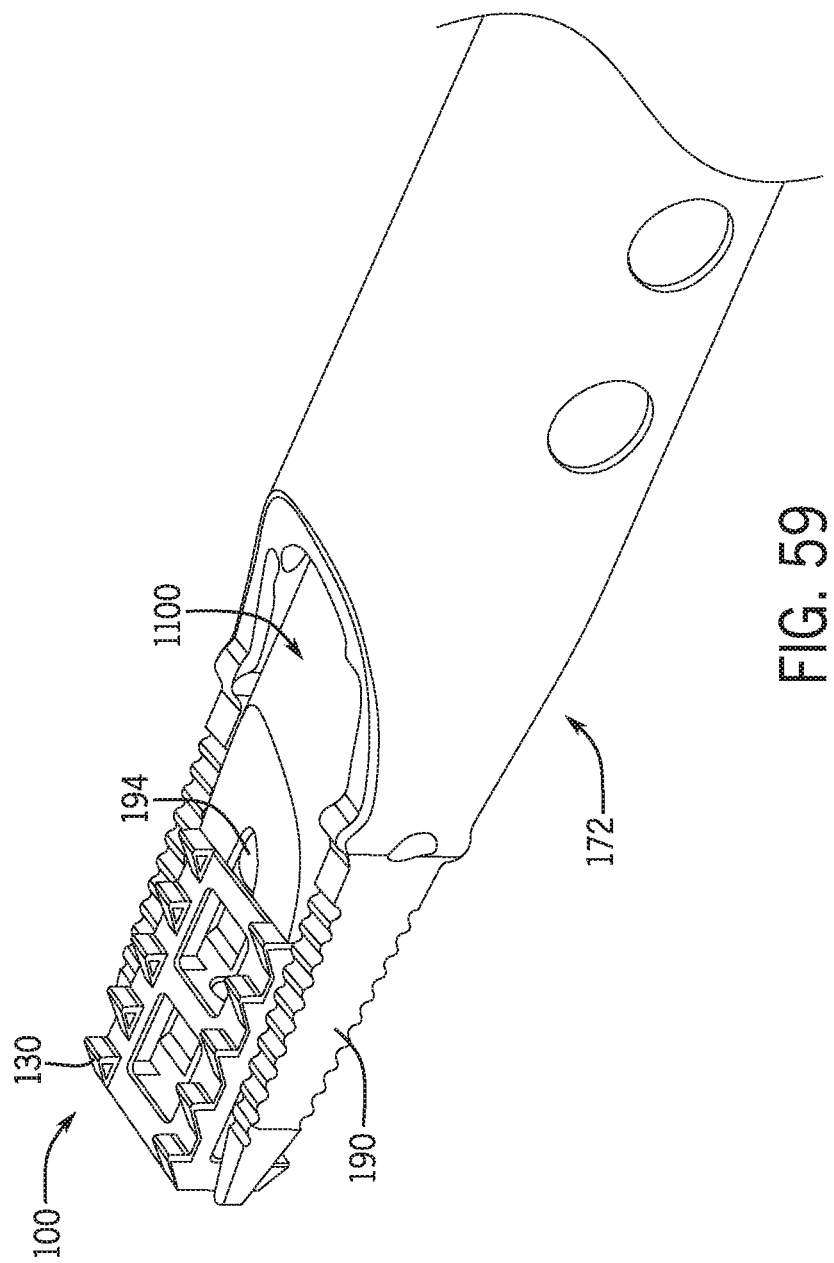
FIG. 59 is an additional enlarged fragmentary view of the distraction system of FIG. 57 showing a rod engaged with a spinal implant device in accordance with an embodiment of the present disclosure.

With reference to FIGS. 8-28 and 36-56, the protrusions 232, 332, 432, 632, 732, 832 in some embodiments include a pyramidal shape, including a plurality (e.g., four) generally triangular lateral faces 180 extending from the main body 202, 302, 402, 602, 702, 802 and terminating at the tip 238, 338, 438, 638, 738, 838, such as at a pointed tip. For example, the protrusions 232, 332, 432, 632, 732, 832 may form a right pyramid (see FIGS. 22-28), an oblique pyramid, a right-angled pyramid (see FIGS. 8-21 and 43-56), an acute pyramid, an obtuse pyramid, or any combination thereof. The lateral faces 180 of the pyramidal-shaped protrusions 232, 332, 432, 632, 732, 832 may be congruent (see, e.g., FIGS. 22-28) or may be sized differently (see, e.g., FIGS. 8-14) to position the tip 238, 338, 438, 638, 738, 838 in a desired position relative the main body 202, 302, 402, 602, 702, 802 of the implant 200, 300, 400, 600, 700, 800, such as near the opposing side surfaces 212, 312, 412, 612, 712, 812 (see FIG. 8) or towards a midline of the main body 202, 302, 402, 602, 702, 802 (see FIG. 15). Turning to FIGS. 57-59, a distraction system 1100 may be configured to deliver the implant 100 into a spinal facet joint space via, for example, a posterior approach. In one implementation, the distraction system 1100 includes a delivery device 172. As shown, the delivery device 172 includes a tubular body 174 and a handle 186 and a delivery mechanism 188 positioned at opposing ends of the tubular body 174. As shown, the delivery mechanism 188 may include a pair of resilient prongs 190 that releasably engage the opposing side surfaces 112 of the implant 100 to support the implant 100 at or near a distal end 192 of the delivery device 172. For example, the prongs 190 may be configured to provide a lateral compressive force on the opposing side surfaces 112 of the implant 100 to releasably hold the implant 100 in place relative the delivery device 172. In one embodiment, a rod 194 extends through the tubular body 174 (e.g., through a lumen defined in the tubular body 174) to, for instance, distally push the implant 100 from an interference fit engagement with the delivery mechanism 188 and into a patient's intervertebral joint space. For example, actuation of the rod 194 may cause the prongs 190 to resiliently deform to release the implant 100 in position. In some embodiments, the rod 194 may engage the rear surface 110 of the implant 100, such as the posts 170, to align the implant 100 during insertion and/or securement. As shown, the rod 194 may be actuated from a proximal end 196 of the delivery device 172, such as at or near the handle 186.

Figure 60:
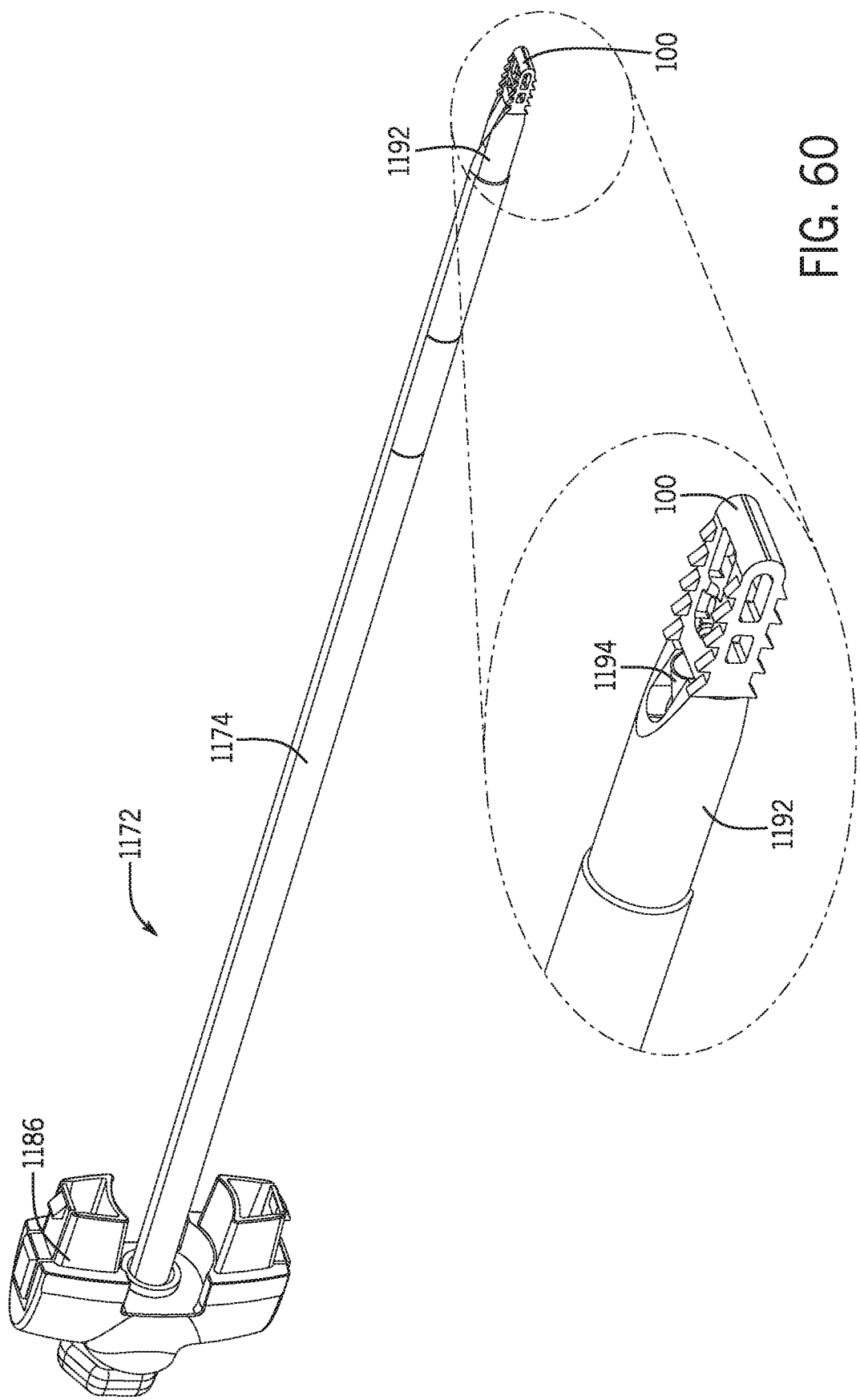
FIG. 60 is a perspective view of an additional distraction system in accordance with an embodiment of the present disclosure.

FIG. 60 illustrates an additional delivery device 1172. With the exception of the following description, the delivery device 1172 is configured similar to the delivery device 172 discussed above, and accordingly, like features will not be discussed when they would be apparent to those of skill in the art with reference to FIG. 60 and the discussion above. As shown in FIG. 60, the implant 100 may be coupled to (e.g., cantilevered from) the distal end 1192 of the delivery device 1172. For example, the rod 1194, which may be actuated from at or near the handle 1186, may releasably engage the implant 100 to couple the implant 100 and the delivery device 1172 together. In one embodiment, the rod 1194 may engage the rear surface 110 of the implant 100, such as threadedly engaging the securement aperture 162. To align the implant 100 and/or limit rotational movement of the implant 100 relative the delivery device 1172, the posts 170 may engage corresponding structure disposed within the distal end 1192 of the tubular body 1174, as discussed above.

To position the implant 100 within a patient's spinal facet joint, in one embodiment, a percutaneous or minimally invasive incision is made in the posterior region of the spinal region adjacent the target facet joint. The delivery device 172 or 1172 may then be advanced within the incision to position the implant 100 adjacent the target facet joint, at which point the implant 100 may be delivered into proper position within the patient's intervertebral joint space, such as via actuation of the rod 194 or 1194. Once the implant 100 is inserted, the retaining features 130 may frictionally secure the implant 100 within the facet joint, as discussed above. If desired, a bone screw, such as bone screw 164, may be inserted within the implant 100 to engage an adjacent vertebra and further secure the implant 100 within the target facet joint (see FIG. 61A-61C).

Turning now to FIGS. 62-75, these figures illustrate embodiments of a spinal implant operable to engage two adjacent vertebrae of a spinal facet joint to fuse the two adjacent vertebrae together (e.g., vertebrae of the human cervical spine, such as the C5 and C6 vertebrae). Referring to FIGS. 62-75, a spinal implant 900 according to one embodiment of the present disclosure includes a main body 902 defined by opposing top and bottom surfaces 904, 906, opposing distal or front and proximal or rear surfaces 908, 910, and opposing side surfaces 912. In some embodiments, the majority of the surfaces (e.g., the opposing top and bottom surfaces 904, 906, the rear surface 910, and the opposing side surfaces 912) may be planar. As such, the implant 900 may be generally cuboid in shape, though other shapes are contemplated that permit the implant 900 to be inserted within a spinal facet joint and maintain a certain distance between two adjacent vertebrae. As described in more detail below, the spinal implant 900, which may be formed of a bone or bone substitute material or a biocompatible metal, ceramic, polymer, or some combination thereof, may be sized and shaped to fit snugly (e.g., through friction fit) into or otherwise engage or abut adjacent vertebrae of the spinal facet joint.

To reduce weight and offer cross-sectional areas for new bone growth and fusion, for instance, the implant 900 may include one or more openings or windows 920 defined in at least one surface of the main body 902. For example without limitation, the implant 900 of FIGS. 62-75 includes two windows 920 defined in each of the top, bottom, and opposing side surfaces 912 of the main body 902, though any number of windows 920 is contemplated. In such embodiments, the implant 900 may include an interior wall 922 positioned within the main body 902 to define a portion of at least two windows 920. In embodiments having two windows 920 defined in each of the top, bottom, and opposing side surfaces 904, 906, 912 of the main body 902, the interior wall 922 may define a portion of each window 920. The windows 920 may be any size, shape, and orientation. For instance, in the embodiments of FIGS. 62-75, each of the windows 920 of a respective surface of the main body 902 is generally rectangular and arranged end to end along a midline of the respective surface. The windows 920 closer to the distal or front surface 908 of the implant may include an arcuate edge portion 920a similar in shape to the arcuate edge portion 908 of the distal or front surface 908. As shown, each of the windows 920 is adapted to place a hollow interior of the implant 900 in communication with the surrounding environment. In such embodiments, the hollow interior of the implant 900 may include one or more chambers, such as a distal chamber 924 separated from a proximal chamber 926 by the interior wall 922. To fuse adjacent vertebrae together, the chambers 924, 926 may by packed (via the windows 920, for instance) with a bone or bone substitute material to cause bone ingrowth into the hollow interior of the implant 900. As shown, one of the chambers 924, 926 may be larger in length or size than the other, such as the distal chamber 924 being larger than the proximal chamber 926.

With continued reference to FIGS. 62-75, the implant 900 may include at least one retaining feature 930 associated with at least one surface of the main body 902 to frictionally engage the implant 900 within a spinal facet joint. For instance, the implant 900 may include a plurality of protrusions 932 extending away from at least one of the opposing top and bottom surfaces 904, 906 of the main body 902 (e.g., from both the top and bottom surfaces 904, 906). As described herein, the protrusions 932, which may be referred to as teeth, may be operable to permit the implant 900 to be inserted into a spinal facet joint but may also limit or hinder its removal therefrom. For example, the protrusions 932 may be directionally sized and shaped such that a force required to remove the implant 900 from the spinal facet joint is substantially greater than a force required to insert the implant 900 within the facet joint. In this manner, the implant 900 may be inserted into proper position within the facet joint as desired. Once inserted, the protrusions 932 may limit movement of the implant 900 within the facet joint in at least the removal direction. In some embodiments, the protrusions 932 may be operable to limit lateral movement of the implant 900 within the facet joint, as explained below.

As shown in FIGS. 62-64 and 69-71, each of the protrusions 932 may include a leading face 934, a trailing face 936, and a tip 938 formed at an intersection between the leading and trailing faces 934, 936. In some embodiments, the protrusions 932 may extend from a location 940, which may be a centered or off-centered location, defined between the lateral edge 941 defined by opposing top and bottom surfaces 904, 906 and the opposing side surfaces 912 and the lateral edge 942 of a window 920 in the top or bottom surface of the implant. That is, the protrusions 932 are "set-in" relative to the lateral edge 912. In such embodiments, each of the top and bottom surfaces 904, 906 may include at least one row of protrusions 932 extending between the distal or front and proximal or rear surfaces 908, 910 and at a centered or off-centered location 940 of the respective surface, the windows 920 being positioned between the rows of protrusions 932. As shown in FIGS. 63, 64, 70 and 71, each row of protrusions 932 may include a sawtooth profile, though other profile shapes are contemplated including triangle, square, and sinusoidal, among others.

The protrusions 932 may be variously sized and shaped depending on the particular application. For example without limitation, the trailing face 936 may include a slope that is different than a slope of the leading face 934. In one embodiment, the trailing face 936 may include a slope that is greater than a slope of the leading face 934. For instance, the slope of the trailing face 936 may be approximately 90° such that the trailing face 936 extends substantially perpendicular from the top and bottom surfaces 904, 906 of the main body 902. In some embodiments, the slope may be between 25 and 40 degrees. In some embodiments, the slope may be 28 degrees. In some embodiments, the tip may be 37 degrees. In the embodiments of FIGS. 62-75, the tip 938 is a ridge 942 extending a width of the protrusion, such as the entire width of the associated protrusion. Though FIGS. 62-75 show a ridge 942, as explained below, the tip 938 may take on other shapes and configurations, such as a point, a truncated flat surface, or the like, depending on a desired aesthetic and/or functional characteristic. In each of the embodiments described herein, however, the shape and configuration of the protrusions 932 permit the implant 900 to be inserted within a facet joint while also resisting pullout. For example, the protrusions 932 may be configured such that the protrusions 932 engage into surrounding bone or tissue when the implant 900 is moved away from the facet joint, such as in the removal direction. In some embodiments, the protrusions 932 may be shaped such that the protrusions 932 also engage into surrounding bone or tissue when the implant 900 is moved laterally within the facet joint. In such embodiments, the protrusions 932 may include a lateral face 946 extending from a location 940, which may be a centered or off-centered location, defined between the lateral edge 941 defined by the opposing top and bottom surfaces 904, 906 and the opposing side surfaces 912 and the lateral edge 942 of a window 920 in the top or bottom 904, 906 surface of the implant. That is, the lateral face 946 of the implant is not adjacent to or coplanar with the lateral edge 941 of the implant 900. As shown in FIGS. 62, 66, 69 and 73, the lateral face 946 in one embodiment may not be coplanar with one of the opposing side surfaces 912. That is, the lateral face 946 may be spaced away from the opposing side surfaces 912, such as inwardly from the edge 941 towards the interior of the main body 102, depending on the particular application. Alternatively, the lateral face 946 may be coplanar with one of the opposing side surfaces 912.

In addition to the description above, the protrusions 932 may be variously sized and shaped in other ways. For instance, the height of the protrusions 932 (as defined by the tips 938) may be uniform or may vary along the length of the implant 900 between the distal or front and proximal or rear surfaces 908, 910 of the main body 902. For instance, the protrusions 932 positioned nearer the distal or front surface 908 of the main body 902 may have a smaller height than the protrusions 932 positioned away from the distal or front surface 108 (see FIG. 63), or vice-versa. Similarly, the distance between the protrusions 932 may be uniform or may vary along the length of the implant 900. For instance, the distance between the protrusions 932 positioned nearer the distal or front surface 908 may be less than the distance between the protrusions 932 positioned nearer the proximal or rear surface 910, or vice-versa.

Figure 62:
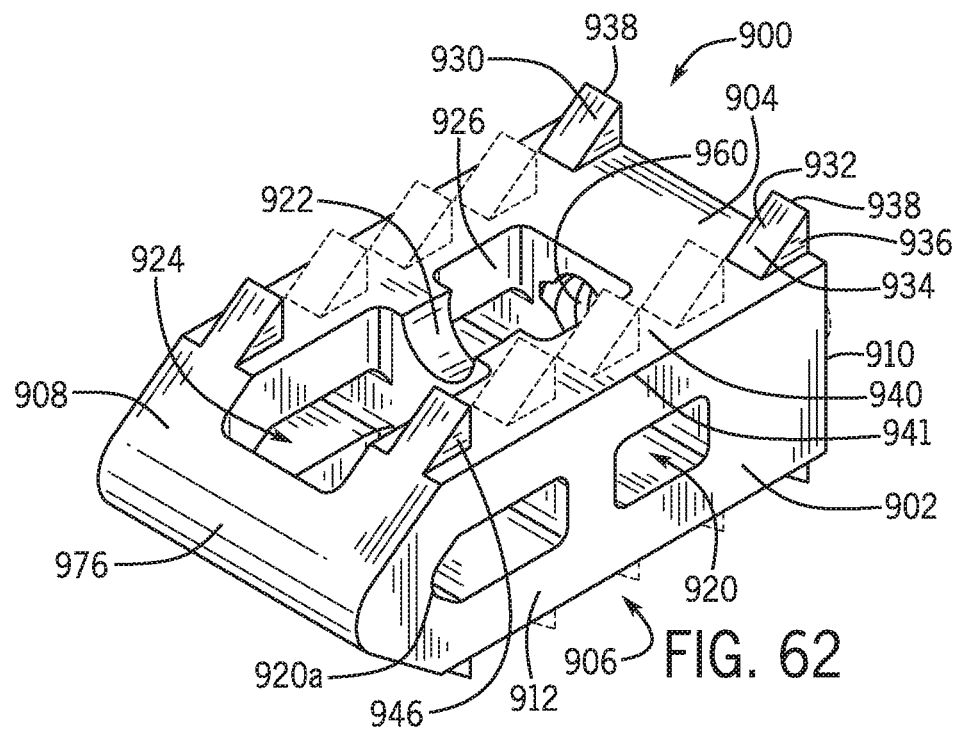
FIG. 62 is a front perspective view of a spinal implant device in accordance with an embodiment of the present disclosure.

Referring now to FIGS. 62-75, the implant 900 may include at least one securement feature or fastener 160 associated with at least one surface of the main body 902 to fixedly secure the implant 900 within the spinal facet joint. For instance, a securement aperture 962 may be defined in the main body 902 (e.g., in at least the proximal or rear surface 910 of the main body 902), the securement aperture 962 operable to receive a fastener therein, such as a bone screw 164 (see FIGS. 61A-61C). As shown, the securement aperture 962 may be angled such that the bone screw 164 extends through the proximal or rear surface 910 and one of the top and bottom surfaces 904, 906 (e.g., through the top surface 904) of the main body 902 to engage an adjacent vertebra. To secure the implant 900 within the facet joint, the securement aperture 962 may be angled so the bone screw 164 inserted therein extends upwardly to engage an upper vertebrae, though the opposite may be true depending on the particular application. In this manner, the implant 900 may be inserted within a patient's facet joint irrespective of the relative positions of the top and bottom surfaces 904, 906. In the embodiments described herein, the securement aperture 962 may be configured such that the bone screw 164 extends through the proximal chamber 926 and through at least one window 920 defined in the top surface 904 or the bottom surface 906 of the main body 902. As best seen in FIG. 62, depending on the size of the windows 920 as well as the angle of the securement aperture 962, the interior wall 922 may include a notch 966 to at least accommodate the bone screw 164 to be inserted within the implant 900. The bone screw 164 described herein may be made of any suitable material, including biocompatible metals, ceramics, and/or polymers. In some embodiments, the bone screw 164 may be a DTRAX® Bone Screw-A from Providence Medical Technology, Inc.

Figure 66:
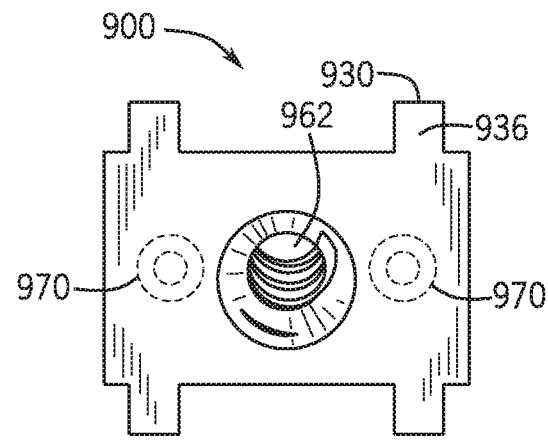
FIG. 66 is a rear elevation view of the spinal implant device of FIG. 62 in accordance with an embodiment of the present disclosure.
Figure 67:
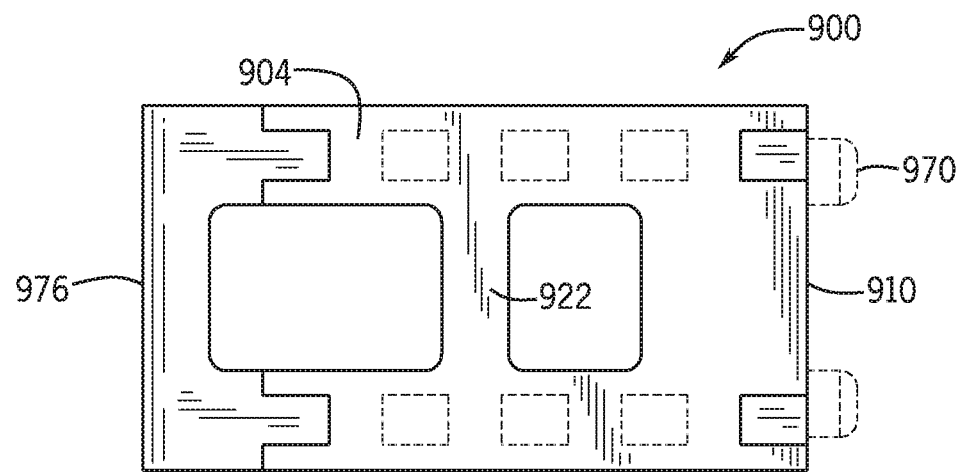
FIG. 67 is a top plan view of the spinal implant device of FIG. 62 in accordance with an embodiment of the present disclosure.
Figure 68:
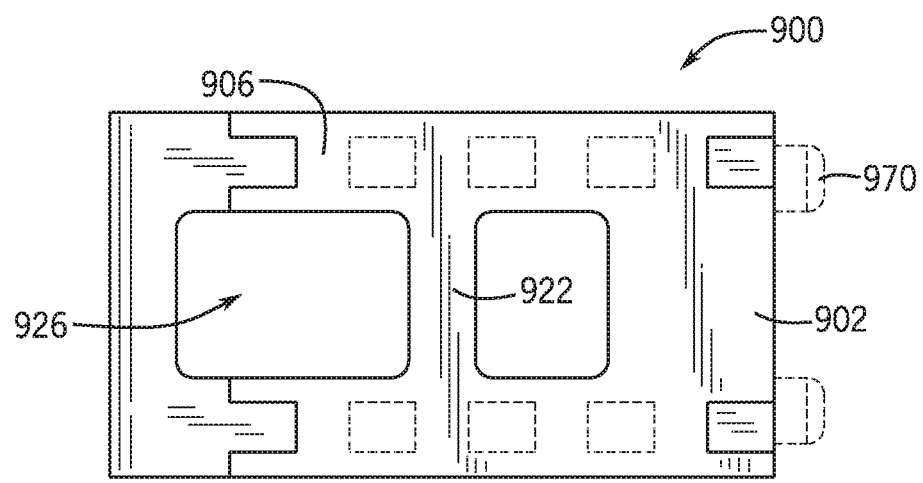
FIG. 68 is a bottom plan view of the spinal implant device of FIG. 62 in accordance with an embodiment of the present disclosure.
Figure 69:
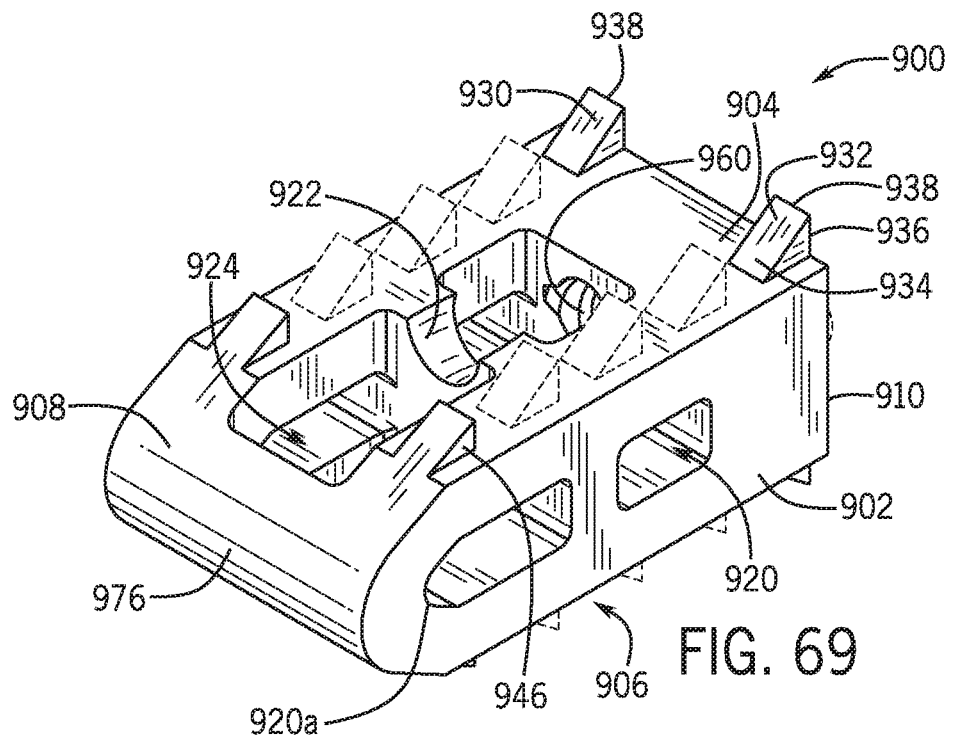
FIG. 69 is a front perspective view of an additional embodiment of a spinal implant device in accordance with an embodiment of the present disclosure.
Figure 70:
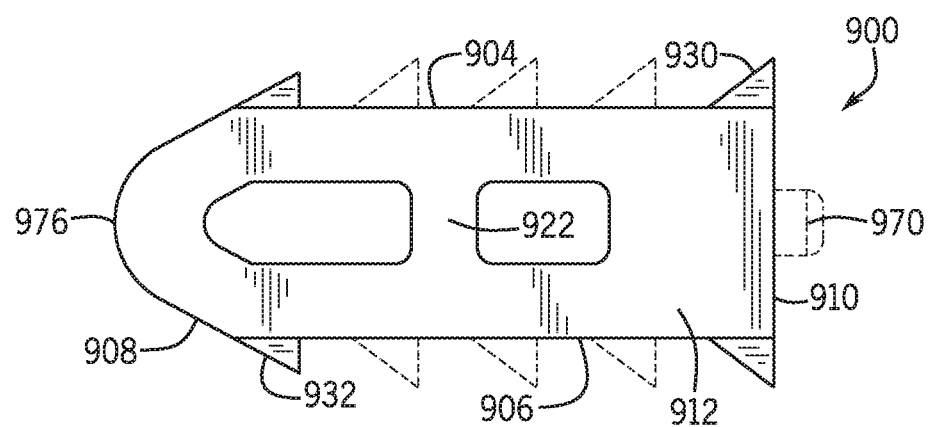
FIG. 70 is a left elevation view of the spinal implant device of FIG. 69 in accordance with an embodiment of the present disclosure.
Figure 71:
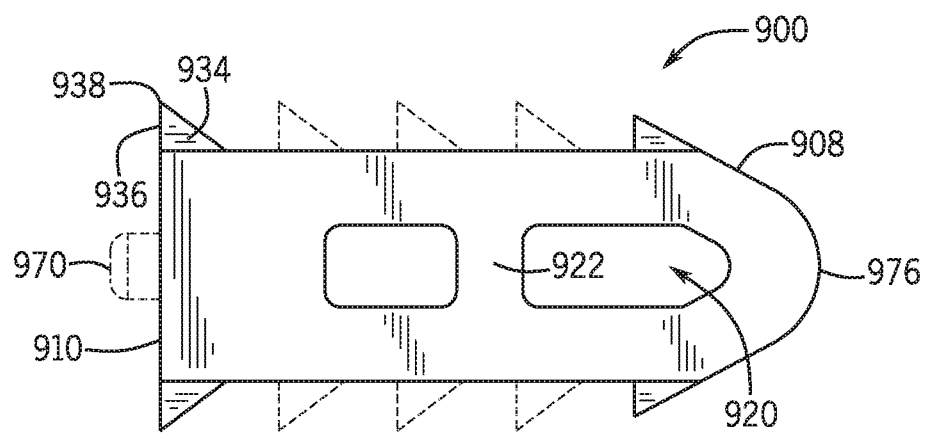
FIG. 71 is a right elevation view of the spinal implant device of FIG. 69 in accordance with an embodiment of the present disclosure.
Figure 72:
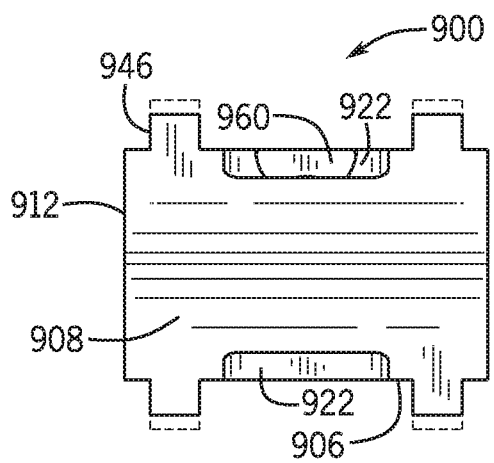
FIG. 72 is a front elevation view of the spinal implant device of FIG. 69 in accordance with an embodiment of the present disclosure.
Figure 73:
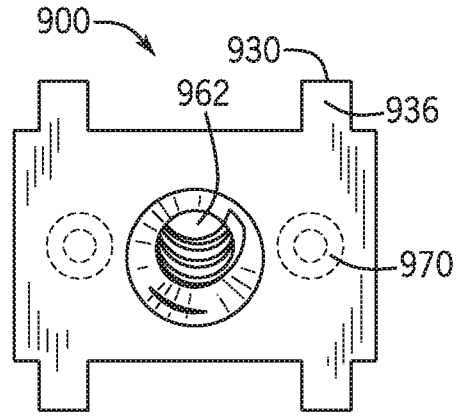
FIG. 73 is a rear elevation view of the spinal implant device of FIG. 69 in accordance with an embodiment of the present disclosure.
Figure 74:
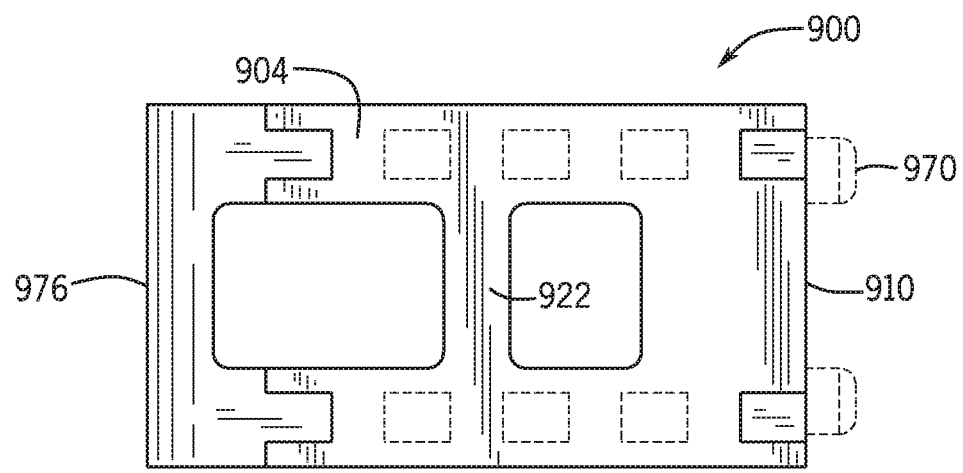
FIG. 74 is a top plan view of the spinal implant device of FIG. 69 in accordance with an embodiment of the present disclosure.
Figure 75:
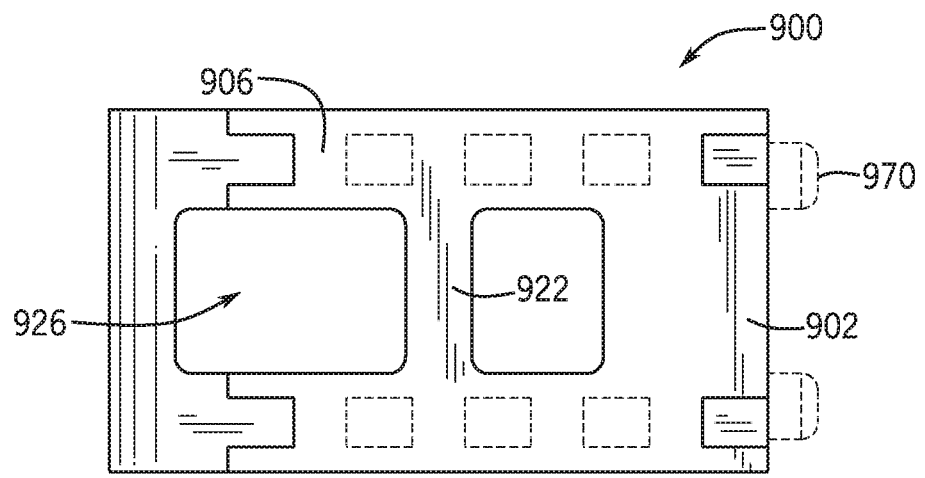
FIG. 75 is a bottom plan view of the spinal implant device of FIG. 69 in accordance with an embodiment of the present disclosure.

Turning to FIGS. 63, 66-68, 70 and 73-75, the implant 900 may include other features. For example, the implant 900 in one embodiment may include one or more posts 970 (e.g., two posts 970) extending from the proximal or rear surface 910 of the implant 900. In such embodiments, the posts 970 may be operable to properly position the implant 900 within a facet joint, such as through engagement with other portions or members of a distraction system. For example, the posts 970 may be operable to engage a delivery device, such as the delivery devices shown in FIGS. 57-60) such that the delivery device can position the implant 900 within a patient's facet joint. For example, the posts 970 may be received within corresponding apertures defined in the delivery device to align and/or couple the implant 900 to the delivery device, as more fully explained below. As shown in FIGS. 66 and 73, the posts 970 extend from the proximal or rear surface 910 of the implant 900 in a laterally spaced relationship. In such embodiments, the securement aperture 962 may be defined within the proximal or rear surface 910 between the two posts 970.

Figure 63:
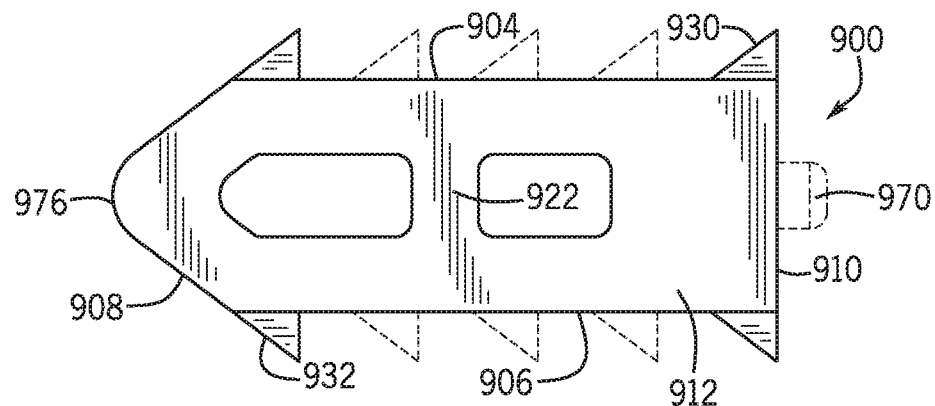
FIG. 63 is a left elevation view of the spinal implant device of FIG. 62 in accordance with an embodiment of the present disclosure.
Figure 64:
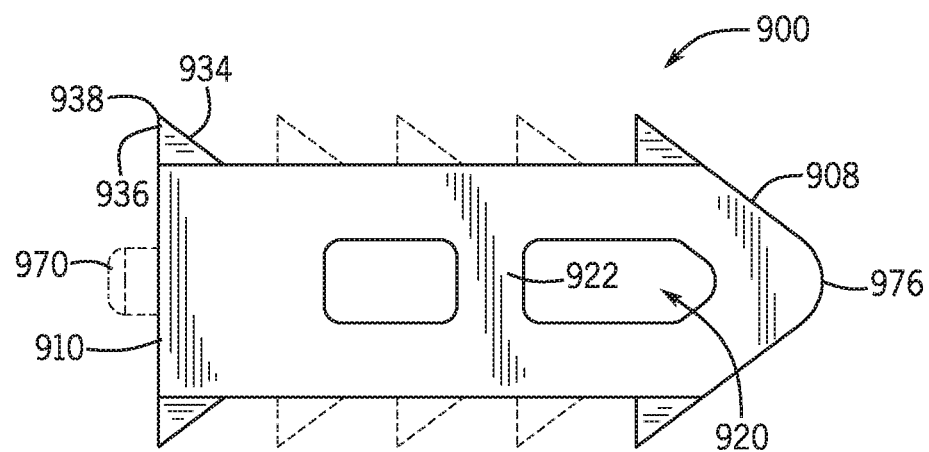
FIG. 64 is a right elevation view of the spinal implant device of FIG. 62 in accordance with an embodiment of the present disclosure.
Figure 65:
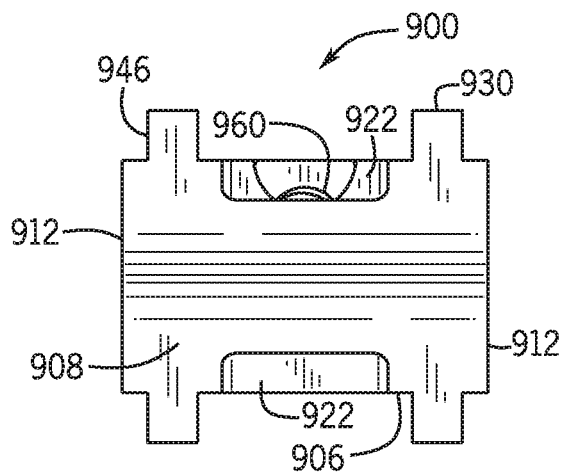
FIG. 65 is a front elevation view of the spinal implant device of FIG. 62 in accordance with an embodiment of the present disclosure.

As illustrated in FIGS. 62-64, the main body 902 may be sized and shaped to facilitate insertion of the implant 900 within a spinal facet joint. For example, the distal or front surface 908 may be shaped arcuately to define a protruding leading edge 976. In such embodiments, the leading edge 976 as well as the arcuate shape of the distal or front surface 908 may facilitate insertion of the implant 900 within a facet joint. For instance, as the leading edge 976 is inserted within a spinal facet joint, the arcuate shape of the distal or front surface 908 may increasingly separate adjacent vertebrae a sufficient distance to permit the implant 900 to be sufficiently inserted (e.g., fully) within the intervertebral joint space. As shown throughout, the arcuate shape of the distal or front surface 908 may be substantially bullnose. The arcuate shape of the distal or front surface 908 may be symmetrical about a vertical axis, a horizontal axis, or both of the main body 902. In some embodiments, the curvature of the distal or front surface 908 may transition smoothly into the leading face 934 of the protrusions 932 positioned near the distal or front surface 908 (i.e. the slope of the leading face is the same as the slope of the distal or front surface). In other embodiments, however, the slope of the leading face 934 may be different than that of the distal or front surface.

Figure 76:
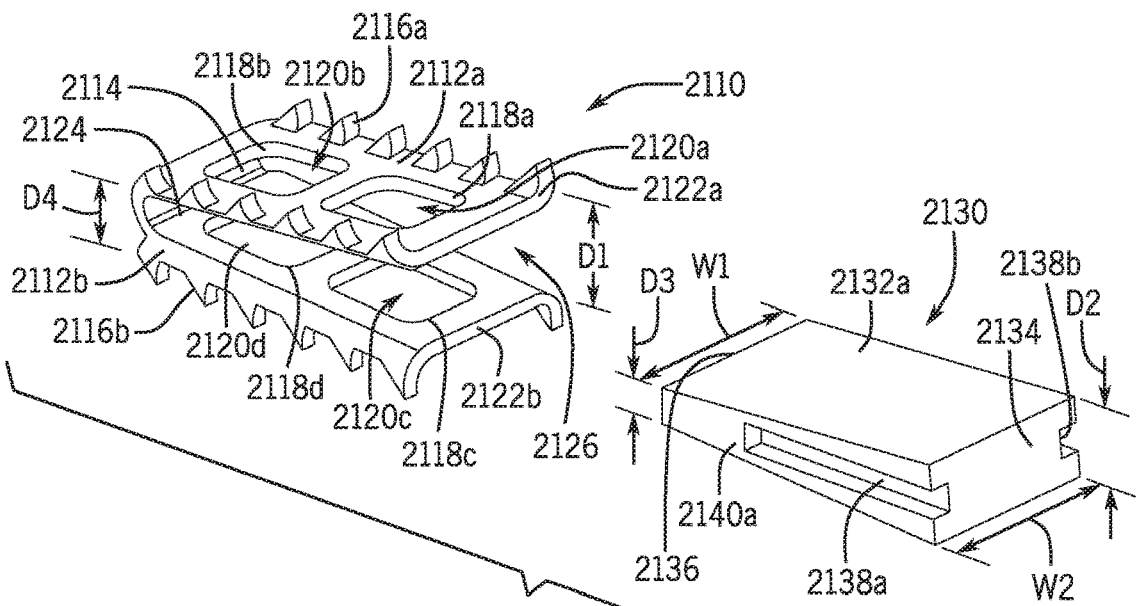
FIG. 76 is an exploded view of a spinal implant according to aspects of the present disclosure.

Turning now to FIGS. 76-80, in some aspects, the spinal implant 2100 includes an implant shell 2110 and a graft core 2130. The implant shell 2110 includes a first or top member 2112a and a second or bottom member 2112b. The top and bottom members 2112a, 2112b may be coupled by a connecting member 2114. In some examples, the connecting member 2114 may be integral with the top member 2112a and bottom member 2112b. In other examples, the connecting member 2114 may be attached or coupled to the top and bottom members 2112a, 2112b, respectively, to form the implant shell 2110. In some examples, the connecting member 2114 may be a resilient or flexible member 2114. In other examples, the connecting member 2114 may be rigid or semi-rigid. The connecting member 2114 may be straight, angular, and/or curved. In one example, the connecting member 2114 is curved such that the top member 2112a and bottom member 2112b are angularly offset from one another and the distal end of the implant (i.e. at the connecting member 2114) is blunt to prevent damage to the bone or surrounding tissue during insertion. That is, the top member 2112a and bottom member 2112b may be coupled to form a shell 2110 with an wedge or tapered shape as viewed from the side (see FIG. 79, wherein the top and bottom members 2112a, 2112b are not parallel). For example, as shown in FIG. 76, the distance D1 between the top and bottom members at the opening 2126 of the shell 2110 may be larger than the distance D4 between the top and bottom members of the shell 2110 at the connecting member 2114.

Figure 77:
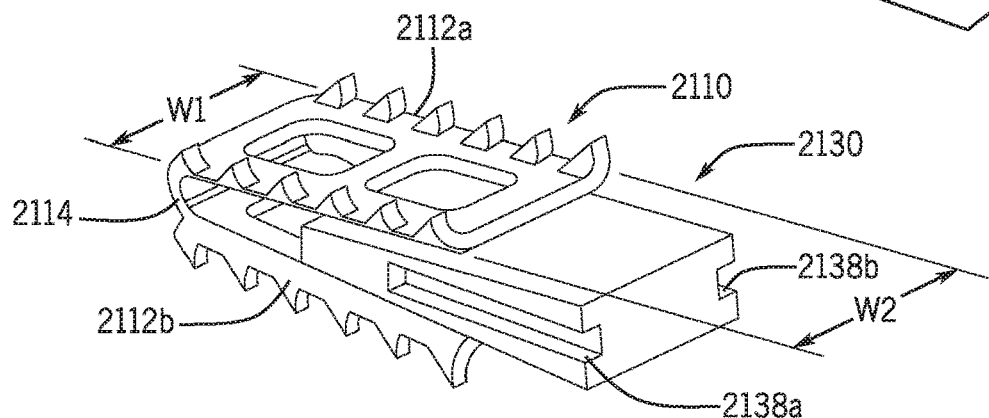
FIG. 77 is a perspective view of the spinal implant of FIG. 76 during assembly.
Figure 80:
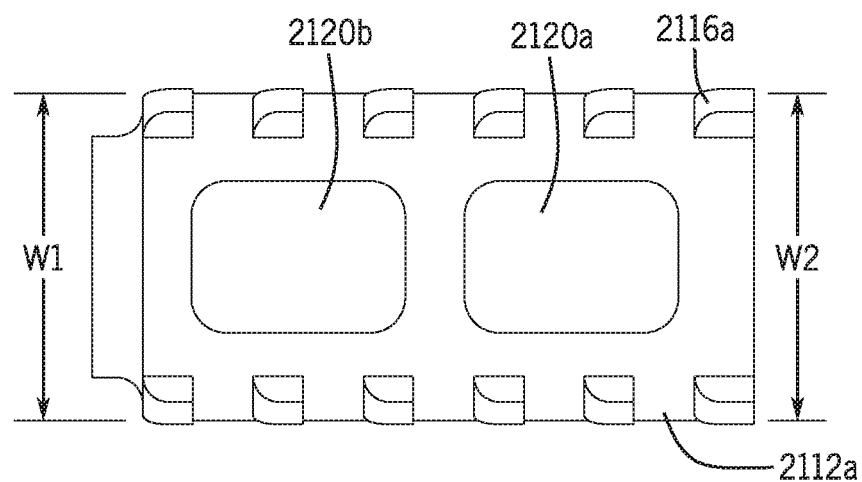
FIG. 80 is a top view of a shell of the spinal implant of FIG. 76.

In some examples, the top and bottom members 2112a, 2112b of the shell 2110 may also be tapered or wedge-shaped. As shown in FIGS. 77 and 80, the top member and bottom member 2112a, 2112b of the shell 2110 may have a width W2 at the side proximate the opening 2126 and a width W1 at a side proximate the connecting member 2114. The width W2 may be greater than W1 to provide an overall tapered or wedge shape to the top and bottom members 2112a, 2112b. That is, the top member 2112a and bottom member 2112b may be shaped with a perimeter which forms an overall trapezoidal shape when viewed from above or below.

As depicted in FIG. 76, the top member 2112a and bottom member 2112b of the shell 2110 include openings or apertures 2118a, 2118b and 2118c, 2118d defined therein. In some examples, the apertures 2118a-d may have a rectangular or square perimeter, and the corners of the apertures 2118a-d may be rounded or sharp. In other examples the apertures 2118a-d have an overall trapezoidal or wedge-shaped perimeter which substantially matches the perimeter of the top member 2112a and bottom member 2112b, respectively. However, the apertures 2118a-d may be substantially any shape, or combination of different shapes. In some examples, the apertures 2118a, 2118b, 2118c, and 2118d form bone growth channels 2120a, 2120b, 2120c, 2120d such that the graft core 2130 can promote osteoconduction once implanted.

Figure 78:
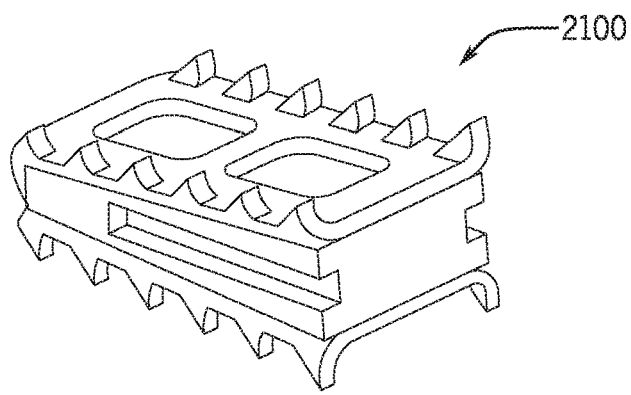
FIG. 78 is a perspective view of the spinal implant of FIG. 76 after assembly.
Figure 79:
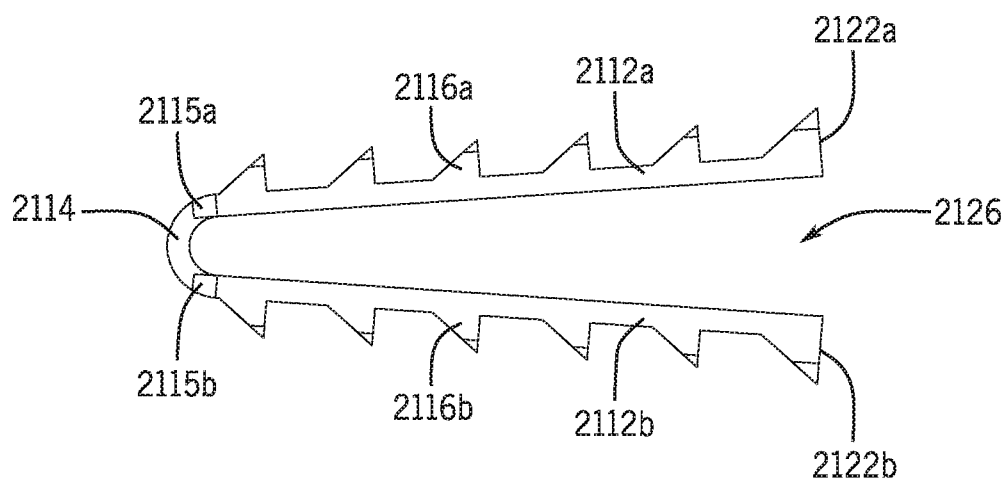
FIG. 79 is a side cross-sectional view of a shell of the spinal implant of FIG. 76.

The top and bottom members 2112a, 2112b may be provided with a plurality of engagement or attachment or fixation members such as serration features or teeth 2116a, 2116b. In some examples, the teeth 2116a, 2116b may be integrally formed on the lateral edges of the top and bottom members 2112a, 2112b, respectively. In other examples, the teeth 2116a, 2116b may be affixed to the top and bottom members 2112a, 2112b by welding, adhesive, or the like. As depicted in FIGS. 76-78, the teeth 2116a, 2116b may be angled or curved in opposite directions on opposing lateral sides of the top and bottom members 2112a, 2112b. The teeth fix the shell 2110 and implant within the facet joint and help to resist movement once implanted. In other examples, the teeth 2116a, 2116b may be curved or angled in substantially the same or similar directions. Furthermore, although the implant shell 2110 is shown with distinct teeth 2116a, 2116b, fixation members may in some examples be formed by a unitary member connecting the plurality of teeth 2116a, 2116b. As shown in FIGS. 76-80, in some examples the opposing lateral edges of the top and bottom members 2112*a*, 2112*b* may also have curved portions that extend to form a portion of the plurality of teeth 2116*a*, 2116*b*.

The shell 2110 is made of any biocompatible material, such as titanium alloys or plastic. The material may be flexible, rigid or semi-rigid. Furthermore, the shell 2110 has a selective radiopacity to allow the shell 2110 to be visualized with X-ray or other types of imaging. This enables a surgeon or other user to ensure proper location and fixation of the implant 2100 after placement.

The spinal implant further includes an allograft or graft core 2130. As depicted in FIGS. 76-78 and FIGS. 81-83, the graft core 2130 may be sized and shaped for receipt in the shell 2110. The graft core 2130 may be formed by machining or other appropriate method. In some examples, the graft core 2130 may be provided with channels 2138*a*, 2138*b* at least partially defined in opposite lateral faces of the graft core 2130, as shown in FIGS. 76-78 and FIG. 83, and others. The channels 2138*a*, 2138*b* include a tapered portion 2140*a*, 2140*b* provided at distal ends of the channels 2138*a*, 2138*b*. The channels 2138*a*, 2138*b* may be sized and shaped to couple with a graft core 2130 installation tool and may be centered along the depth at the proximal end D2 of the graft core 2130. The installation tool may be similar to the DTRAX Allograft Delivery Instrument or a similar tool having an elongated body with a lumen defined therein. Exemplary installation tools are described in more detail below.

Figure 81:
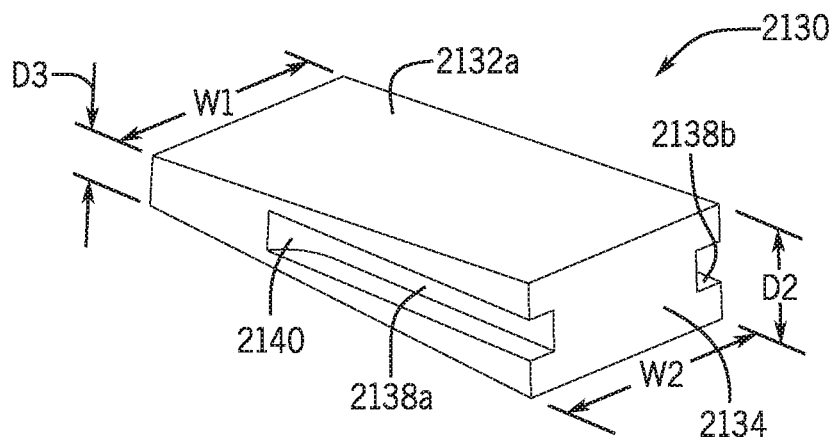
FIG. 81 is a perspective view of a graft core of the spinal implant of FIG. 76.
Figure 82:
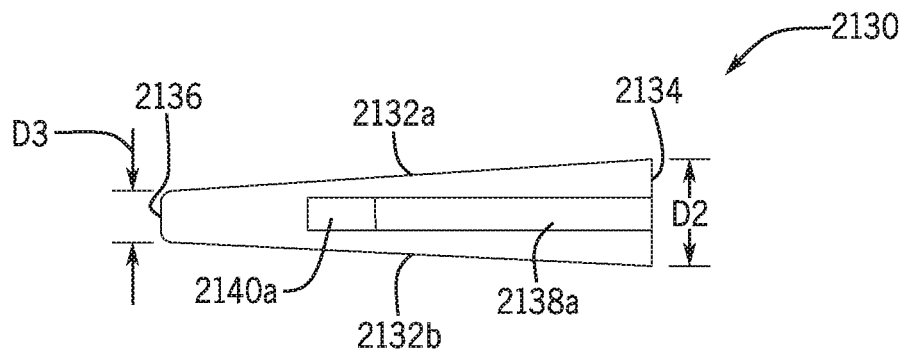
FIG. 82 is a side view of a graft core of the spinal implant of FIG. 76.
Figure 83:
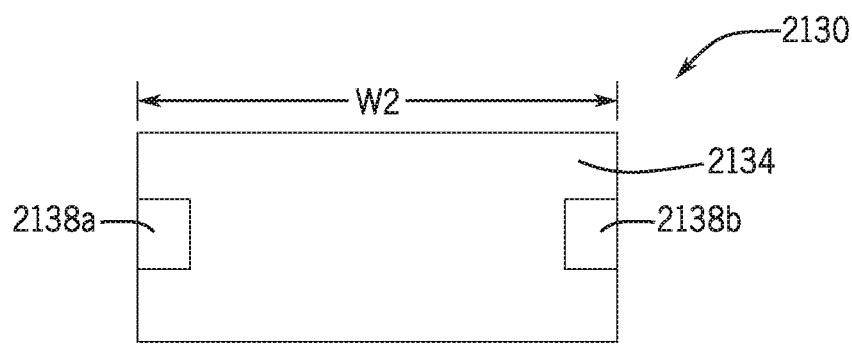
FIG. 83 is a rear view of a graft core of the spinal implant of FIG. 76.

With reference to FIGS. 81-83, the graft core 2130 may have an overall trapezoidal or wedge shape as viewed from above and the side. That is, the width at the proximal end, W2 may be greater than the width at the distal end, W1, such that the top and bottom faces of the graft core 130 have a trapezoidal or wedge-shaped perimeter, as shown in FIG. 81. Furthermore, the depth at the proximal end, D2 may be greater than the depth at the distal end, D3, such that lateral faces of the graft core 2130 may have a trapezoidal or wedge-shaped perimeter, as shown in FIG. 82.

Referring back to FIGS. 76-78, as discussed above the graft core 2130 is received in the shell 2110. Accordingly, in some examples the graft core 2130 may be wedge-shaped or tapered similar to the top and bottom members 2112*a*, 2112*b* of the shell 2110, as discussed above. That is, the graft core may have a proximal end width W2 at an end proximate the openings of the channels 2138*a*, 2138*b*, and a distal end width W1 at the distal end opposite the proximal end. As shown in FIGS. 76-78, widths W1 and W2 may be substantially the same for the graft core 2130 and the shell 2110. Furthermore, the graft core 2130 may have a proximal end depth D2 at an end proximate to the opening of the channels 2138*a*, 2138*b* and a distal end depth D3. As shown in FIGS. 76-78, in some examples, the depth D2 may be substantially the same as the proximal end distance D1 between the top and bottom members at the opening 2126 of the shell 2110, while the depth D3 may be substantially the same as the distal end distance D4 between the top and bottom members of the shell 2110. In other examples, the depth D2 of the graft core 2130 may be slightly greater than the distance D4 of the shell opening 2126, and the depth D3 may be slightly greater than the distance D4 of the shell 2110. Accordingly, when the graft core is inserted into the shell 2110, as shown in FIG. 77, and others, the graft core is secured in the shell with a friction fit.

In some examples, as discussed above, the connecting member 2114 of the shell 2110 may be formed of a resilient or flexible material such that when the graft core 2130 is inserted into the shell 2110, the connecting member 2114 may flex in order to allow the top and bottom members 2112*a*, 2112*b* to engage and receive or secure the graft core 2130 within the shell 110.

Figure 84:
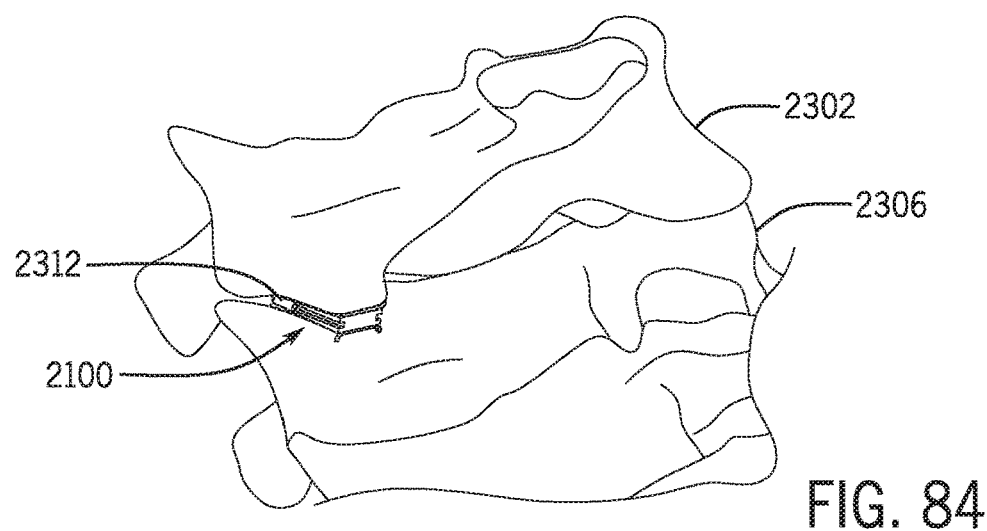
FIG. 84 is a perspective view of the spinal implant of FIG. 76 in a facet joint.
Figure 85:
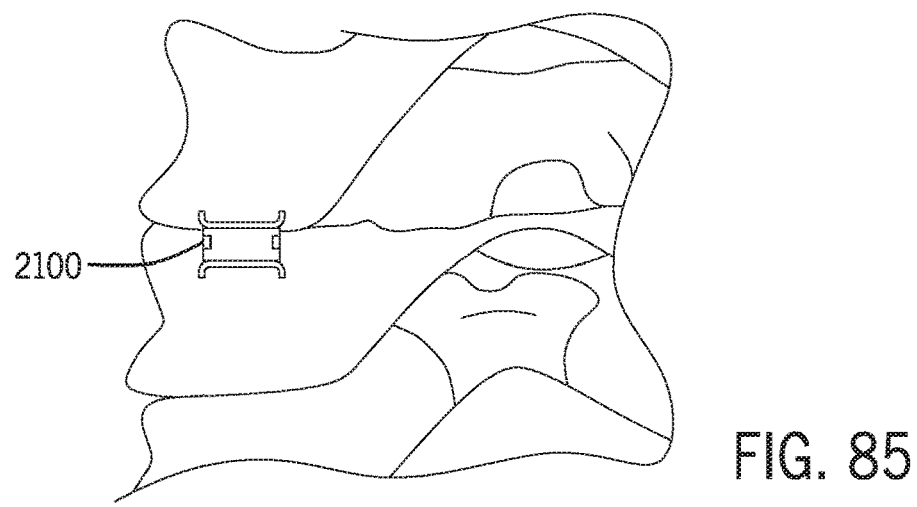
FIG. 85 is a side view of FIG. 84.
Figure 86:
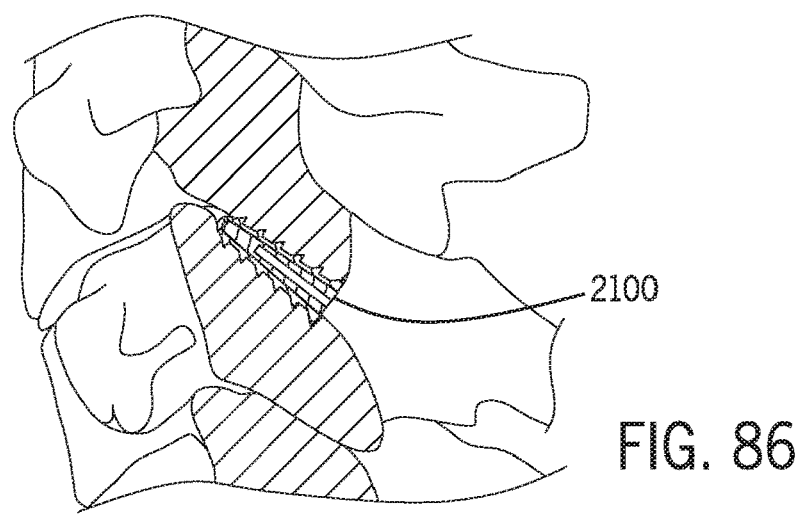
FIG. 86 is a cross-sectional view of the spinal implant of FIG. 76 in a facet joint.

Referring to FIGS. 84-86, a portion of a human spinal column is depicted with a spinal implant. A facet joint 2312 is defined between first and second vertebrae 2302, 2306. FIGS. 84 and 85 depict perspective and posterior views and FIG. 86 is a cross-sectional view of the spinal implant within the facet joint. As an example, the spinal implant 2100 is depicted within the facet joint 2312. However, it is noted that other spinal implants as disclosed herein may also be used.

Figure 87:
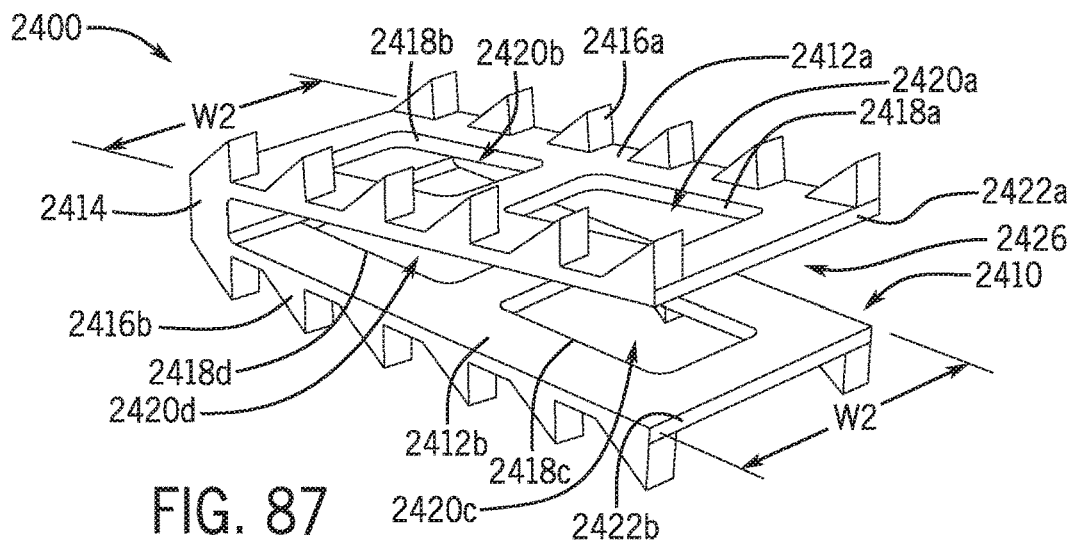
FIG. 87 is a perspective view of an implant shell in accordance with the present disclosure.
Figure 88:
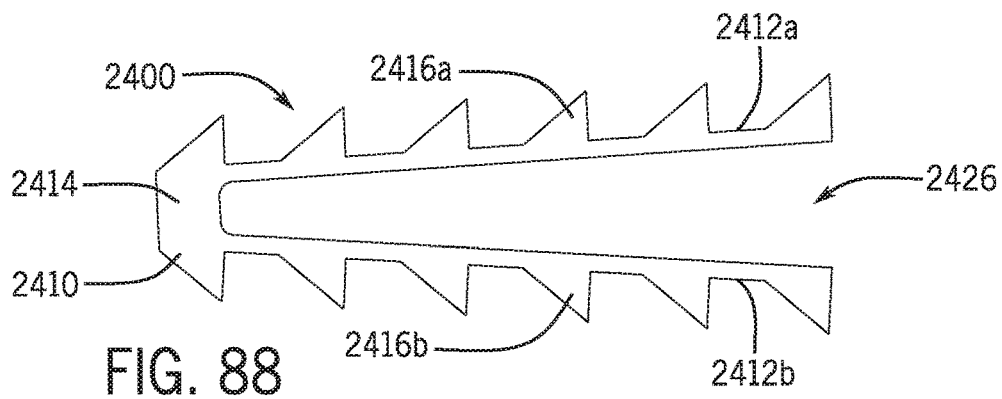
FIG. 88 is a side view of the spinal implant shell of FIG. 87.
Figure 89:
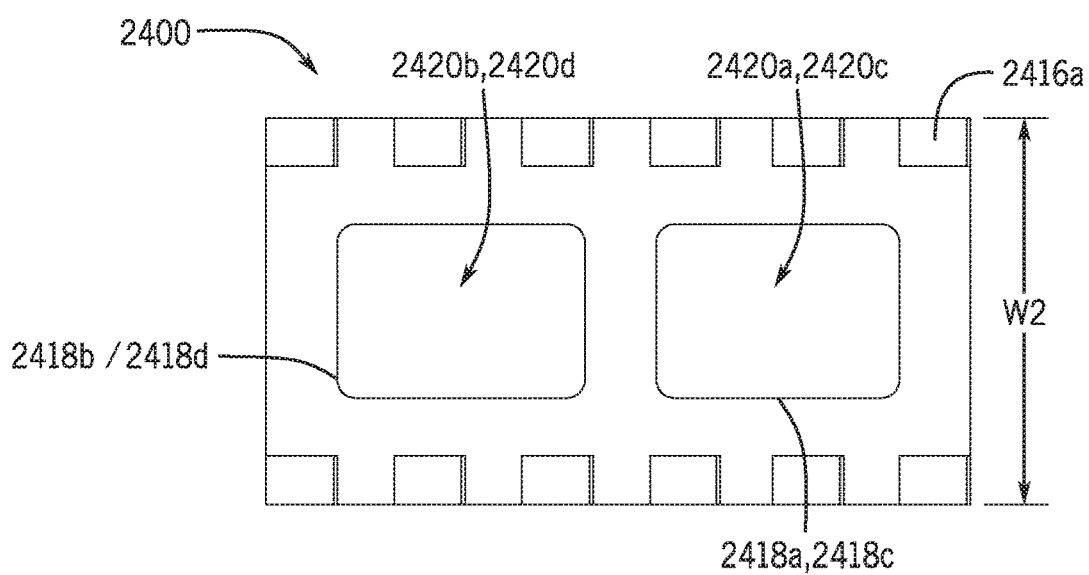
FIG. 89 is a top view of the spinal implant shell of FIG. 87.

Turning now to FIGS. 87-89, another example of a spinal implant 2400 is depicted. Similar to the example in FIGS. 76-83, the spinal implant 2400 may include an implant shell 2410 and a graft core (not shown, but substantially similar to graft core 2130 shown in FIG. 76 and described above). The implant shell 2410 includes a first or top member 2412*a* and a second or bottom member 2412*b*. The top and bottom members 2412*a*, 2412*b* may be coupled by a connecting member 2414. In some examples, the connecting member 2414 may be integral with the top member 2412*a* and bottom member 2412*b*. The shell 2410 may be made of a rigid material, and may be machined to form the desired shape. In one example, the top member 2412*a* and bottom member 2412*b* are angularly offset from one another. That is, the top member 2412*a* and bottom member 2412*b* may be coupled to form a shell 2410 with a wedge or tapered shape as viewed from the side (see FIG. 88), wherein the top and bottom members 2412*a*, 2412*b* are not parallel. For example, as shown in FIG. 88, the distance between the top and bottom members 2412*a*, 2412*b* at the distal end (near the connecting member 2414) is less than the distance between the top and bottom members 2412*a*, 2412*b* at the proximal end (near the opening 2426).

In some examples, the top and bottom members 2412*a*, 2412*b* of the shell 2410 may be substantially rectangular in shape. As shown in FIGS. 87 and 89, each of the top member and bottom member 2412*a*, 2412*b* of the shell 2410 may have a width W2. However, it is noted that the top and bottom members 2412*a*, 2412*b* may be substantially any other shape, including a tapered or wedge-shape. That is, similar to the example in FIGS. 76-80 discussed above, the top member 2412*a* and bottom member 2412*b* may be shaped with a perimeter which forms an overall trapezoidal shape (e.g. in a top view).

As depicted in FIGS. 87 and 89, the top member 2412*a* and bottom member 2412*b* of the shell 2410 include apertures 2418*a*, 2418*b* and 2418*c*, 2418*d*, defined therein. In some examples, the apertures 2418*a-d* may have a rectangular or square perimeter. As shown in FIG. 89, the corners of the apertures 2118*a-d* may be rounded. In other examples the apertures 2418*a-d* have an perimeter which substantially matches the perimeter of the top member 2412*a* and bottom member 2412*b*, respectively. However, the apertures 2418*a-d* may be substantially any shape, or combination of different shapes. The apertures 2418*a*, 2418*b*, 2418*c*, and 2418*d* are bone growth channels 2420*a*, 2420*b*, 2420*c*, 2420*d* because the graft core 2130 is exposed to surrounding tissue through these apertures.

The top and bottom members 2412*a*, 2412*b* may be provided with a plurality of engagement or attachment or fixation members, such as teeth or serration features, 2416*a*, 2416*b*. In some examples, the teeth 2416*a*, 2416*b* are positioned on the lateral edges of the top and bottom members 2412*a*, 2412*b*, and may be machined from the material of the shell 2410. The teeth 2416*a*, 2416*b* aid in fixation of the implant within the facet joint.

The shell 2410 may be made of a biocompatible material such as a biocompatible metal or plastic, such as titanium alloys or plastic. In one example, the material is substantially rigid. The shell 2410 has a selective radiopacity to allow the shell 2410 to be visualized with X-ray or other types of imaging. This enables a surgeon or other user to ensure proper location and fixation of the implant 2100 after placement.

The spinal implant 2400 further includes an allograft or graft core (not shown). The graft core may be substantially similar to the graft core 2130 of FIGS. 76-83 and is received within the shell 2410.

Figure 90:
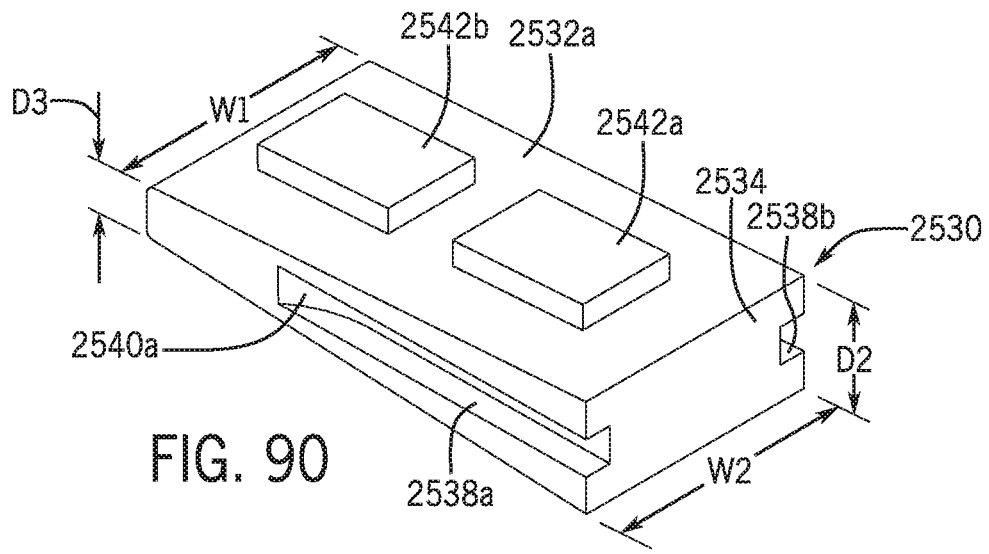
FIG. 90 is a perspective view of a graft core for use in a spinal implant according aspects of the present disclosure.
Figure 91:
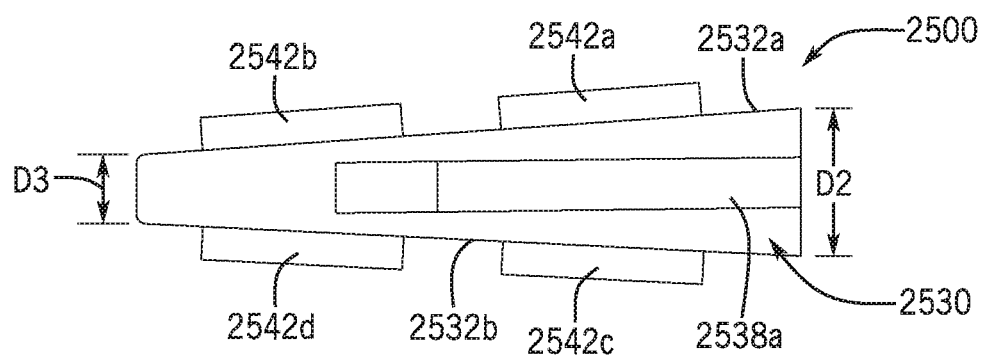
FIG. 91 is a side view of the graft core of FIG. 90.
Figure 92:
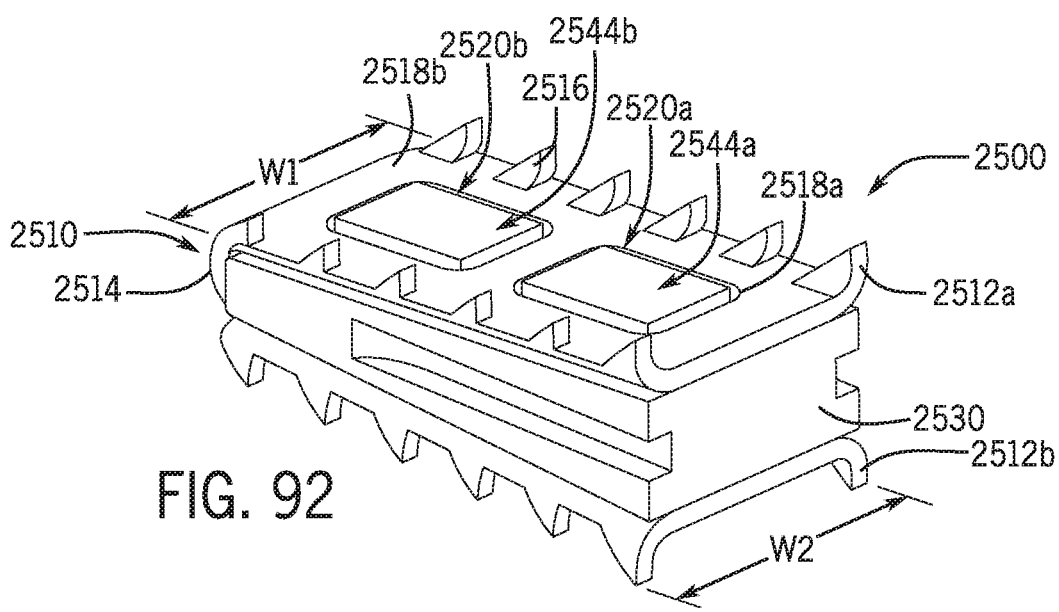
FIG. 92 is a perspective view of a spinal implant having the graft core of FIG. 90.

With reference to FIGS. 90-92, another example of a spinal implant 2500 is depicted. The spinal implant 2500 includes an implant shell 2510 and a graft core 2530. The implant shell 2510 may be substantially similar to the implant shell 2110 or 2410 and include a first or top member 2512*a* and a second or bottom member 2512*b* (FIG. 92). Similarly, the top and bottom members 2512*a*, 2512*b* are coupled by a connecting member 2514.

As depicted in FIG. 92, the top member 2512*a* and bottom member 2512*b* of the shell 2510 include apertures 2518*a*, 2518*b* and 2518*c*, 2518*d* (indicated in FIG. 91), respectively. In some examples, the apertures 2518*a*-*d* have a rectangular or square perimeter. In other examples, the apertures 2518*a*-*d* may be another shape, or combination of different shapes. The apertures 2518*a*, 2518*b*, 2518*c*, and 2518*d* define bone growth channels 2520*a*, 2520*b*, 2520*c*, 2520*d* in that the graft core 2530 is exposed to the surrounding tissue via the channels to aid in osteoconduction.

The top and bottom members 2512*a*, 2512*b* include a plurality of engagement or attachment or fixation members, such as serrated features or teeth 2516. In some examples, the teeth 516 are positioned on the lateral edges of the top and bottom members 2512*a*, 2512*b*, respectively. The teeth 2516 help to fix the implant in the facet joint.

The shell 2510 is made of metal, such as titanium, or plastic or other suitable biocompatible material that is generally rigid. Furthermore, the shell 2510 material has a selective radiopacity, to allow the shell 2510 to be visualized with X-ray or other types of imaging. This enables a surgeon or other user to ensure proper location and fixation of the implant 2500 after placement.

Figure 93:
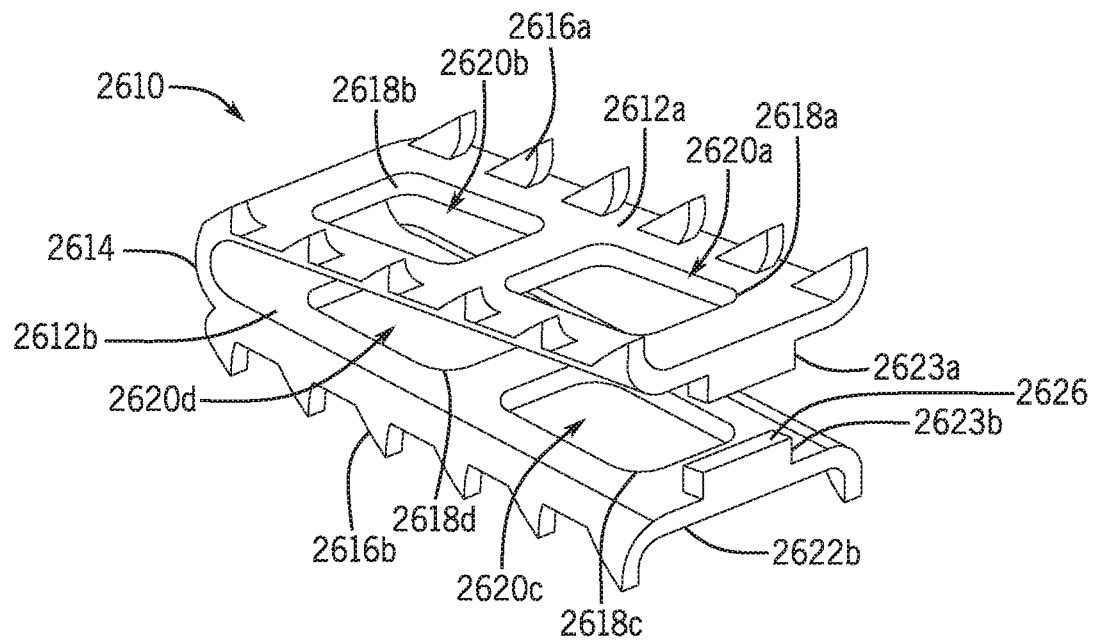
FIG. 93 is a perspective view of an implant shell according to aspects of the present disclosure.

The spinal implant 2500 further includes an allograft or graft core 2530. The graft core 2530 may be substantially similar to the graft core 2130, 2430. As depicted in FIGS. 91-93, the graft core 2530 is shaped for receipt in the shell 2510. The graft core 2530 is formed by machining or other appropriate manufacturing techniques. In some examples, the graft core 2530 includes channels 2538*a*, 2538*b* at least partially defined in opposite lateral faces of the graft core 2530. The channels 2538*a*, 2538*b* include a tapered portion 2540*a*, 2540*b* at distal ends of the channels 2538*a*, 2538*b*. The channels 2538*a*, 2538*b* may be sized and shaped to couple with a graft core 2530 installation tool, as discussed below, and may be centered along the depth D2 at the proximal end of the graft core 2530. The installation tool may be similar to the DTRAX Allograft Delivery Instrument or a similar tool having an elongated body with a lumen defined therein. Exemplary installation tools are described in more detail below.

In some examples, the graft core 2530 further includes a plurality of protrusions 2542*a*, 2542*b*, 2542*c*, and 2542*d*. The protrusions 2542*a*-*d* are formed when the graft core is formed. As shown in FIGS. 90-92, protrusions 2542*a*-*d* protrude from upper and lower planar surfaces of the bone graft 2530. In some examples, the protrusions 2542*a*-*d* are matingly received in the apertures 2518*a*-*d* of the shell 2510. Protrusions 2542*a*-*d* secure the graft core 2530 within the shell 2510. In some examples, the protrusions 2542*a*-*d* of the graft core 2530 are flush with the top and bottom members 2512*a*, 2512*b* of the shell 2510. As such, the graft core is exposed to the surrounding tissue to aid in osteoconduction.

Referring now to FIGS. 93-96, another example of a spinal implant 2600 is depicted. The spinal implant 2600 includes an implant shell 2610 and a graft core 2630. The implant shell 2610 may be similar to the implant shell 2110 of FIGS. 76-83 in some respects. For example, the implant shell 2610 includes a first or top member 2612*a* and a second or bottom member 2612*b*. The top and bottom members 2612*a*-*b* are coupled by a connecting member 2614. In addition, the top member 2612*a* and bottom member 2612*b* of the shell 2610 include apertures 2618*a*-*d*. In some examples, the apertures have a rectangular or square perimeter. The apertures 2618*a*-*d* form bone growth channels 2620*a*-*d* by allowing the graft core to be exposed to or contact the surrounding tissues to promote osteoconduction. Similar to the shell 2110 in FIGS. 76-80, top and bottom members 2612*a*, 2612*b* include a plurality of engagement or attachment or fixation members such as teeth 2616*a*, 2616*b*.

Figure 94:
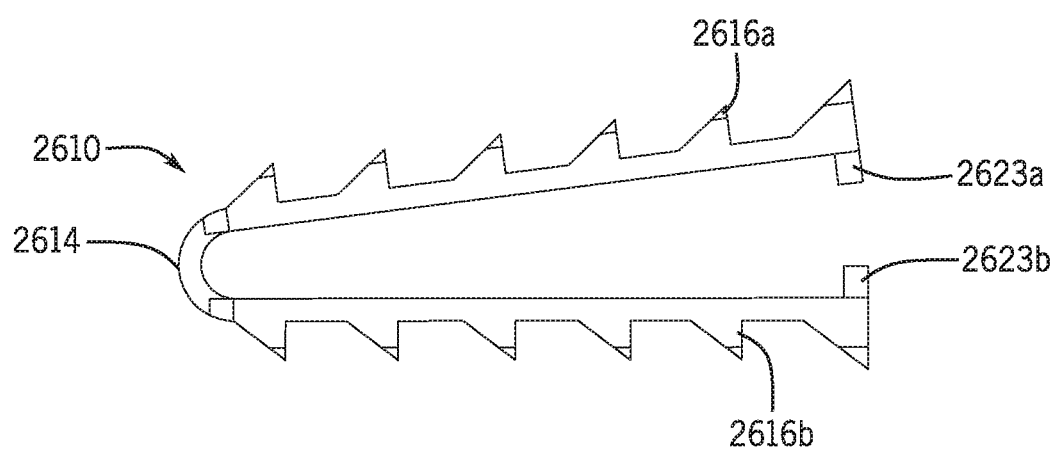
FIG. 94 is a side view of the implant shell of FIG. 93.

In one example, as shown in FIGS. 93 and 94, the top member 2612*a* and bottom member 2612*b* of shell 2610 include at least one retention tab 2623*a*, 2623*b*. The retention tabs 2623*a*,*b* are positioned at the proximal end of the shell 2610 near the opening 2626 of the shell 2610. Retention tabs 2623*a*-*b* are received in corresponding recesses in the graft core 2630.

The shell 2610 is made of any biocompatible material, such as titanium alloys or plastic. The material may be flexible, rigid or semi-rigid. Furthermore, the shell 2610 has a selective radiopacity to allow the shell 2610 to be visualized with X-ray or other types of imaging. This enables a surgeon or other user to ensure proper location and fixation of the implant 2600 after placement.

Figure 95:
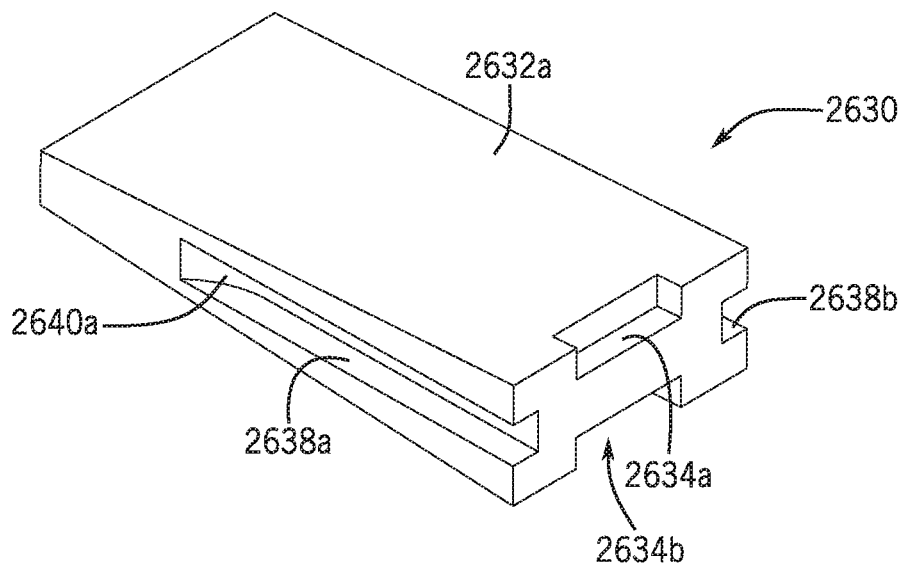
FIG. 95 is a perspective view of a graft core for use with the implant shell of FIG. 93.
Figure 96:
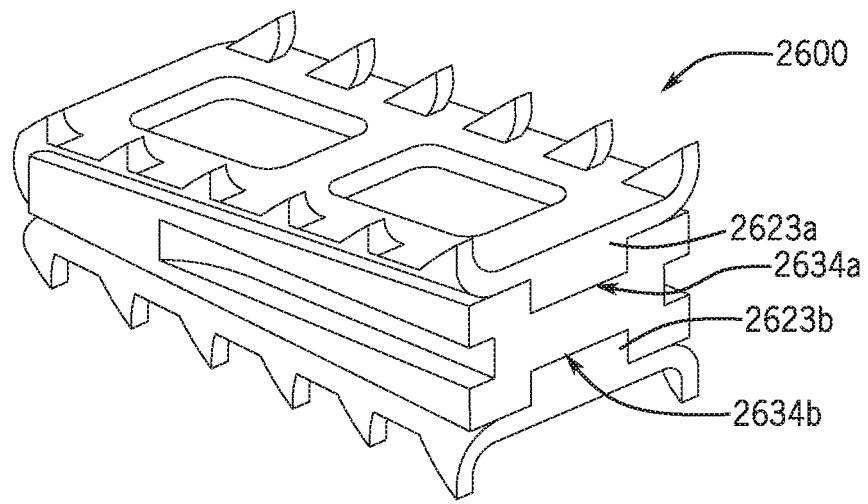
FIG. 96 is a perspective view of an assembled spinal implant having the shell of FIG. 93 and the graft core of FIG. 95.

As depicted in FIGS. 95-96, the spinal implant 2600 further includes an allograft or graft core 2630. The graft core 2630 may be sized and shaped for receipt in the shell 2610. The graft core 2630 may be formed by machining or other appropriate method. In some examples, the graft core 2630, includes channels 2638*a*, 2638*b* at least partially defined in opposite lateral faces of the graft core 2630, 2730. The channels 2638*a*, 2638*b* include a tapered portion 2640*a*, 2640*b* provided at distal ends of the channels 2638*a*, 2638*b*. The channels 2638*a*, 2638*b* may be sized and shaped to couple with a graft core 2630 installation tool. The installation tool may be similar to the DTRAX Allograft Delivery Instrument or a similar tool having an elongated body with a lumen defined therein. Exemplary installation tools are described in more detail below. The graft core 2630 is shaped for receipt in the shell 2610. The graft core 2630 also includes recesses 2634*a*, 2634*b*. The recesses 2634*a*-*b* matingly receive the retention tabs 2623*a*,*b* of the shell 2600, as shown in FIG. 96.

Figure 97:
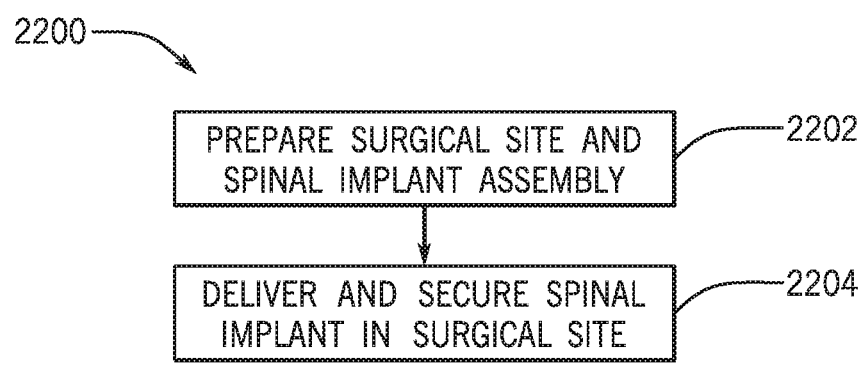
FIG. 97 is a flowchart describing a method for using an implant in accordance with the present disclosure.
Figure 98:
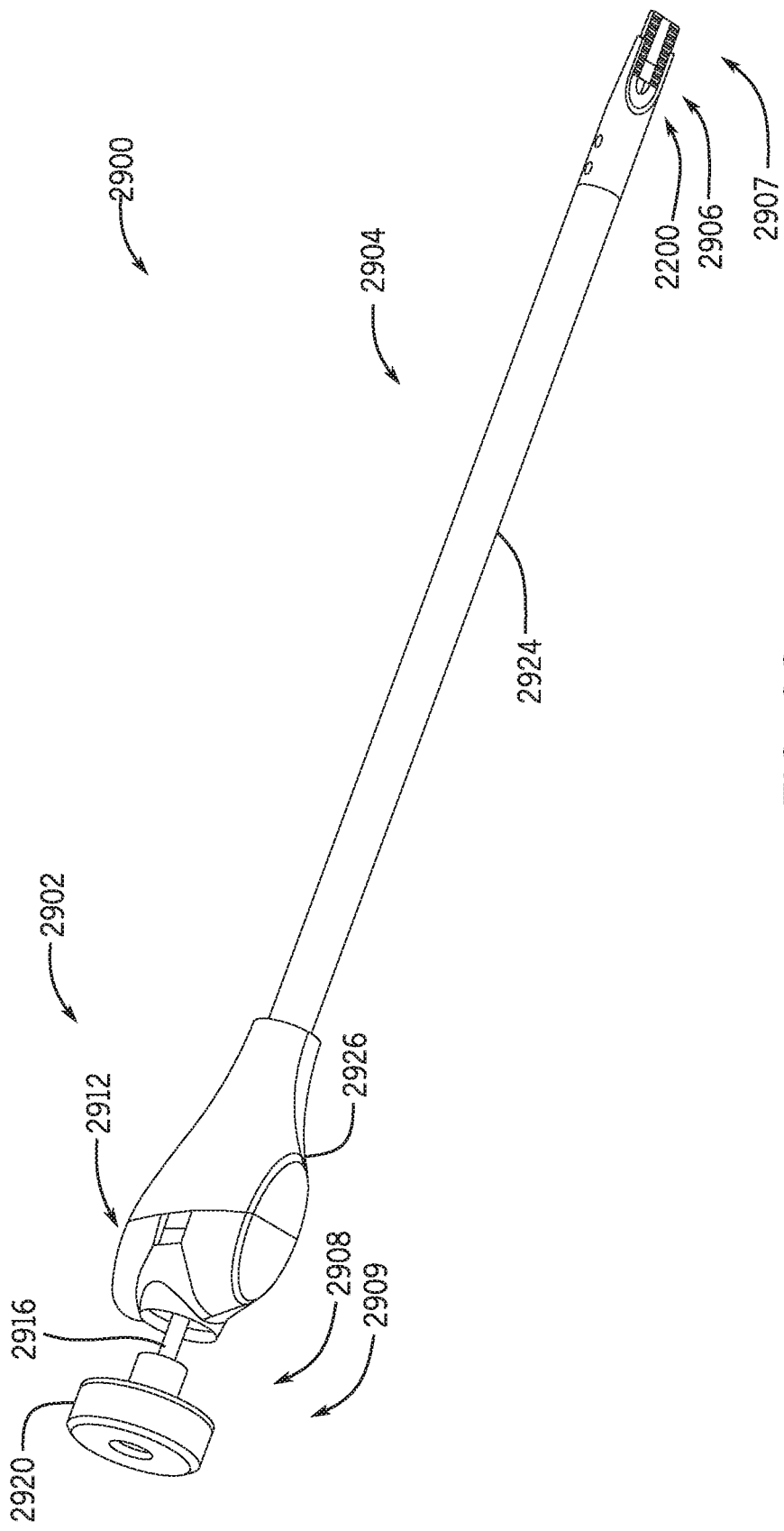
FIG. 98 is an example delivery device and guide tool configured to minimally invasively deliver a facet joint implant, according to certain embodiments.

Turning now to the flowchart of FIG. 97, a method 2200 of using a spinal implant is discussed. In one example, the method 2200 begins at step 2202 with preparing a surgical site and a spinal implant. In some examples, the surgical site which is prepared for the implant may be a cervical facet joint. In some examples, a user may prepare the vertebrae by scratching or roughening the surface of the vertebrae to cause the bone to bleed. This may help to promote both bone growth and fusion of the vertebrae with the graft core of the spinal implant.

To prepare the spinal implant, a graft core may be prepared. In one example, the implant may be substantially similar to the spinal implant 2100 discussed above and the graft core may be substantially similar to the graft core 2130 discussed with respect to FIGS. 76-83 or other allograft cores as described herein. The graft core may be formed by machining or other appropriate manufacturing method. The graft core is shaped for receipt within a shell, such as a shell and graft core described herein.

To continue preparation of the spinal implant of step 2202, the shell, such as a shell described herein, may be assembled. Once the shell is assembled, the graft core is inserted into the shell in order to assemble the spinal implant. Accordingly, the assembly of the spinal implant may be similar to the depictions of FIGS. 76-78 wherein the graft core 2130 is received in the opening 2126 of the shell 2110 to form the assembled spinal implant 2100 (see FIG. 78).

Once step 2202 is completed such that the surgical site and spinal implant are prepared, the method 2200 proceeds to step 2204 wherein the spinal implant is delivered to the surgical site, such as a cervical facet joint. The spinal implant, such as an implant discussed herein, includes fixation members, such as teeth, which secure the spinal implant within the facet joint. The spinal implant may be delivered by a distraction system, such as the distraction system described in more detail with reference to FIGS. 98-106b, 107 and 108-109.

As can be understood from FIGS. 98-106b, a distraction system 2900 is configured to minimally invasively or percutaneously deliver implementations of the spinal implant 2100 into a spinal facet joint space via, for example, a posterior approach. In one implementation, the system 2900 includes a delivery tool 2902 and a guide tool 2904, both of which extend from a respective leading distal end 2906, 2907 to a respective trailing proximal end 2908, 2909. As can be generally understood from FIGS. 84-86, the delivery tool 2902 can be received in the lumen of the guide tool 2904 to bring about the delivery of the implant 2200 into the target spinal facet joint. The system 2900 may further include a decorticator 2936, an injector or push rod 2948, a chisel 2960, a place holding chisel 2974, and a mallet 2980.

Figure 99:
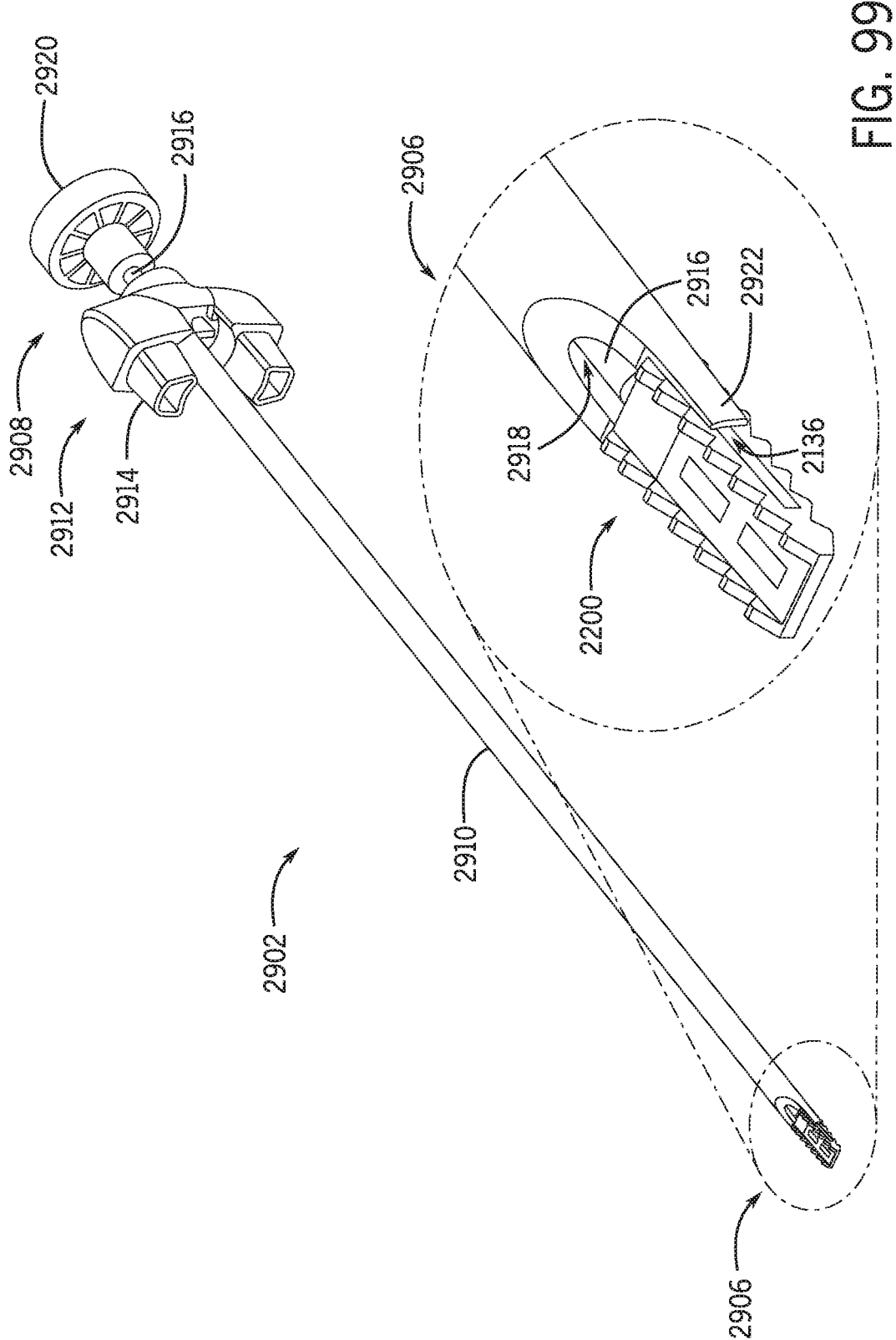
FIG. 99 is a perspective view of the delivery device of FIG. 98 and a detailed view of a distal end of the delivery device.

For a detailed description of the delivery tool 2902, reference is made to FIG. 99. In one implementation, the delivery tool 2902 includes a tubular body 2910 with a handle arrangement 2912 at the trailing proximal end 2908. The handle arrangement 2912 may further include one or more members 2914 for engaging the guide tool 2904. In one implementation, a plunger 2916 extends through a lumen 2918 of the tubular body 2910 and includes a handle 2920 at the trailing proximal end 2906. The plunger 2916 may be used to distally push the implant from an interference fit engagement with the arms 2922 of the delivery tool distal end 2906.

In one implementation, the tubular body 2910 at the leading distal end 2906 includes opposed prongs 2922 between which the implant, including the distal leading portion 2100 and the proximal trailing anchor portion 2200, may be supported. The prongs 2922 include longitudinally extending ridges that are adapted to be received into and engage the respective slots 2138 of the implant 2100. In one implementation, the plunger 2916 is spring biased to keep the plunger 2916 proximally displaced in the lumen 2918 of the tubular body 2910, such that distal force exerted against the handle 2920 causes the plunger 2916 to distally displace to eject the implant from the tubular body 2910 at the leading distal end 2906.

Figure 107:
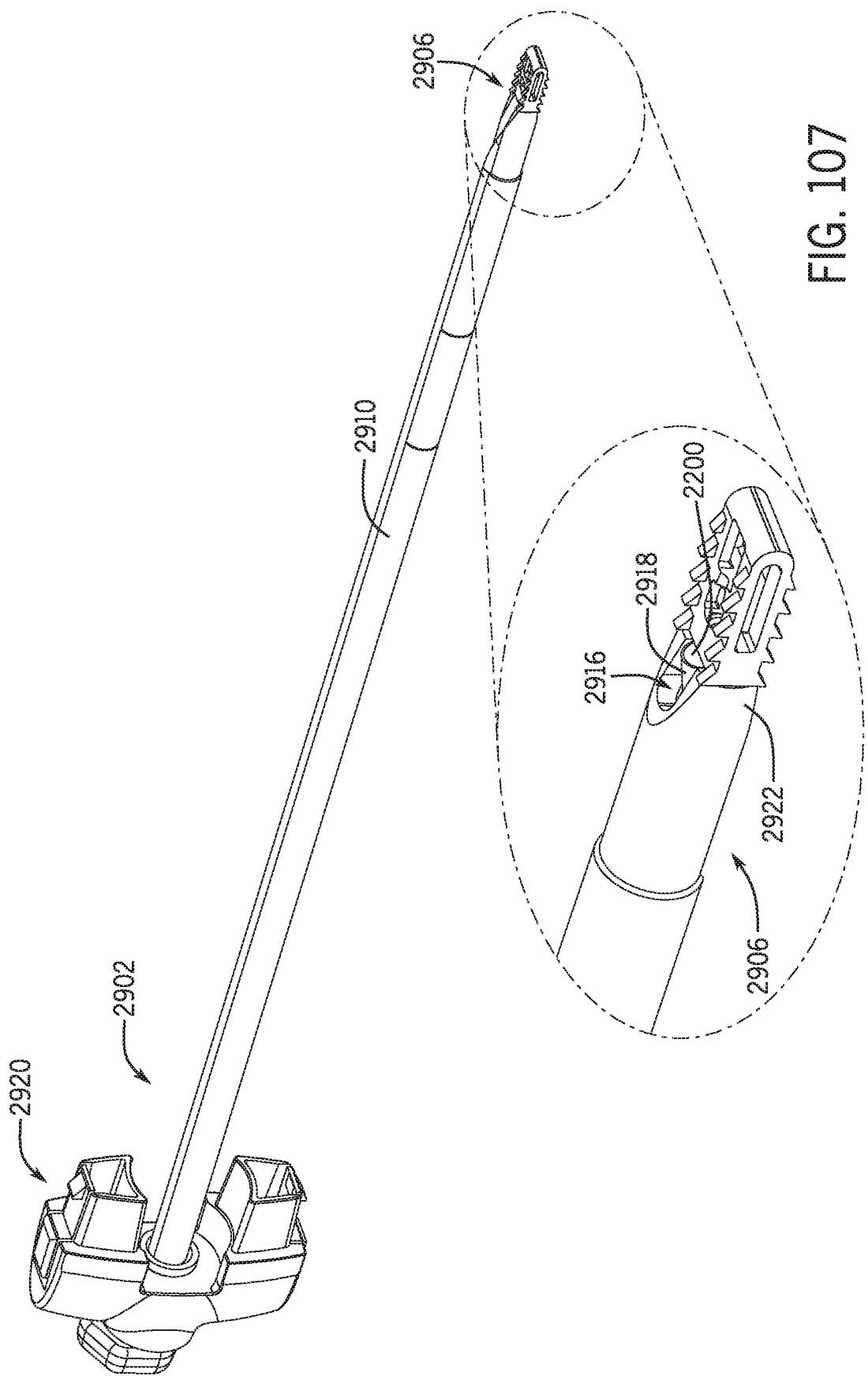
FIG. 107 is an example delivery device and a detailed view of a distal end of the delivery device.

In one implementation shown in FIG. 107, the tubular body 2910 at the leading distal end 2906 includes opposed arms or distal features, such as distal engagement features, 2922 at which the proximal trailing anchor portion 2200 may be received and/or supported. In one implementation, a rod 2916 is spring biased to keep the rod 2916 proximally displaced in the lumen 2918 of the tubular body 2910, such that distal force exerted against the handle 2920 causes the rod 2916 to distally displace and rotate to release the implant from the tubular body 2910 at the leading distal end 2906. The leading distal end 2906 may be coupled to the implant by a threaded male member that engages with a female threaded socket within the implant; or a threaded male implant that engages with a female threaded socket on the tubular body; or an interference fit; or a spring clamp, wedge, or hook that engages with a feature of the implant, etc.

Figure 100:
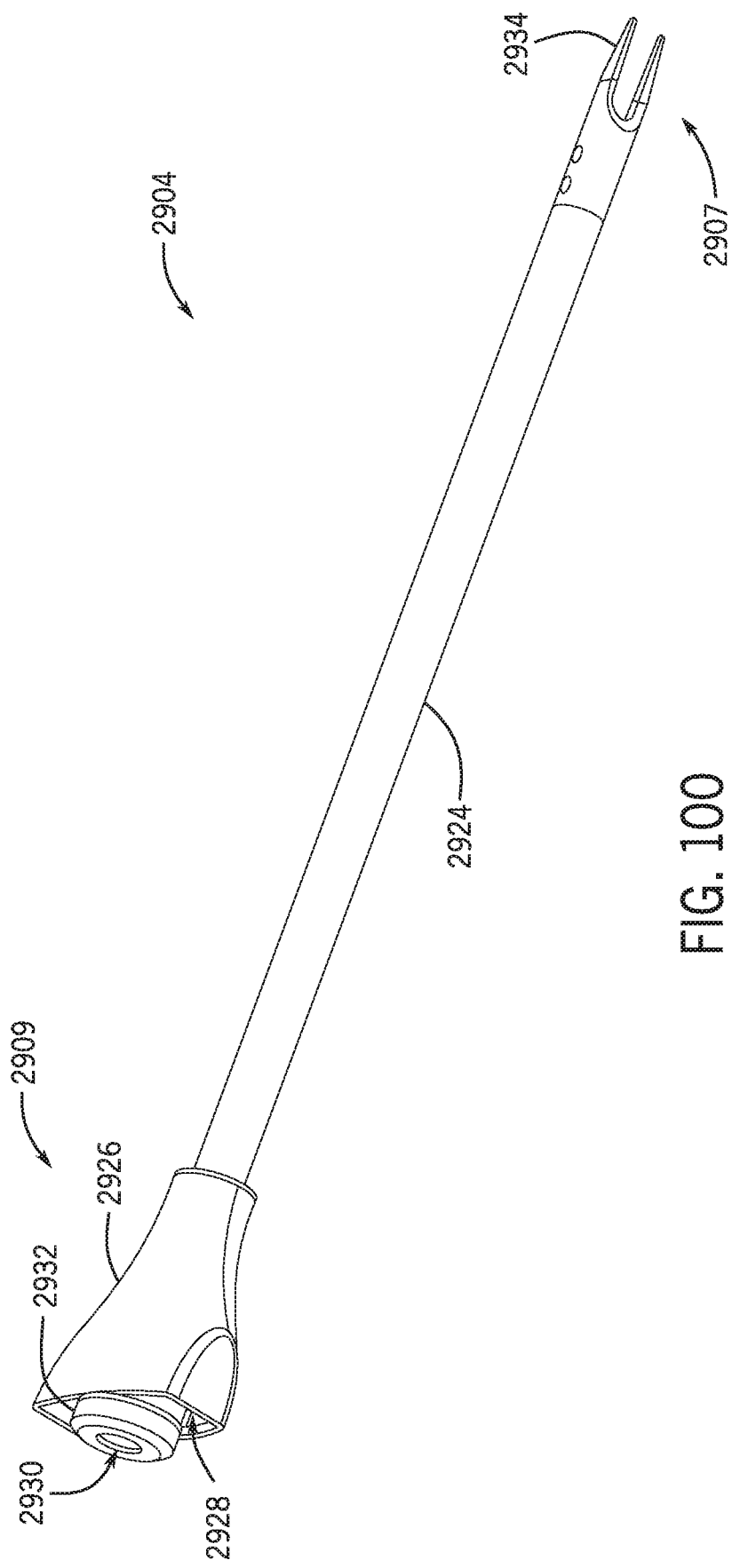
FIG. 100 is a perspective view of the guide tool of FIG. 98.

Turning to FIG. 100, a detailed description of the guide tube or tool 2904 is provided. In one implementation, the guide tool 2904 includes a receiving assembly 2926 at a proximal end 2909 and a pair of anchoring forks 2934 at a distal end 2907 with a generally tubular shaft 2924 extending there between. The anchoring forks 2934 may be textured distal parallel prongs for accessing a spinal facet joint and through which the delivery tool 2902 can be routed to deliver the implant 2100 in the facet joint.

The guide tool 2904 can also include a malleting anvil 2930 having a raised surface 2932 positioned on the proximal face of the receiving assembly 2926 adapted for contact with a distal end of a malleting head 2966 on the chisel 2960 or on the delivery tool 2902. Malleting on the proximal end of the chisel 2960 or the delivery tool 2902 can cause longitudinal forces along the length of the respective tool piece. These longitudinal forces can be transferred, at least partially, through the contact between the malleting head and the malleting anvil 2930. Accordingly, relative motion between the respective tool piece and the guide tool 2904 can be prevented. As such, for example, at the distal end 2907 of the guide tool 2904, the relative position of the distal end 2972 of the chisel 2960 or the delivery tool 2902 relative to the distal end 2907 of the guide tool 2904 can be maintained. Further, in one implementation, the receiving assembly 2926 includes a receiving portion 2928 for receiving and engaging the members 2914 or 2970 of the delivery tool 2902 and the chisel 2960.

Figure 101:
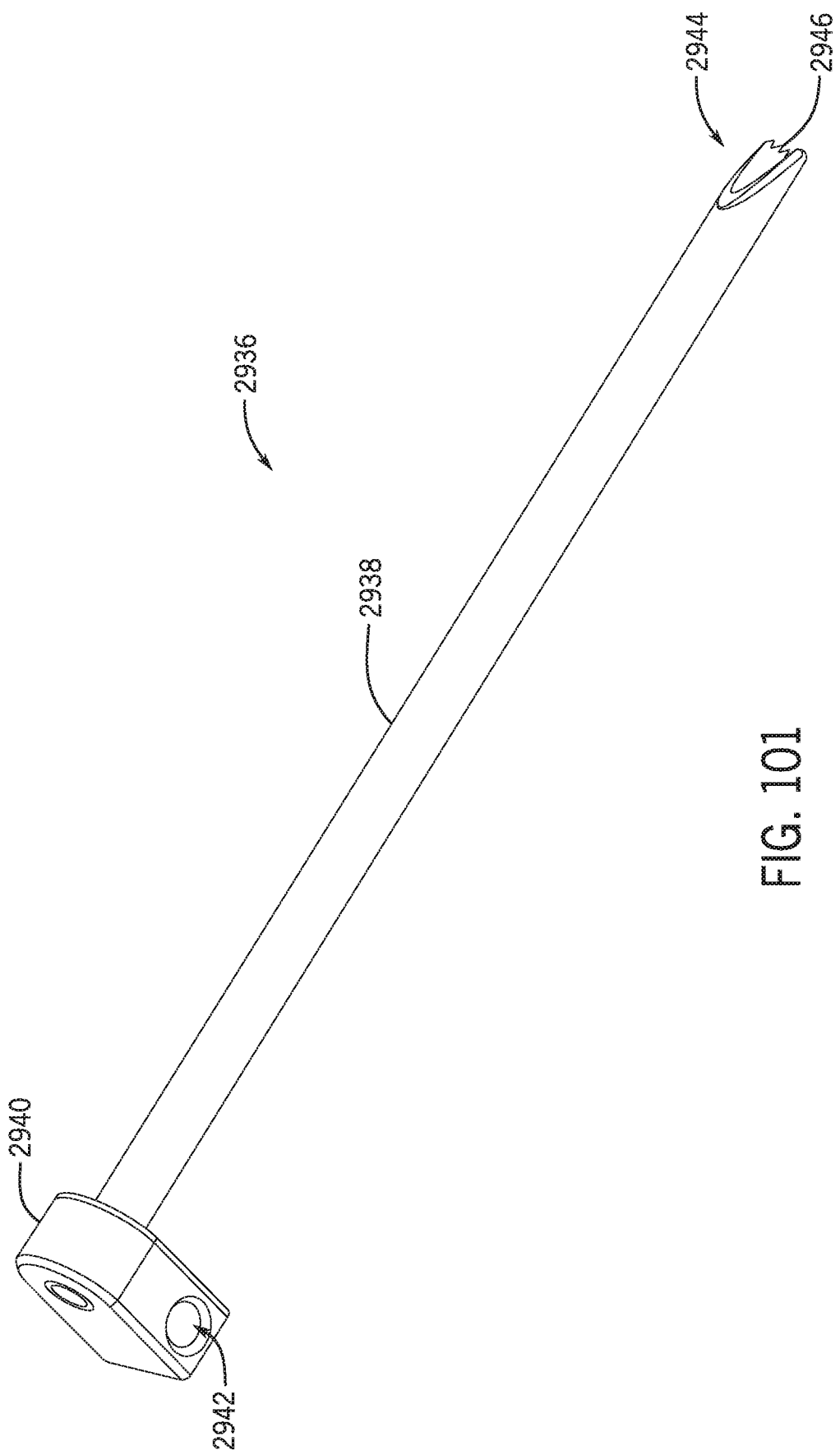
FIG. 101 is a perspective view of an example decorticator.

As can be understood from FIG. 101, in one implementation, the decorticator 2936 includes a tubular shaft portion 2938, an abrasive distal end 2944, and a handle 2940 at a proximal end. The tubular shaft 2938 may have an inner radius substantially equal to an outer radius of the shaft 2976 of the place holding or guide chisel 974 of FIG. 104 and may allow for sliding movement of the decorticator 2936 along the length of the chisel shaft 2976 and rotationally around the chisel shaft 2976. In some implementations, the inner radius of the tubular shaft 2938 may be slightly or substantially larger than the outer radius of the shaft 2976 of the chisel 2974 allowing for more freedom of movement of the decorticator 2936.

The abrasive distal end 2944 of the decorticator 2936 may include serrated teeth 2946 as shown, or may include a more flat annular surface with a gritty surface. In the implementation shown in FIG. 101, the distal end of the tubular shaft portion 2938 is chamfered and the serrated teeth 2946 are located on the distal-most end of the chamfered end, allowing for a more directed and controllable decorticating process. As such, the decorticator 2936 shown is well suited for the intra-facet process reflected by many of the implementations described herein.

Additionally, to properly place the prongs 2934 of the guide tube 2904 within the joint, the guide chisel 2974 may be positioned substantially parallel to articular surfaces of the facet joint. As such, the place holding or guide chisel 2974 may not be positioned perpendicular to the lateral masses of the facet joints and may actually be directed with a downward slope as it extends in the distal direction. Where the decorticator 2936 has a non-chamfered annular end, depending on anatomy, the decorticator 2936 may be able to be placed in contact with the superior lateral mass, but may be unable to reach or contact the inferior lateral mass. In the present implementation, the chamfered end of the tubular shaft portion 2938 will allow the distal tip of the chamfered end to reach and decorticate the inferior lateral mass. This chamfered distal end may define an angle to the longitudinal axis. Additionally, the teeth 2946 may be relatively large or they may relatively small and may extend along the full perimeter surface of the chamfered end rather being positioned solely at the tip of the chamfered end. Additionally, a beveled edge may run along the periphery of the chamfered end. That is, along the ovular shape created by the chamfered tubular shaft portion 2938, the edge is beveled. As such, when the chisel 2974 is inserted into the patient and/or when the decorticator 2936 is advanced along the chisel 2974, the beveled edge may assist in avoiding tissue snags, and the decorticator 2936 may be placed in contact with the lateral mass of the facet joints in a much smoother process and may avoid damage to neighboring tissues.

The handle 2940 of the decorticator 2936 may include a gripping surface along its peripheral edge and may receive the tubular shaft portion 938 in a sleeve-like manner. The handle 2940 may also include radially extending bores 2942 adapted to receive a gripping tool to provide for better control and a higher amount of torsional leverage when decorticating the lateral masses of the facet joint or to allow for malleting in the longitudinal direction of the decorticator 2936 to cause forceful decortication of the lateral mass. The decorticator 2936 may then be retracted, rotated to a new radial position, advanced, and struck again for additional decortication.

Figure 102:
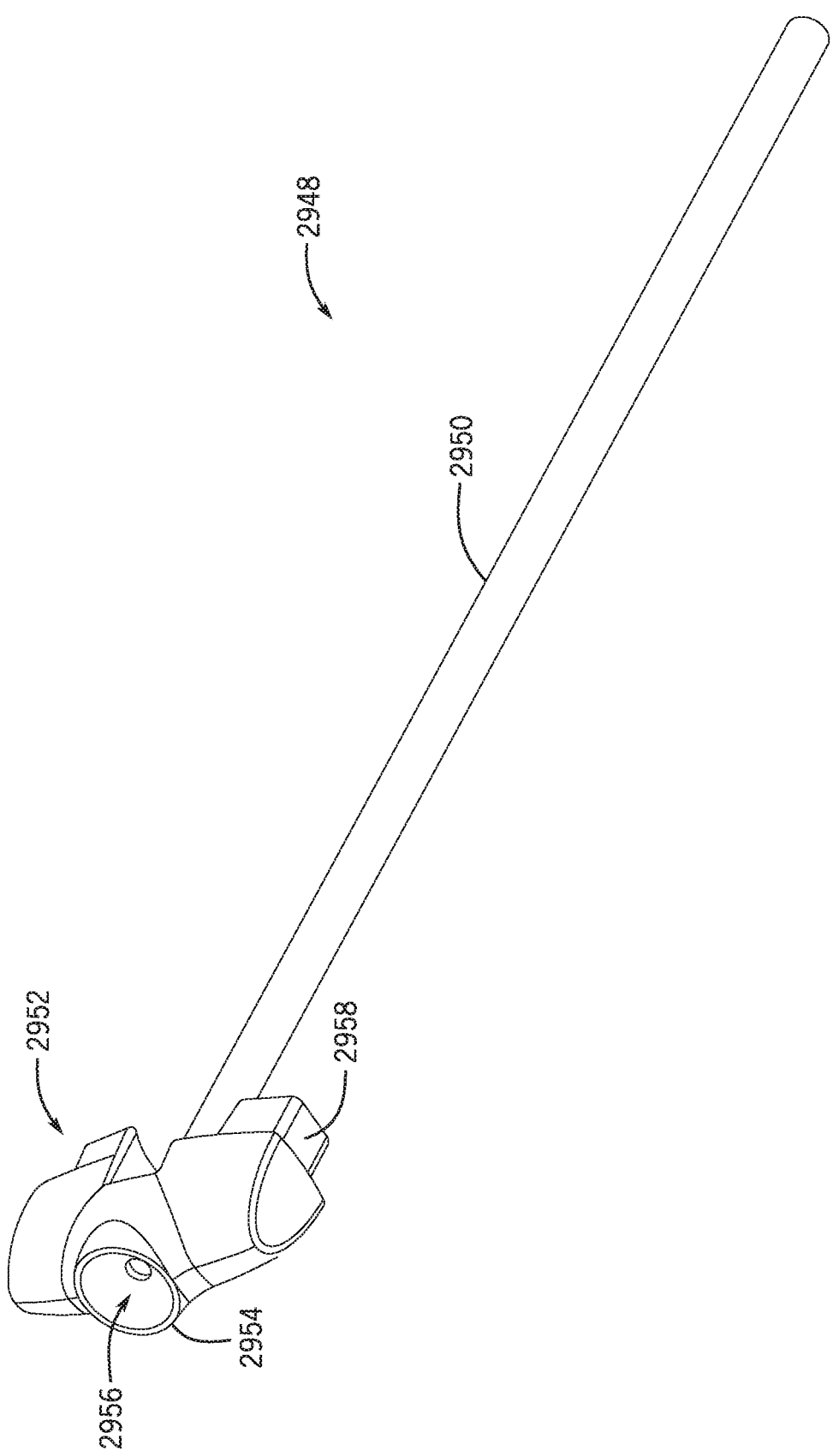
FIG. 102 is a perspective view of an example injector or push rod.

Referring to FIG. 102, in one implementation, the injector 2948 includes a longitudinal delivery shaft 2950 and a seating feature 2952. The longitudinal delivery shaft 2950 may have any cross-sectional shape and size adapted to fit within the guide tool 2904. The longitudinal shaft 2950 may have an opening 2956 on its distal end 2954 for directing bone paste out the distal end of the shaft 2950 allowing the paste to flow into and/or over the facet joint and/or outward toward the lateral mass of a facet joint. The seating feature 2952 may include a member 2958 positioned around the shaft 2950, which may be sized and shaped to abut the receiving portion 2928 of the guide tool 2904. The injector 2948 may be inserted into the guide tool 2904 and advanced, such that the distal end of the shaft 2950 is positioned between the prongs 2934.

In other embodiments, the injector 2948 shown in FIG. 102 is a push rod having either a solid or hollow longitudinal delivery shaft 2950 and a seating feature 2952. The longitudinal delivery shaft 2950 may have any cross-sectional shape and size adapted to fit within the guide tool 2904. The seating feature 2952 may include a member 2958 positioned around the shaft 2950, which may be sized and shaped to abut the receiving portion 2928 of the guide tool 2904. The push rod injector 2948 may be inserted into the guide tool 2904 and advanced, such that the distal end of the shaft 2950 is positioned between the prongs 2934.

Figure 103:
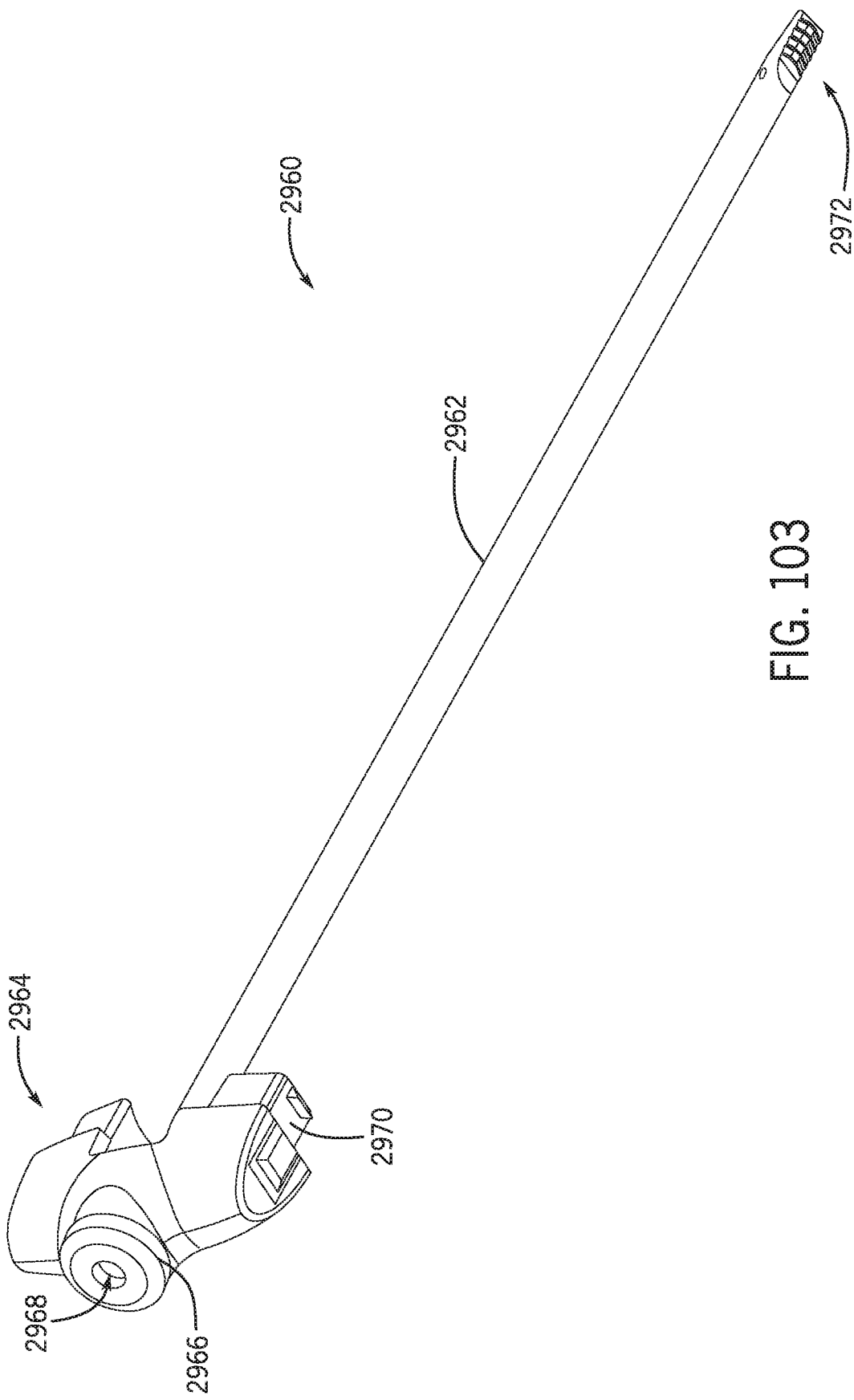
FIG. 103 is a perspective view of an example chisel.

As can be understood from FIG. 103, in one implementation, the chisel 2960 includes a generally cylindrical cross-section forming a shaft 2962, which may have a radius substantially equal to the inner radius of the tubular shaft portion 2924 of the guide tool 2904 allowing for slidable insertion of the chisel 2960 within the guide tool 2904. Alternatively, the radius of the shaft 2963 may be smaller than the inner radius of the tubular shaft 2924 providing for more play and adjustability of the chisel 2960 and the guide tool 2904 relative to one another. The chisel 2960 may include a single or doubly chamfered tip 2972 at a distal end or may have a coped distal end or a combination of coping and chamfering. The tip 2972 may include a roughened surface on one or more sides to aid in anchoring or docking the chisel in the facet joint. Additionally, this roughened surface may allow for roughening or decorticating the inner surfaces of the facet joint. The tip 2972 may have a length adapted to extend substantially across the facet joint.

The chisel 2960 may further include a handle assembly 2964 that may include a member 2970 positioned around the shaft 2962, which may be sized and shaped to abut the receiving portion 2928 of the guide tool 2904. The chisel 2960 may also include a longitudinally extending lumen 2968 and a malleting head 2966.

Figure 104:
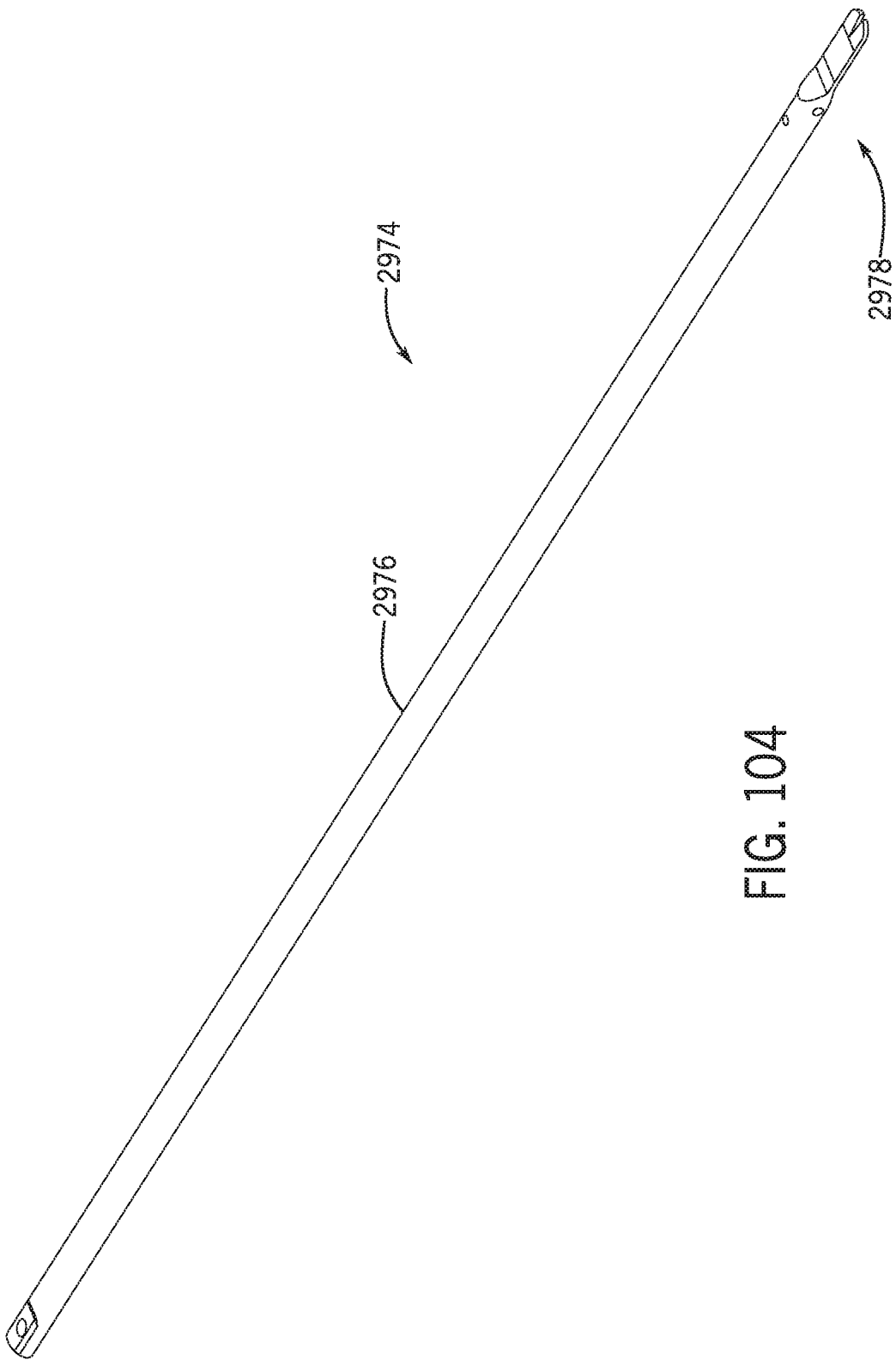
FIG. 104 is an example place holding chisel.

Turning to FIG. 104, in one implementation, the placing holding or guide chisel 2974 includes a shaft 2976 and a distal tip 2978, which may include a tip the same or similar to the chisel 2960. For example, the chisel 2974 can include a coped and/or chamfered tip. Additionally, the chisel 2974 can include ridges. Additionally, the chisel 2974 can include a radiopaque portion on the shaft 2976 adapted to allow recognition of the location of the chisel 2974 while avoiding occlusion of the lateral view. The radiopaque portion can include a straight, round, square, or other shaped piece of material positioned near the distal end of the chisel 2974 for locating the distal end. As also shown, the proximal end of the chisel 2974 can include a hole extending transversely therethrough. The hole can adapted to receive a transverse rod or shaft extending into the hole and/or through the hole. The rod or shaft and the chisel 2974 can form a T-grip or L-shaped grip for use in pulling on the chisel 2974 for removal.

In one implementation, the place holding chisel 2974 can be used as a place holder without occluding the lateral view of a chisel and delivery tool positioned in a contralateral facet joint. That is, upon placement of the chisel 2960 and the guide tool 2904 in a first facet joint, the chisel 2960 may be removed and replaced with the place holding chisel 2974 where the prongs 2934 of the guide tool 2904 maintain the position of the system 2900. The guide tool 2904 may also be removed and reassembled with the chisel 2960 once the place holding chisel 2974 is properly positioned. The guide tool 2904 and chisel 2960 may then be inserted into the contralateral facet joint or second joint. By replacing the chisel 2960 in the first joint with the place holding chisel 2974, the location of the chisel 2960 and guide tool 2904 in the second joint may be more readily ascertainable using lateral fluoroscopy. That is, if a radiopaque chisel or delivery device was left in place in the first joint, the fluoroscopic view of the contralateral facet joint would be relatively occluded. Upon placing the guide tool 2904 properly in the second facet joint, the procedure above may continue. Upon completing treatment of the second facet joint, the guide tool 2904 may be sleeved over the place holding chisel 2974 still positioned in and holding the place in the first facet joint and the first facet joint may then be treated with the above procedure. It is noted that initial placement of the guide tool 2904 can be conducted with the place holding chisel 2974 rather than the chisel 2960 to avoid having to replace the chisel 2960.

Referring to FIG. 105, in one implementation, the malleting tool 2980 can include a longitudinally shaped shaft with a U-shaped decorticator interface 2984 at one end and a chamfered tip 2982 at the other end. The decorticator interface 2984 can be adapted for positioning around the guide tool 2904 in a position just proximal to a malleting element of the decorticator 2936. The u-shape of the decorticator interface 2984 may allow the malleting tool 2980 to be placed in position from the side of the guide tool 2904 and selectively used as required to forcibly advance the decorticator 2936.

The chamfered end of the tool 2982 can be held in position while the user mallets near the decorticator interface end causing the interface 2984 to contact the malleting element on the decorticator 2936. The decorticator 2936 may then be retracted, rotated to a new radial position, advanced, and struck again for additional decortication. The malleting tool 2980 may rotate with the decorticator 2936 or it may remain in a position convenient for malleting. In addition to malleting, the malleting tool 2980 can be used to assist in separating several tools. That is, in some cases, the handles of a given tool piece can be difficult to separate from receiving portion. The chamfered tip 2982 can be used to wedge between a given handle and the receiving portion to assist in separating the devices.

Other implementations of a distraction system 2900 can be configured with alternative retaining and deployment (release or eject) methods, such as screw drives, latches, snaps, cams, adhesives, magnets, or the like.

The delivery system components depicted in FIGS. 98-105 can be used to minimally invasively implant an implant (according to any embodiments described herein) in a spinal facet joint that is the target of treatment. For example, in one embodiment, a percutaneous or minimally invasive incision is made in the posterior region of the neck to lead to the target facet joint. The access chisel 2974 depicted in FIG. 104 is routed through incision under fluoroscopic guidance until the tapered distal tip 2978 resides in the target facet joint and the chisel shaft 2976 extends out of the patient via the incision. With the access chisel 2974 so positioned, the outer decorticator 2936 of FIG. 91 can be grasped and distally routed over the access chisel 2974 such that the chisel shaft 2976 is received in the lumen that extends longitudinally through the outer decorticator 2936. With the distal decorticating end 2946 of the outer decorticator 2936 abutting against one or more lateral masses adjacent the target facet joint, the outer decorticator 2936 can be rotated about the chisel shaft 2976 to decorticate the bone surfaces of the lateral masses adjacent the target facet joint. Once decortication of the lateral masses has been sufficiently achieved, the decorticator 2936 can be removed from about the chisel shaft 2976 and from the patient.

With the place holding or access chisel 2974 so positioned, the guide tool 2904 of FIG. 100 is grasped and distally routed over the chisel 2974 such that the chisel shaft 2976 is received in the guide tool lumen that extends longitudinally through the guide tool shaft 2924. The tapered forked distal end 2907 of the guide tool 2904 is distally advanced through the incision and along the chisel shaft 2976 until the tapered forks 2934 of the guide tool 2904 are positioned inside the target facet joint, the chisel tapered distal tip 2978 being located between the pair of forks 2934 of the guide tool distal end 2907, the guide tool shaft 2924 extending out of the patient via the incision.

With the guide tool 2904 so positioned, the place holding or access chisel 2974 can be withdrawn out of the guide tool lumen and out of the patient, leaving the guide tool tapered forked distal end 2907 residing in the target facet joint and the guide tool shaft extending out of the patient. The decorticating chisel 2960 of FIG. 103 can then be distally routed through the lumen of the guide tool 2904 to place the tapered decorticating distal end 2972 of the chisel 2960 between the guide tool forks 2934 located in the target facet joint space. The decorticating chisel 2960 can then be displaced distal-proximal to cause the tapered decorticating distal end 2972 of the chisel 2960 to remove the cartilage of the target facet joint space located between the guide tool forks 2934 and further decorticate any associated bone surfaces of the target facet joint space. Once the target facet joint space surfaces have been prepped with the decorticating chisel 2960, the chisel 2960 can be removed from the lumen of the guide tool 2904 and the patient.

The implant 100 is coupled to, and supported at or by, the distal end 2906 of the implant delivery tool 2902 of FIG. 99, (see also FIG. 107, 108). As discussed above, the coupling of the implant delivery tool distal end 2906 with the implant 2200 may be achieved via an interference fit engagement, or a threaded connection, or etc. With the implant supported off of the distal end 2906 of the implant delivery tool 2902 in a manner similar to that depicted in FIG. 99, the implant 2100, and the delivery tool shaft 2910 on which the implant 2100 is supported, are distally routed through the lumen of the guide tool 2904 until the implant 2100 and the delivery tool distal end 2906 are located in the target facet joint space between the pair of forks 2934 of the guide tool distal end 2907, the delivery tool 2902, the guide tool 2904 and the implant 2100 being coupled together as depicted in FIG. 88. With the implant 2100 so positioned in the target spinal facet joint space, the plunger 2916 may be used to deposit the implant 2100 into the target spinal facet joint space by plunging the implant 2100 from the delivery tool distal end 2906 via corresponding manipulation of the plunger 2916 via its handle 2920. Once the implant 2100 is decoupled from the delivery tool 2902 and deposited into the facet joint space, the delivery tool 2902 can be withdrawn from the guide tool 2904, which is left in place with its forked distal end 2907 occupying the facet joint space and the implant 2100 being located between the forks 2934 of the guide tool 2904.

Figure 106A:
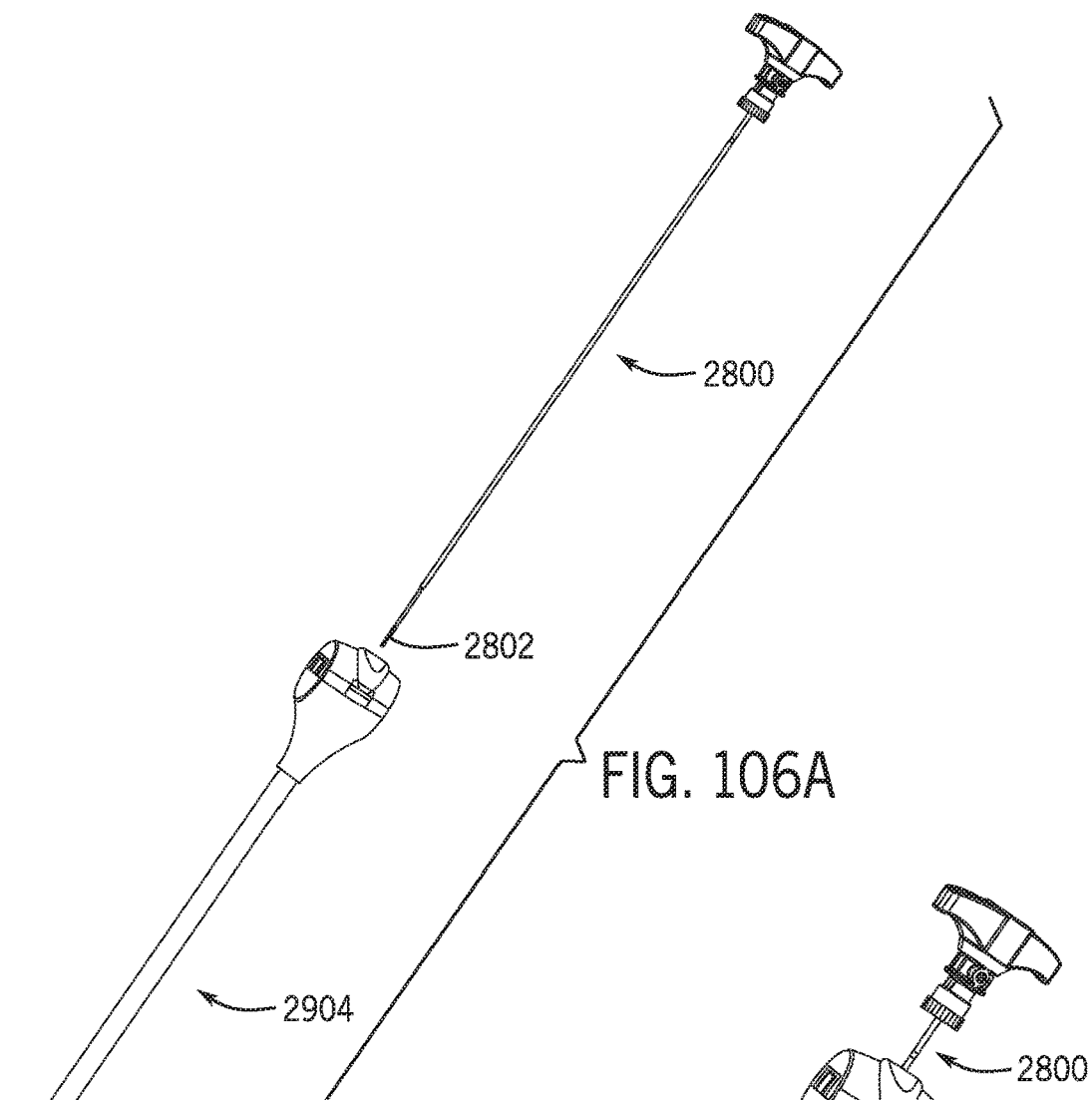
FIGS. 106a-106b are perspective views of the implant delivery device of FIG. 98, according to certain embodiments.
Figure 106B:
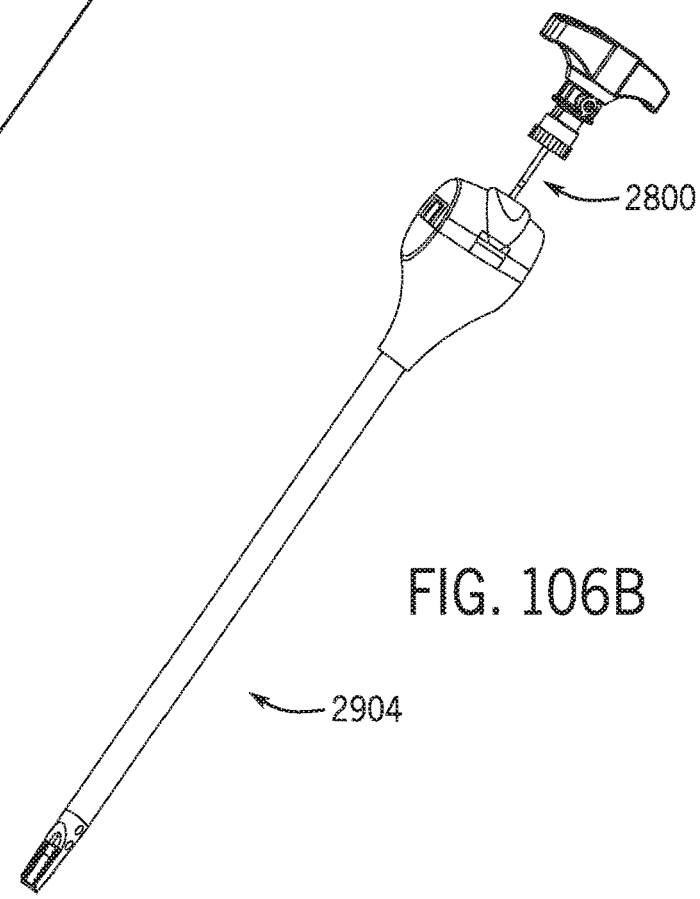

Now turning to FIGS. 106a-106b, when the delivery tool 2902 is withdrawn from the guide tool 2904, and the implant 2100 is located between the forks of the guide tool 2904, a user may insert the implant delivery device 2300 through the lumen of the guide tool 2904 to deliver the bone screw 2802 and thus anchor the implant 2100 to the vertebra. For example, a user may insert the implant delivery device 2300 through the lumen of the guide tool 2904 such that the distal end of the inner guide tube 2350 is proximate the facet implant 2100. The user may insert the bone screw device 2800 through a proximal end of the inner guide tube and advance the bone screw device 2800 through the proximal portion of the inner guide tube along a first trajectory. The user may continue to advance the bone screw device 2100 through the inner guide tube, and the bend within the guide tube may cause the flexible region of the delivery mechanism to flex. Thus, the bone screw 2802 may exit the distal end of the inner guide tube along a second trajectory so that the bone screw is directed to the inlet of the implant screw cavity. When the bone screw is within the screw cavity, the user may rotate the bone screw device 2800 to cause the bone screw to advance through implant 2100 and into the vertebra. The bone screw may advance through the implant 2100 and into the vertebra along a third trajectory. As the user further screws the screw into the implant 2100 and vertebra, the flexible region further flexes and a load is concentrated at the breakable junction. When the user screws the bone screw 2802 a sufficient amount to anchor the implant 2100 to the vertebra, the breakable junction may experience a predetermined load to cause the bone screw 2802 to detach from the delivery mechanism. The process can then be repeated for another facet joint if needed.

For a further discussion regarding delivery systems and methodology, see U.S. patent application Ser. No. 12/653,283, which was filed on Dec. 10, 2009, and which is entitled "Vertebral Joint Implants and Delivery Tools." The full disclosure of U.S. patent application Ser. No. 12/653,283 is hereby incorporated by reference.

Figure 108:
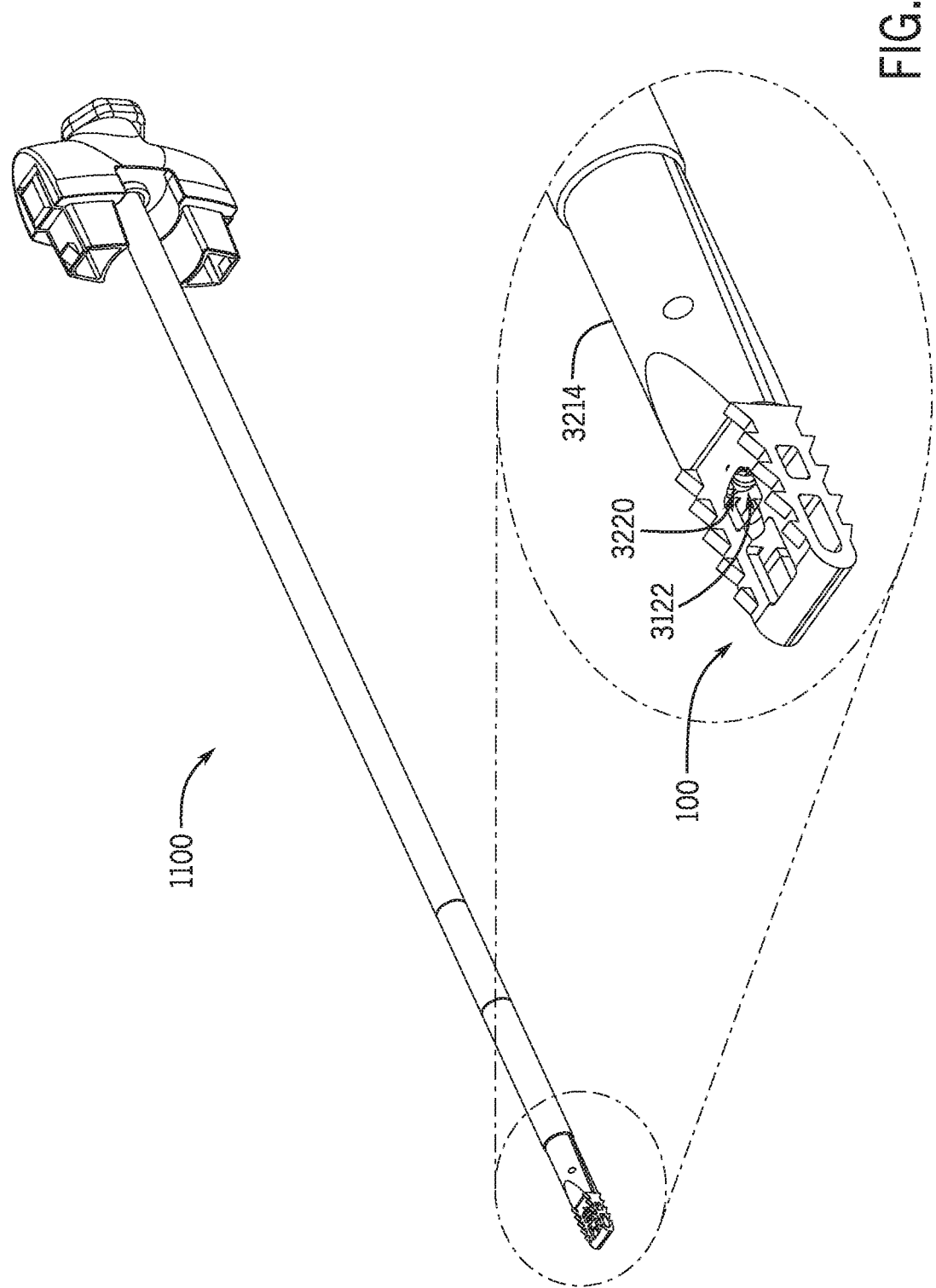

FIGS. 108-109 illustrate how an additional delivery device 3172 may engage with the implant 100. With the exception of the following description, the delivery device 3172 is configured similar to the delivery device 172, 1172 discussed above, and accordingly, like features will not be discussed when they would be apparent to those of skill in the art with reference to FIGS. 108-109 and the discussion above. As can be understood from FIGS. 108-109, the delivery device 3172 may be used to release the implant 100 from the distraction system 1100. Referring to FIGS. 108-109, in one implementation, a flexible shaft or rod 3194 extends from a distal tip 3310 of a shaft 3306 and includes engagement features 3316 at a distal tip 3314 of the flexible shaft 3194. The engagement features 3316 may be any feature adapted to engage the securement feature 160 or a feature of the rear surface 110 of the implant 100. For example, the engagement member 3316 may be threaded members.

As shown in FIGS. 108-109, the implant 100 is interfaced with or otherwise attached to the distal surface 3216 of the elongated tube 3214. To retain the implant 100 in an attached manner to the distraction system 1100, the delivery device 3172 is fully inserted through the guide passage 3224, such that the distal tip 3314 extends through the window 3220 to be received in the hole 3122, and the engagement features 3316 of the flexible shaft 3194 of the release driver 300 engage complementary features of the hole 3122. In other words, the hole 3122 in the implant 100 is adapted to matingly receive the engagement features 316 of the flexible shaft 3194 of the delivery device 3172.

A channel 3222 causes the flexible shaft 3194 of the delivery device 3172 to bend as shown in FIG. 109 as the distal tip 3314 extends proximally from the window 3220 along the guide passage 3224. In other embodiments, the flexible shaft 3194 may just extend through the inner lumen of the shaft 3306 or the channel 3222 may extend longitudinally through the shaft rather than having a bend as shown in FIG. 109. The bending of the flexible shaft 3194 retains the implant 100 in tension. The bending or deflection of the flexible shaft 3194 allows the distal tip 3314 to deflect into the implant hole 3122 despite the implant hole 3122 and the guide passage 3224 not being axially aligned with each other.

To facilitate the insertion of the implant 100 into the facet joint space, a guide tube 2904, as shown in FIG. 100, is employed. In one implementation, the guide tube 2904 extends from a proximal trailing end 2909 to a distal leading end 2907 and includes a tubular shaft 2924 extending between a receiving assembly 2926 and a pair of distal leading end anchoring forks 2934. The receiving assembly 2926 may include a female receiving portion 2928 for receiving and engaging the male members 2914 of the deployment guide 2902. In one implementation, the receiving assembly 2926 includes a raised surface 2932 with a hole defined therein providing an opening to a lumen 2930 extending through the tubular shaft 2924.

In one implementation, the anchoring forks 2934 may be textured distal parallel prongs for accessing a spinal facet joint and through which the distraction system 1100 may be routed to deliver the implant 100 in the facet joint. As illustrated in FIG. 100, in one implementation, the anchoring forks 2934 are parallel prongs having the same height and configuration such that they are mirror images of each other. However, other arrangements are contemplated.

Inserting the deployment guide 2902, interfaced with the implant 100 via the release driver or plunger 2916, into the guide tube 2904, delivers the implant 100 into the spinal facet joint. In some cases, malleting may be needed to fully engage the implant 100 with the joint.

After the implant is delivered to the facet joint, the engagement features 2316 of the flexible shaft 3194 is released from the implant 100, and the delivery device 3172 is withdrawn from the distraction system 1100, leaving the implant 100 in the joint.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. Thus, it is intended that the scope of the present disclosure should not be limited by the particular embodiments described above.

What is claimed is:

1. A spinal implant for implantation within a spinal facet joint, the implant comprising:
   a main body including:
      opposing top and bottom surfaces;
      opposing front and rear surfaces;
      opposing side surfaces; and
      at least one lateral edge defined at an intersection between one of the opposing top and bottom surfaces and one of the opposing side surfaces;
   at least one retaining feature positioned on at least one of the top and bottom surfaces of the main body, said retaining feature including a leading face, a trailing face, opposing lateral faces and a tip formed at an intersection between the faces; and
   at least one securement feature associated with at least one surface of the main body to secure the implant within the spinal facet joint, wherein:
- each lateral face of the at least one retaining feature extends from the top or bottom surface and is positioned at a location away from the at least one lateral edge; and
- the front surface and the rear surface of the main body are defined between the top and bottom surfaces, the front surface is continuous with both the top and bottom surfaces, the front surface is tapered to define a leading edge and a height of the leading edge is less than a height of the rear surface.

2. The spinal implant of claim 1, wherein the at least one securement feature comprises a fastener receiving securement aperture.

3. The spinal implant of claim 1, wherein the at least one securement feature includes a bone screw extending at least partially within at least one window of the implant.

4. The spinal implant of claim 3, wherein at least a portion of the bone screw extends between the top or bottom and rear surfaces of the implant.

5. The spinal implant of claim 1, further comprising an interior wall positioned within the main body.

6. The spinal implant of claim 5, wherein:
- two windows are defined in each of the top, bottom, and opposing side surfaces of the main body; and
- the interior wall defines a portion of each of the two windows defined in the top, bottom, and opposing side surfaces.

7. The spinal implant of claim 5, wherein:
- the at least one securement feature includes a bone screw; and
- the interior wall is notched to receive a portion of the bone screw.

8. The spinal implant of claim 1, wherein the trailing face includes a slope that is greater than a slope of the leading face.

9. The spinal implant of claim 1, wherein the trailing face extends substantially perpendicular to the at least one of the opposing top and bottom surfaces of the main body.

10. The spinal implant of claim 1, wherein the at least one retaining feature has a pyramidal shape.

11. The spinal implant of claim 10, wherein the faces of the pyramidal-shaped retaining feature are congruent.

12. The spinal implant of claim 10, wherein the at least one retaining feature defines a right-angled pyramid.

13. The spinal implant of claim 1, wherein the tip defines a ridge extending a width of the retaining feature.

14. The spinal implant of claim 1, further comprising a second retaining feature, wherein a retaining feature positioned nearer the front or distal surface of the main body has a height that is smaller than a height of the retaining feature positioned away from the front surface or proximate to a proximal surface.

15. The spinal implant of claim 1, further comprising:
- one or more posts extending from the rear surface of the main body in a laterally spaced relationship; and
- the at least one securement feature includes a securement aperture defined within the rear surface between the one or more posts.

16. The spinal implant of claim 1, further comprising a fastener, and wherein the securement aperture is angled such that the fastener extends through one of the top or bottom surfaces and the rear surface of the main body.

* * * * *